United States Patent
Dolente et al.

(10) Patent No.: US 10,092,551 B2
(45) Date of Patent: Oct. 9, 2018

(54) SPIRO-THIAZOLONES

(71) Applicant: Hoffmann-La Roche Inc., Little Falls, NJ (US)

(72) Inventors: Cosimo Dolente, Allschwil (CH); Bernhard Fasching, Basel (CH); Valerie Runtz-Schmitt, Rixheim (FR); Patrick Schnider, Bottmingen (CH)

(73) Assignee: Hoffmann-LaRoche Inc., Little Falls, NJ (US)

(*) Notice: Subject to any disclaimer, the term of this patent is extended or adjusted under 35 U.S.C. 154(b) by 0 days.

(21) Appl. No.: 15/591,980

(22) Filed: May 10, 2017

(65) Prior Publication Data

US 2017/0246153 A1    Aug. 31, 2017

Related U.S. Application Data

(63) Continuation of application No. PCT/EP2015/076278, filed on Nov. 11, 2015.

(30) Foreign Application Priority Data

Nov. 14, 2014  (EP) .................................. 14193294

(51) Int. Cl.
| | |
|---|---|
| C07C 45/45 | (2006.01) |
| A61K 31/438 | (2006.01) |
| C07D 491/107 | (2006.01) |
| C07D 491/20 | (2006.01) |
| A61K 31/41 | (2006.01) |

(52) U.S. Cl.
CPC ............ *A61K 31/438* (2013.01); *A61K 31/41* (2013.01); *C07C 45/45* (2013.01); *C07D 491/107* (2013.01); *C07D 491/20* (2013.01)

(58) Field of Classification Search
CPC .................................................... C07C 45/45
See application file for complete search history.

(56) References Cited

FOREIGN PATENT DOCUMENTS

| WO | 2008/068185 A1 | 6/2008 |
|---|---|---|
| WO | 2008/084005 A1 | 7/2008 |
| WO | 2010/054961 A1 | 5/2010 |

OTHER PUBLICATIONS

ISR for PCT/EP2015/076278 (dated Dec. 16, 2015).

*Primary Examiner* — Shawquia Jackson
(74) *Attorney, Agent, or Firm* — Robert C. Hall

(57) ABSTRACT

Spiro-thiazolones of formula I

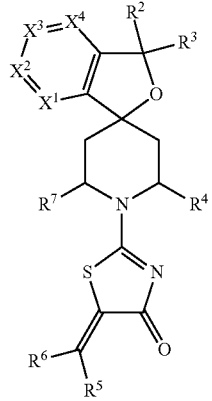

wherein $X^1$, $X^2$, $X^3$, $X^4$, $R^2$, $R^3$, $R^4$, $R^5$, $R^6$ and $R^7$ are as defined herein, which act as V1a receptor modulators, and in particular as V1a receptor antagonists, their manufacture, pharmaceutical compositions containing them and their use as medicaments for treatment of inappropriate secretion of vasopressin, anxiety, depressive disorders, obsessive compulsive disorder, autistic spectrum disorders, schizophrenia, aggressive behavior and phase shift sleep disorders, in particular jetlag.

12 Claims, No Drawings

SPIRO-THIAZOLONES

CROSS-REFERENCE TO RELATED APPLICATIONS

This application is a Continuation of International Application No. PCT/EP2015/076278 filed on Nov. 11, 2015, which is entitled to the priority of EP Application No. 14193294.7 filed on Nov. 14, 2014, the disclosures of which are incorporated herein by reference.

FIELD OF THE INVENTION

The present invention provides spiro-thiazolones, which act as V1a receptor modulators, and in particular as V1a receptor antagonists, their manufacture, pharmaceutical compositions containing them and their use as medicaments. The present compounds are useful as therapeutics acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

BACKGROUND OF THE INVENTION

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al.)[1]. Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann)[2]. Central oxytocin receptor antagonism might therefore lead to anxiogenic effects, which are regarded as undesired side-effects.

In the brain vasopressin acts as a neuromodulator and is elevated in the amygdala during stress (Ebner, et al.)[3]. It is known that stressful life events can trigger major depression and anxiety (Kendler, et al.)[4] and that both have very high comorbidity, with anxiety often preceding major depression (Regier, et al.)[5]. The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al.)[6]. The down-regulation of the V1a receptor using antisense oligonucleotide injection in the septum also causes a reduction in anxious behavior (Landgraf, et al.)[7]. Vasopressin or the V1a receptor are also implicated in other neuropsychological disorders: genetic studies linked sequence polymorphism in the promoter of the human V1a receptor to autistic spectrum disorders (Yirmiya, et al.)[8], intranasal administration of vasopressin was shown to influence aggression in human males (Thompson, et al.)[9] and vasopressin levels were found to be elevated in schizophrenic patients (Raskind, et al.)[10] and patients with obsessive-compulsive disorder (Altemus, et al.)[11].

Autistic Spectrum Disorders (ASD) are a clinically heterogeneous condition characterized by defects in socialization and language. ASD include a wide range of abnormalities including a genuine incapacity to organize affective relations, behavioral anomalies in reciprocal social interactions, verbal and non-verbal communication, limited interest in the surrounding environment associated with stereotyped movements and repetitive plays (Bourreau et al, 2009)[12]. Research to date indicates that a genetic predisposition may be involved, but also environmental factors have to be taken into consideration (Bourgeron, 2009)[13]. There is at present no efficient biological/pharmaceutical treatment to ASD.

The suprachiasmatic nucleus (SCN) is the endogenous clock of the body regulating circadian rhythmicity and is known to be rich in vasopressin neurons (Kalsbeek et al. 2010)[14], producing and releasing vasopressin with a 24 h circadian rhythm (Schwartz et al. 1983)[15]. A major regulatory effect of vasopressin on circadian rhythm could not be demonstrated by the prior art. The Brattleboro rat, a rat strain naturally lacking vasopressin due to a point mutation, has no obvious defect in its circadian rhythm (Groblewski et al. 1981)[16]. Injection of vasopressin directly in the hamster SCN had no effect on circadian phase shift (Albers et al. 1984)[17]. In contrast, the vasopressin receptors were shown to modulate the circadian clock in a more subtle way. Yamaguchi et al (2013)[18] demonstrated that V1a knock-out and V1a/V1b double knock-out mice show faster reentrainment to the new light/dark cycle after a circadian phase advance or a phase delay, an experiment mimicking jet-lag in humans. The same result was obtained after chronic administration of a mixture of V1a and V1b small molecule antagonists through a minipump directly on the SCN.

SUMMARY OF THE INVENTION

The present invention provides a compound of formula I,

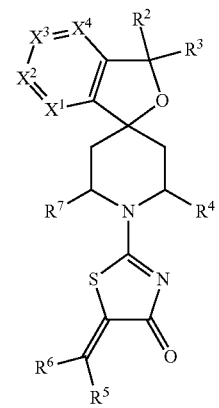

wherein the substituents and variables are as described below and in the claims, or a pharmaceutically acceptable salt thereof.

The present compounds are V1a receptor antagonists, useful for the treatment of autistic spectrum disorders.

DETAILED DESCRIPTION OF THE INVENTION

Object of the present invention is a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with modulation of the V1a receptor, and in particular with V1a receptor antagonism. A further object of the invention is to provide selective inhibitors of the V1a receptor, since selectivity for the V1a receptor is expected to afford a low potential to cause unwanted off-target related side effects such as discussed above.

The following definitions of the general terms used in the present description apply irrespectively of whether the terms in question appear alone or in combination with other groups.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups have 1 to 4 carbon atoms ("$C_{1-4}$-alkyl"). A specific group is methyl.

The term "$C_{2-6}$-alkenyl", alone or in combination with other groups, refers to a branched or straight-chain monovalent unsaturated aliphatic hydrocarbon radical of two to six carbon atoms, preferably two to four carbon atoms.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen ("halogen-$C_{1-3}$-alkyl"), specific 1 halogen or 3 halogen. Particular halogen is fluoro. Particular "halogen-$C_{1-6}$-alkyl" is "fluoro-$C_{1-6}$-alkyl". Examples are $CH_2F$, $CHF_2$ and $CF_3$.

The term "hydrogen", alone or in combination with other terms, includes isotopes like $^1H$ (H) or $^2H$ (D).

The term "hydroxy", alone or in combination with other groups, refers to —OH.

The term "oxo", alone or in combination with other groups, refers to =O.

The term "halogen", alone or in combination with other groups, denotes chloro (Cl), iodo (I), fluoro (F) and bromo (Br).

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms ("$C_{1-4}$-alkoxy"). A specific group is OMe.

The term "heteroaryl", alone or in combination with other groups, refers to an aromatic carbocyclic group of having a single 4 to 8 membered aromatic ring or multiple condensed rings containing 6 to 14, in particular 6 to 10 ring atoms and containing 1, 2 or 3 heteroatoms individually selected from N, O and S, in particular N and O, or 4 N atoms. Particular "heteroaryl" groups are pyridinyl, 1H-pyrrolyl, furanyl, 1H-pyrazolyl, thiazolyl, imidazolyl, furo[3,2-b]pyridinyl and oxazolyl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocyclyl are dihydro-furyl, imidazolinyl, dihydro-oxazolyl, tetrahydro-pyridinyl, or dihydropyranyl. Examples of "heterocyclyl" groups are piperidinyl, tetrahydropyranyl, dihydro-2H-pyran-3(4H)-yl, azepanyl and the like.

Examples of "heterocyclyl" fused with phenyl are 2,3-dihydro-1H-indenyl, 4H-thiopyranyl, 5-2,3,4,5-tetrahydro-1H-2-benzazepinyl, 2-1,3-dihydro-2H-indolyl and isochromen-4(3H)-yl, thioxanthenyl, xanthenyl and the like.

Examples of "$C_{3-6}$-cycloalkyl" fused with phenyl are difluorenyl, 3,4-dihydronaphthalen-1(2H)-yl, 6,7,8,9-tetrahydro-5H-benzo[7]annulenyl, 10, 11-dihydro-5H-dibenzo[a,d][7]annulenyl, 5H-dibenzo[a,d][7]annulenyl and the like.

The term "aryl" denotes a monovalent aromatic carbocyclic mono- or bicyclic ring system comprising 6 to 10 carbon ring atoms. A particular example is phenyl.

The term "halogen-aryl" refers to an aryl moiety as defined herein, substituted by one or more halogen as defined herein. Examples are chloro-aryl groups like chlorophenyl and fluoro-aryl groups like fluoro-phenyl.

The term "$C_{3-9}$-cycloalkyl", alone or in combination with other groups, denotes a monovalent saturated monocyclic or bicyclic hydrocarbon group of 3 to 9 ring carbon atoms, particularly a monovalent saturated monocyclic hydrocarbon group of 3 to 7 ("$C_{3-7}$-cycloalkyl") or 3 to 6 ("$C_{3-6}$-cycloalkyl") ring carbon atoms. Bicyclic means consisting of two saturated carbocycles having two carbon atoms in common, i.e. the bridge separating the two rings is either a single bond or a chain of one or two carbon atoms. Particular $C_{3-9}$-cycloalkyl groups are monocyclic. Examples are cyclopropyl, cyclobutanyl, cyclopentyl, cyclohexyl, cycloheptyl or hexahydro-1,2,4-(methanetriyl)pentalen-5(1H)-yl.

The term "$C_{3-6}$-cycloalkenyl", alone or in combination with other groups, refers to cyclic alkenyl groups as defined herein.

The phrase "one of $X^1$, $X^2$, $X^3$ is C—$R^1$ and $X^4$ is N" means that when $X^4$ is N, at least one of $X^1$, $X^2$ or $X^3$ is C—$R^1$.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (-log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to $pK_i$ values (-log $K_i$), in which higher values indicate exponentially greater potency.

The term "antagonist" denotes a compound that diminishes or prevents the action of another compound as defined e.g. in Goodman and Gilman's "The Pharmacological Basis of Therapeutics, 7th ed." in page 35, Macmillan Publ. Company, Canada, 1985. In particular, antagonists refer to a compound that attenuates the effect of an agonist. A "competitive antagonist" binds to the same site of a receptor as the agonist but does not activate the receptor, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC[19].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The terms "Autistic Spectrum" and "Autistic Spectrum Disorders" summarize conditions classified as pervasive developmental disorders, which include but are not limited to autism, Asperger syndrome, pervasive developmental disorder not otherwise specified (PDD-NOS), childhood disintegrative disorder, Rett syndrome and Fragile X, in particular autism. These disorders are typically characterized by social deficits, communication difficulties, stereotyped or repetitive behaviors and interests, and cognitive delays.

The term "phase shift sleep disorders" summarizes conditions classified as disturbances in the circadian rhythm, i.e. the approximately 24-hour cycles that are generated by an organism, e.g. a human being. Phase shift sleep disorders include, but are not limited to transient disorders like jetlag or a changed sleep schedule due to work, social responsibilities, or illness, as well as chronic disorders like delayed sleep-phase syndrome (DSPS), delayed sleep-phase type (DSPT), advanced sleep-phase syndrome (ASPS), and irregular sleep-wake cycle.

In detail, the present invention provides compounds of the general formula I

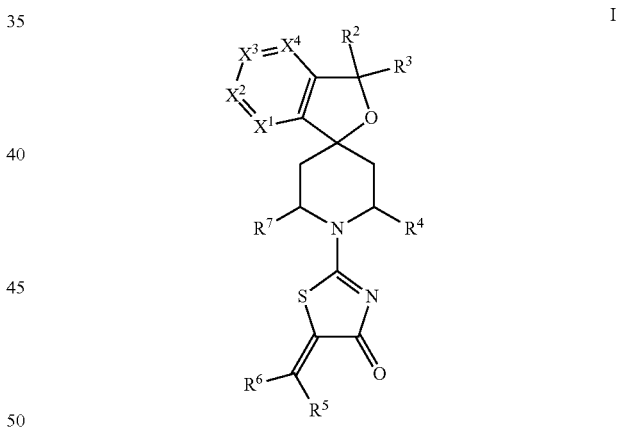

wherein
$X^1$ C—$R^1$ or N;
$X^2$ C—$R^1$ or N;
$X^3$ C—$R^1$ or N;
$X^4$ C—$R^1$ or N;
whereby
  i) one of $X^1$, $X^2$, $X^3$ is C—$R^1$ and $X^4$ is N,
  ii) each of $X^1$, $X^2$, $X^3$ and $X^4$ is C—$R^1$;
$R^1$ each separately is selected from the group consisting of hydrogen, halogen, hydroxy, $C_{1-6}$-alkyl and $C_{1-6}$-alkoxy;
$R^2$ is selected from the group consisting of hydrogen and $C_{1-6}$-alkyl;
$R^3$ is selected from the group consisting of hydrogen and $C_{1-6}$-alkyl;
or $R^2$ and $R^3$ together are =O;
$R^4$ is hydrogen;

$R^5$ is selected from the group consisting of
  i) hydrogen,
  ii) $C_{3-7}$-cycloalkyl,
  iii) $C_{3-7}$-cycloalkyl substituted by one or more substituents individually selected from halogen and $C_{1-6}$-alkyl,
  iv) $C_{1-6}$-alkyl,
  v) $C_{1-6}$-alkyl substituted by one or more substituents individually selected from amino, halogen, hydroxy, $C_{1-6}$-alkoxy, —O—C(=O)—$C_{1-6}$-alkyl, NH(C=O)O—$C_{1-6}$-alkyl and —O—Si($C_{1-6}$-alkyl)$_3$,
  vi) aryl,
  vii) aryl substituted by one or more substituents individually selected from halogen and $C_{1-6}$-alkyl,
  viii) heteroaryl, and
  ix) heteroaryl substituted by one or more substituents individually selected from halogen and $C_{1-6}$-alkyl;
$R^6$ is selected from the group consisting of
  i) $C_{1-6}$-alkyl,
  ii) $C_{1-6}$-alkyl substituted by one or more substituents individually selected from amino, halogen, $C_{1-6}$-alkoxy, —O—C(=O)$C_{1-6}$-alkyl, N($C_{1-6}$-alkyl)$_2$, NH(C=O)O—$C_{1-6}$-alkyl, SO$_2$—$C_{1-6}$-alkyl and —O—Si($C_{1-6}$-alkyl)$_3$;
  iii) $C_{2-6}$-alkenyl
  iv) aryl,
  v) aryl substituted by one or more substituents individually selected from halogen and $C_{1-6}$-alkyl;
  vi) $C_{3-9}$-cycloalkyl,
  vii) $C_{3-9}$-cycloalkyl substituted by one or more substituents individually selected from —(C=O)O—$C_{1-6}$-alkyl, oxo, $C_{1-6}$-alkoxy and $C_{1-6}$-alkyl;
  viii) heterocyclyl,
  ix) heteroaryl, and
  x) heteroaryl substituted by one or more substituents individually selected from halogen, $C_{1-6}$-alkoxy and $C_{1-6}$-alkyl;
or $R^5$ and $R^6$ together are selected from the group consisting of
  i) $C_{3-9}$-cycloalkyl, optionally fused with one or two phenyl,
  ii) $C_{3-9}$-cycloalkyl, optionally fused with phenyl, wherein the phenyl moiety is substituted by one or more substituents individually selected from halogen, hydroxy, (C=O)O—$C_{1-6}$-alkyl, $C_{1-6}$-alkoxy and $C_{1-6}$-alkyl,
  iii) $C_{3-6}$-cycloalkenyl,
  iv) heterocyclyl, optionally fused with one or two phenyl, and
  v) heterocyclyl, optionally fused with phenyl, wherein the heterocyclyl moiety is substituted by one or more substituents individually selected from oxo, (C=O)O—$C_{1-6}$-alkyl and SO$_2$—$C_{1-6}$-alkyl or wherein the phenyl moiety is substituted by one or more halogen;
$R^7$ is hydrogen;
or $R^4$ and $R^7$ together are —(CH$_2$)$_n$—; and
n is 2, 3 or 4;
or pharmaceutically acceptable salts thereof.

A certain embodiment of this invention refers to a compound of formula I as defined herein, wherein
$X^1$ C—$R^1$ or N;
$X^2$ C—$R^1$ or N;
$X^3$ C—$R^1$;
$X^4$ C—$R^1$ or N;
  whereby
  i) one of $X^1$ or $X^2$ is C—$R^1$ and $X^4$ is N, or
  ii) each of $X^1$, $X^2$, $X^3$ and $X^4$ is C—$R^1$;
$R^1$ each separately is hydrogen;
$R^2$ is hydrogen;
$R^3$ is hydrogen;
or $R^2$ and $R^3$ together are =O;
$R^4$ is hydrogen;
$R^5$ is selected from the group consisting of
  i) hydrogen,
  ii) $C_{3-7}$-cycloalkyl,
  iii) $C_{1-6}$-alkyl,
  iv) $C_{1-6}$-alkyl substituted by one or more substituents individually selected from amino, halogen, hydroxy, $C_{1-6}$-alkoxy, —O—C(=O)—$C_{1-6}$-alkyl, NH(C=O)O—$C_{1-6}$-alkyl and —O—Si($C_{1-6}$-alkyl)$_3$,
  v) aryl,
  vi) aryl substituted by halogen, and
  vii) heteroaryl;
$R^6$ is selected from the group consisting of
  i) $C_{1-6}$-alkyl,
  ii) $C_{1-6}$-alkyl substituted by one or more substituents individually selected from amino, halogen, $C_{1-6}$-alkoxy, —O—C(=O)$C_{1-6}$-alkyl, N($C_{1-6}$-alkyl)$_2$, NH(C=O)O—$C_{1-6}$-alkyl, SO$_2$—$C_{1-6}$-alkyl and —O—Si($C_{1-6}$-alkyl)$_3$;
  iii) $C_{2-6}$-alkenyl
  iv) aryl,
  v) aryl substituted by halogen,
  vi) $C_{3-6}$-cycloalkyl,
  vii) heterocyclyl,
  viii) heteroaryl, and
  ix) heteroaryl substituted by one or more substituents individually selected from halogen, $C_{1-6}$-alkoxy and $C_{1-6}$-alkyl;
or $R^5$ and $R^6$ together are selected from the group consisting of
  i) $C_{3-9}$-cycloalkyl, optionally fused with one or two phenyl,
  ii) $C_{3-9}$-cycloalkyl, optionally fused with phenyl, wherein the phenyl moiety is substituted by one or more substituents individually selected from halogen, hydroxy, and $C_{1-6}$-alkoxy,
  iii) $C_{3-6}$-cycloalkenyl,
  iv) heterocyclyl, optionally fused with one or two phenyl, and
  v) heterocyclyl, optionally fused with phenyl, wherein the heterocyclyl moiety is substituted by one or more substituents individually selected from halogen, oxo, (C=O)O—$C_{1-6}$-alkyl and SO$_2$—$C_{1-6}$-alkyl or wherein the phenyl moiety is substituted by one or more halogen;
$R^7$ is hydrogen;
or $R^4$ and $R^7$ together are —(CH$_2$)$_n$—; and
n is 2.

A certain embodiment of this invention refers to a compound of formula I as defined herein, wherein
$X^1$ C—$R^1$ or N;
$X^2$ C—$R^1$ or N;
$X^3$ C—$R^1$;
$X^4$ C—$R^1$ or N;
  whereby
  i) one of $X^1$, $X^2$, $X^3$ is C—$R^1$ and $X^4$ is N, or
  ii) each of $X^1$, $X^2$, $X^3$ and $X^4$ is C—$R^1$;
$R^1$ each separately is hydrogen;
$R^2$ is hydrogen;
$R^3$ is hydrogen;
or $R^2$ and $R^3$ together are =O;
$R^4$ is hydrogen;
$R^5$ is selected from the group consisting of
  i) hydrogen,
  ii) $C_{1-6}$-alkyl, and iii) C$_{1-6}$-alkyl substituted by one substituents individually selected from hydroxyl and C$_{1-6}$-alkoxy, R$^6$ is selected from the group consisting of
i) C$_{1-6}$-alkyl substituted by one C$_{1-6}$-alkoxy;
ii) aryl,
iii) aryl substituted by halogen, and
iv) heteroaryl substituted by one or two substituents individually selected from halogen and C$_{1-6}$-alkyl; and R$^7$ is hydrogen.

A certain embodiment of this invention refers to a compound of formula I as defined herein, wherein
i) X$^1$ is N, X$^2$ is CH, X$^3$ is CH and X$^4$ is CH,
ii) X$^1$ is CH, X$^2$ is CH, X$^3$ is CH and X$^4$ is CH, or
iii) X$^1$ is CH, X$^2$ is CH, X$^3$ is CH and X$^4$ is N.

A certain embodiment of this invention refers to a compound of formula I as defined herein, wherein X$^1$ is CH, X$^2$ is CH, X$^3$ is CH and X$^4$ is CH.

A certain embodiment of this invention refers to a compound of formula I as defined herein, wherein R$^2$ is hydrogen and R$^3$ is hydrogen.

A certain embodiment of this invention refers to a compound of formula I as defined herein, wherein R$^5$ is hydrogen, methyl, —CH$_2$—OCH$_3$, —CH$_2$—OH or —CD$_3$.

A certain embodiment of this invention refers to a compound of formula I as defined herein, wherein R$^5$ is hydrogen.

A certain embodiment of this invention refers to a compound of formula I as defined herein, wherein R$^5$ is methyl.

A certain embodiment of this invention refers to a compound of formula I as defined herein, wherein R$^6$ is phenyl, halogen-phenyl, halogen-pyridinyl, methyl-pyridinyl, dimethyl-oxazolyl or —CH$_2$—OCH$_3$.

A certain embodiment of this invention refers to a compound of formula I as defined herein, wherein R$^6$ is phenyl, chloro-phenyl, fluoro-pyridinyl, chloro-pyridinyl, methyl-pyridinyl, dimethyl-oxazolyl or —CH$_2$—OCH$_3$.

A certain embodiment of this invention refers to a compound of formula I as defined herein, wherein R$^6$ is phenyl or chloro-phenyl.

A certain embodiment of this invention refers to a compound of formula I as defined herein, wherein R$^6$ is fluoro-pyridinyl, chloro-pyridinyl or methyl-pyridinyl.

A certain embodiment of this invention refers to a compound of formula I as defined herein, that is selected from the group consisting of (5E/Z)-5-[1-(4-chlorophenyl)ethylidene]-2-(1'H,3H-spiro[2-benzofuran-1,4'-piperidin]-1'-yl)-1,3-thiazol-4(5H)-one, (5E/Z)-5-[1-(4-chlorophenyl)ethylidene]-2-(1'H,5H-spiro[furo[3,4-b]pyridine-7,4'-piperidin]-1'-yl)-1,3-thiazol-4(5H)-one, 1'-{(5E/Z)-5-[1-(4-chlorophenyl)ethylidene]-4-oxo-4,5-dihydro-1,3-thiazol-2-yl}-3H-spiro[2-benzofuran-1,4'-piperidin]-3-one, (5E/Z)-5-[1-(4-chlorophenyl)ethylidene]-2-(1H,1'H-spiro[furo[3,4-c]pyridine-3,4'-piperidin]-1'-yl)-1,3-thiazol-4(5H)-one and (5Z)-5-[1-(4-chlorophenyl)ethylidene]-2-(1H,1'H-spiro[furo[3,4-c]pyridine-3,4'-piperidin]-1'-yl)-1,3-thiazol-4(5H)-one, 8-{(5E/Z)-5-[1-(4-chlorophenyl)ethylidene]-4-oxo-4,5-dihydro-1,3-thiazol-2-yl}-3'H-spiro[8-azabicyclo[3.2.1]octane-3,1'-[2]benzofuran]-3'-one, (5E/Z)-5-[1-(4-chlorophenyl)ethylidene]-2-(1'H,7H-spiro[furo[3,4-b]pyridine-5,4'-piperidin]-1'-yl)-1,3-thiazol-4(5H)-one, (5E/Z)-5-[1-(6-methylpyridin-3-yl)ethylidene]-2-(1'H,3H-spiro[2-benzofuran-1,4'-piperidin]-1'-yl)-1,3-thiazol-4(5H)-one, (5Z)-5-(4-chlorobenzylidene)-2-(1'H,3H-spiro[2-benzofuran-1,4'-piperidin]-1'-yl)-1,3-thiazol-4(5H)-one, (5Z)-5-benzylidene-2-(1'H,3H-spiro[2-benzofuran-1,4'-piperidin]-1'-yl)-1,3-thiazol-4(5H)-one, (5E/Z)-5-(5-chloro-2,3-dihydro-1H-inden-1-ylidene)-2-(1'H,3H-spiro[2-benzofuran-1,4'-piperidin]-1'-yl)-1,3-thiazol-4(5H)-one, (5E/Z)-5-(6-chloro-3,4-dihydronaphthalen-1(2H)-ylidene)-2-(1'H,3H-spiro[2-benzofuran-1,4'-piperidin]-1'-yl)-1,3-thiazol-4(5H)-one, (5E/Z)-5-[1-(3-chlorophenyl)ethylidene]-2-(1'H,3H-spiro[2-benzofuran-1,4'-piperidin]-1'-yl)-1,3-thiazol-4(5H)-one, (5E/Z)-5-[1-(4-chlorophenyl)propylidene]-2-(1'H,3H-spiro[2-benzofuran-1,4'-piperidin]-1'-yl)-1,3-thiazol-4(5H)-one, (5E/Z)-5-[1-(2-chlorophenyl)ethylidene]-2-(1'H,3H-spiro[2-benzofuran-1,4'-piperidin]-1'-yl)-1,3-thiazol-4(5H)-one, 5-(1,3-dimethoxypropan-2-ylidene)-2-(1'H,3H-spiro[2-benzofuran-1,4'-piperidin]-1'-yl)-1,3-thiazol-4(5H)-one, (5E/Z)-5-(1-phenylethylidene)-2-(1'H,3H-spiro[2-benzofuran-1,4'-piperidin]-1'-yl)-1,3-thiazol-4(5H)-one, (5Z)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one, (5E)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one, (5E/Z)-5-(5-chloro-3,4-dihydronaphthalen-1(2H)-ylidene)-2-(1'H,3H-spiro[2-benzofuran-1,4'-piperidin]-1'-yl)-1,3-thiazol-4(5H)-one, (5E/Z)-5-(7-chloro-3,4-dihydronaphthalen-1(2H)-ylidene)-2-(1'H,3H-spiro[2-benzofuran-1,4'-piperidin]-1'-yl)-1,3-thiazol-4(5H)-one, (5E/Z)-5-[1-(4-chlorophenyl)-2,2-dimethylpropylidene]-2-(1'H,3H-spiro[2-benzofuran-1,4'-piperidin]-1'-yl)-1,3-thiazol-4(5H)-one, (5E/Z)-5-[(4-chlorophenyl)(cyclopropyl)methylidene]-2-(1'H,3H-spiro[2-benzofuran-1,4'-piperidin]-1'-yl)-1,3-thiazol-4(5H)-one, (5E/Z)-5-[1-(4-chlorophenyl)-2-fluoroethylidene]-2-(1'H,3H-spiro[2-benzofuran-1,4'-piperidin]-1'-yl)-1,3-thiazol-4(5H)-one, (5Z)-5-[1-(4-chlorophenyl)propylidene]-2-(1'H,3H-spiro[2-benzofuran-1,4'-piperidin]-1'-yl)-1,3-thiazol-4(5H)-one, (5E)-5-[1-(4-chlorophenyl)propylidene]-2-(1'H,3H-spiro[2-benzofuran-1,4'-piperidin]-1'-yl)-1,3-thiazol-4(5H)-one, (5Z)-5-[1-(4-chlorophenyl)ethylidene]-2-(1'H,3H-spiro[2-benzofuran-1,4'-piperidin]-1'-yl)-1,3-thiazol-4(5H)-one, (5E)-5-[1-(4-chlorophenyl)ethylidene]-2-(1'H,3H-spiro[2-benzofuran-1,4'-piperidin]-1'-yl)-1,3-thiazol-4(5H)-one, (5E)-5-(1-cyclohexylethylidene)-2-(1'H,3H-spiro[2-benzofuran-1,4'-piperidin]-1'-yl)-1,3-thiazol-4(5H)-one, (5Z)-5-(1-cyclohexylethylidene)-2-(1'H,3H-spiro[2-benzofuran-1,4'-piperidin]-1'-yl)-1,3-thiazol-4(5H)-one, 5-(propan-2-ylidene)-2-(1'H,3H-spiro[2-benzofuran-1,4'-piperidin]-1'-yl)-1,3-thiazol-4(5H)-one, (5Z)-5-[1-(pyridin-4-yl)propylidene]-2-(1'H,3H-spiro[2-benzofuran-1,4'-piperidin]-1'-yl)-1,3-thiazol-4(5H)-one, (5E)-5-[1-(pyridin-4-yl)propylidene]-2-(1'H,3H-spiro[2-benzofuran-1,4'-piperidin]-1'-yl)-1,3-thiazol-4(5H)-one, (5Z)-5-[1-(pyridin-4-yl)ethylidene]-2-(1'H,3H-spiro[2-benzofuran-1,4'-piperidin]-1'-yl)-1,3-thiazol-4(5H)-one, (5E/Z)-5-[1-(1H-pyrrol-2-yl)ethylidene]-2-(1'H,3H-spiro[2-benzofuran-1,4'-piperidin]-1'-yl)-1,3-thiazol-4(5H)-one,
(5Z)-5-[1-(furan-2-yl)ethylidene]-2-(1'H,3H-spiro[2-benzofuran-1,4'-piperidin]-1'-yl)-1,3-thiazol-4(5H)-one,
(5E)-5-[1-(pyridin-4-yl)ethylidene]-2-(1'H,3H-spiro[2-benzofuran-1,4'-piperidin]-1'-yl)-1,3-thiazol-4(5H)-one,
(5Z)-5-[1-(1-methyl-1H-pyrrol-2-yl)ethylidene]-2-(1'H,3H-spiro[2-benzofuran-1,4'-piperidin]-1'-yl)-1,3-thiazol-4(5H)-one,
(5Z)-5-[1-(pyridin-2-yl)ethylidene]-2-(1'H,3H-spiro[2-benzofuran-1,4'-piperidin]-1'-yl)-1,3-thiazol-4(5H)-one,
(5Z)-5-[1-(pyridin-3-yl)ethylidene]-2-(1'H,3H-spiro[2-benzofuran-1,4'-piperidin]-1'-yl)-1,3-thiazol-4(5H)-one,
(5E/Z)-5-[1-(2-fluorophenyl)ethylidene]-2-(1'H,3H-spiro[2-benzofuran-1,4'-piperidin]-1'-yl)-1,3-thiazol-4(5H)-one,
tert-butyl 4-[4-oxo-2-(1'H,3H-spiro[2-benzofuran-1,4'-piperidin]-1'-yl)-1,3-thiazol-5(4H)-ylidene]piperidine-1-carboxylate,
(5E/Z)-5-(1-cyclopropylethylidene)-2-(1'H,3H-spiro[2-benzofuran-1,4'-piperidin]-1'-yl)-1,3-thiazol-4(5H)-one,
(5E/Z)-5-(1-cyclopentylethylidene)-2-(1'H,3H-spiro[2-benzofuran-1,4'-piperidin]-1'-yl)-1,3-thiazol-4(5H)-one,
2-(1'H,3H-spiro[2-benzofuran-1,4'-piperidin]-1'-yl)-5-(tetrahydro-4H-pyran-4-ylidene)-1,3-thiazol-4(5H)-one,
(5Z)-5-(3,4-dihydronaphthalen-1(2H)-ylidene)-2-(1'H,3H-spiro[2-benzofuran-1,4'-piperidin]-1'-yl)-1,3-thiazol-4(5H)-one,
(5Z)-5-(2,3-dihydro-1H-inden-1-ylidene)-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-(6,7,8,9-tetrahydro-5H-benzo[7]annulen-5-ylidene)-1,3-thiazol-4(5H)-one,
(5E/Z)-5-[1-(2-chloropyridin-4-yl)ethylidene]-2-(1'H,3H-spiro[2-benzofuran-1,4'-piperidin]-1'-yl)-1,3-thiazol-4(5H)-one,
(5E/Z)-5-[1-(6-chloropyridin-3-yl)ethylidene]-2-(1'H,3H-spiro[2-benzofuran-1,4'-piperidin]-1'-yl)-1,3-thiazol-4(5H)-one,
(5E/Z)-5-(1-methoxypropan-2-ylidene)-2-(1'H,3H-spiro[2-benzofuran-1,4'-piperidin]-1'-yl)-1,3-thiazol-4(5H)-one,
(5E/Z)-5-(1-fluoropropan-2-ylidene)-2-(1'H,3H-spiro[2-benzofuran-1,4'-piperidin]-1'-yl)-1,3-thiazol-4(5H)-one,
5-cyclohexylidene-2-(1'H,3H-spiro[2-benzofuran-1,4'-piperidin]-1'-yl)-1,3-thiazol-4(5H)-one,
5-cyclopentylidene-2-(1'H,3H-spiro[2-benzofuran-1,4'-piperidin]-1'-yl)-1,3-thiazol-4(5H)-one,
(5E/Z)-5-(5-hydroxy-2,3-dihydro-1H-inden-1-ylidene)-2-(1'H,3H-spiro[2-benzofuran-1,4'-piperidin]-1'-yl)-1,3-thiazol-4(5H)-one,
(5E/Z)-5-[hexahydro-1,2,4-(methanetriyl)pentalen-5(1H)-ylidene]-2-(1'H,3H-spiro[2-benzofuran-1,4'-piperidin]-1'-yl)-1,3-thiazol-4(5H)-one,
(5E)-5-[1-(2-fluorophenyl)ethylidene]-2-(1'H,3H-spiro[2-benzofuran-1,4'-piperidin]-1'-yl)-1,3-thiazol-4(5H)-one,
(5Z)-5-[1-(2-fluorophenyl)ethylidene]-2-(1'H,3H-spiro[2-benzofuran-1,4'-piperidin]-1'-yl)-1,3-thiazol-4(5H)-one,
(5E)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one,
(5Z)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one,
5-(1,1-dioxidotetrahydro-4H-thiopyran-4-ylidene)-2-(1'H,3H-spiro[2-benzofuran-1,4'-piperidin]-1'-yl)-1,3-thiazol-4(5H)-one,
(5Z)-5-[1-(2-fluoropyridin-3-yl)ethylidene]-2-(1'H,3H-spiro[2-benzofuran-1,4'-piperidin]-1'-yl)-1,3-thiazol-4(5H)-one,
(5Z)-5-[1-(1-methyl-1H-pyrazol-4-yl)ethylidene]-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-[1-(1,3-thiazol-2-yl)ethylidene]-1,3-thiazol-4(5H)-one,
(5E/Z)-5-[1-(5-methyl-1,2-oxazol-3-yl)propylidene]-2-(1'H,3H-spiro[2-benzofuran-1,4'-piperidin]-1'-yl)-1,3-thiazol-4(5H)-one,
tert-butyl {(2E)-2-[4-oxo-2-(1'H,3H-spiro[2-benzofuran-1,4'-piperidin]-1'-yl)-1,3-thiazol-5(4H)-ylidene]propyl}carbamate,
(5E)-5-(1-aminopropan-2-ylidene)-2-(1'H,3H-spiro[2-benzofuran-1,4'-piperidin]-1'-yl)-1,3-thiazol-4(5H)-one hydrochloride (1:1),
(5E/Z)-8-chloro-5-[4-oxo-2-(1'H,3H-spiro[2-benzofuran-1,4'-piperidin]-1'-yl)-1,3-thiazol-5(4H)-ylidene]-2,3,4,5-tetrahydro-1H-2-benzazepin-1-one,
5-[1-(methylsulfonyl)piperidin-4-ylidene]-2-(1'H,3H-spiro[2-benzofuran-1,4'-piperidin]-1'-yl)-1,3-thiazol-4(5H)-one,
5-(1,3-difluoropropan-2-ylidene)-2-(1'H,3H-spiro[2-benzofuran-1,4'-piperidin]-1'-yl)-1,3-thiazol-4(5H)-one,
(5E/Z)-5-(but-3-en-2-ylidene)-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-(1,1,1-trifluoropropan-2-ylidene)-1,3-thiazol-4(5H)-one,
2-[4-oxo-2-(1'H,3H-spiro[2-benzofuran-1,4'-piperidin]-1'-yl)-1,3-thiazol-5(4H)-ylidene]propane-1,3-diyl diacetate,
(5E/Z)-5-(2-methoxycyclohexylidene)-2-(1'H,3H-spiro[2-benzofuran-1,4'-piperidin]-1'-yl)-1,3-thiazol-4(5H)-one,
(3E/Z)-3-[4-oxo-2-(1'H,3H-spiro[2-benzofuran-1,4'-piperidin]-1'-yl)-1,3-thiazol-5(4H)-ylidene]-1,3-dihydro-2H-indol-2-one,
5-cyclobutylidene-2-(1'H,3H-spiro[2-benzofuran-1,4'-piperidin]-1'-yl)-1,3-thiazol-4(5H)-one,
(5E/Z)-5-(dihydro-2H-pyran-3(4H)-ylidene)-2-(1'H,3H-spiro[2-benzofuran-1,4'-piperidin]-1'-yl)-1,3-thiazol-4(5H)-one,
(5E/Z)-5-[1-(2-methylpyridin-4-yl)ethylidene]-2-(1'H,3H-spiro[2-benzofuran-1,4'-piperidin]-1'-yl)-1,3-thiazol-4(5H)-one,
(5E/Z)-2-(1'H,3H-spiro[2-benzofuran-1,4'-piperidin]-1'-yl)-5-[1-(tetrahydro-2H-pyran-4-yl)ethylidene]-1,3-thiazol-4(5H)-one,
(5Z)-5-[1-(5-methyl-1,2-oxazol-3-yl)ethylidene]-2-(1'H,3H-spiro[2-benzofuran-1,4'-piperidin]-1'-yl)-1,3-thiazol-4(5H)-one),
tert-butyl (4E/Z)-4-[4-oxo-2-(1'H,3H-spiro[2-benzofuran-1,4'-piperidin]-1'-yl)-1,3-thiazol-5(4H)-ylidene]azepane-1-carboxylate,
(5E/Z)-5-(azepan-4-ylidene)-2-(1'H,3H-spiro[2-benzofuran-1,4'-piperidin]-1'-yl)-1,3-thiazol-4(5H)-one hydrochloride,
5-(diphenylmethylidene)-2-(1'H,3H-spiro[2-benzofuran-1,4'-piperidin]-1'-yl)-1,3-thiazol-4(5H)-one,
(5Z)-5-[1-(2-chloropyridin-3-yl)ethylidene]-2-(1'H,3H-spiro[2-benzofuran-1,4'-piperidin]-1'-yl)-1,3-thiazol-4(5H)-one,
(5E)-5-[1-(2-chloropyridin-3-yl)ethylidene]-2-(1'H,3H-spiro[2-benzofuran-1,4'-piperidin]-1'-yl)-1,3-thiazol-4(5H)-one,
(5E/Z)-5-[1-(6-methoxypyridin-3-yl)ethylidene]-2-(1'H,3H-spiro[2-benzofuran-1,4'-piperidin]-1'-yl)-1,3-thiazol-4(5H)-one, (5E/Z)-5-[1-(2,4-dimethyl-1,3-oxazol-5-yl)ethylidene]-2-(1'H,3H-spiro[2-benzofuran-1,4'-piperidin]-1'-yl)-1,3-thiazol-4(5H)-one, (5E/Z)-5-(1H-isochromen-4(3H)-ylidene)-2-(1'H,3H-spiro[2-benzofuran-1,4'-piperidin]-1'-yl)-1,3-thiazol-4(5H)-one, tert-butyl (3E/Z)-3-[4-oxo-2-(1'H,3H-spiro[2-benzofuran-1,4'-piperidin]-1'-yl)-1,3-thiazol-5(4H)-ylidene]piperidine-1-carboxylate, (5E/Z)-5-(3-chloro-6,7,8,9-tetrahydro-5H-benzo[7]annulen-5-ylidene)-2-(1'H,3H-spiro[2-benzofuran-1,4'-piperidin]-1'-yl)-1,3-thiazol-4(5H)-one, (5Z)-5-(pyridin-2-ylmethylidene)-2-(1'H,3H-spiro[2-benzofuran-1,4'-piperidin]-1'-yl)-1,3-thiazol-4(5H)-one, 5-[(5-methyl-1,2-oxazol-3-yl)methylidene]-2-(1'H,3H-spiro[2-benzofuran-1,4'-piperidin]-1'-yl)-1,3-thiazol-4(5H)-one, (5E)-5-(2-methoxy-1-phenylethylidene)-2-(1'H,3H-spiro[2-benzofuran-1,4'-piperidin]-1'-yl)-1,3-thiazol-4(5H)-one, 5-[(5-methyl-1,2-oxazol-3-yl)methylidene]-2-(1'H,3H-spiro[2-benzofuran-1,4'-piperidin]-1'-yl)-1,3-thiazol-4(5H)-one, 5-(pyridin-3-ylmethylidene)-2-(1'H,3H-spiro[2-benzofuran-1,4'-piperidin]-1'-yl)-1,3-thiazol-4(5H)-one, 5-(pyridin-4-ylmethylidene)-2-(1'H,3H-spiro[2-benzofuran-1,4'-piperidin]-1'-yl)-1,3-thiazol-4(5H)-one, (5Z)-5-[1-(6-chloropyridin-3-yl)ethylidene]-2-(1'H,3H-spiro[2-benzofuran-1,4'-piperidin]-1'-yl)-1,3-thiazol-4(5H)-one, (5E)-5-[1-(6-chloropyridin-3-yl)ethylidene]-2-(1'H,3H-spiro[2-benzofuran-1,4'-piperidin]-1'-yl)-1,3-thiazol-4(5H)-one, 5-(10,11-dihydro-5H-dibenzo[a,d][7]annulen-5-ylidene)-2-(1'H,3H-spiro[2-benzofuran-1,4'-piperidin]-1'-yl)-1,3-thiazol-4(5H)-one, 5-(5H-dibenzo[a,d][7]annulen-5-ylidene)-2-(1'H,3H-spiro[2-benzofuran-1,4'-piperidin]-1'-yl)-1,3-thiazol-4(5H)-one, 5-[bis(4-chlorophenyl)methylidene]-2-(1'H,3H-spiro[2-benzofuran-1,4'-piperidin]-1'-yl)-1,3-thiazol-4(5H)-one, 5-[bis(4-fluorophenyl)methylidene]-2-(1'H,3H-spiro[2-benzofuran-1,4'-piperidin]-1'-yl)-1,3-thiazol-4(5H)-one, 2-(1'H,3H-spiro[2-benzofuran-1,4'-piperidin]-1'-yl)-5-(9H-thioxanthen-9-ylidene)-1,3-thiazol-4(5H)-one, 2-(1'H,3H-spiro[2-benzofuran-1,4'-piperidin]-1'-yl)-5-(9H-xanthen-9-ylidene)-1,3-thiazol-4(5H)-one 5-(9H-fluoren-9-ylidene)-2-(1'H,3H-spiro[2-benzofuran-1,4'-piperidin]-1'-yl)-1,3-thiazol-4(5H)-one (5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one, (5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one, (5Z)-5-[1-(1H-imidazol-2-yl)ethylidene]-2-(1'H,3H-spiro[2-benzofuran-1,4'-piperidin]-1'-yl)-1,3-thiazol-4(5H)-one, (5E/Z)-5-[1-(furo[3,2-b]pyridin-2-yl)ethylidene]-2-(1'H,3H-spiro[2-benzofuran-1,4'-piperidin]-1'-yl)-1,3-thiazol-4(5H)-one, (5E/Z)-5-[1-(5-methyl-1H-imidazol-4-yl)ethylidene]-2-(1'H,3H-spiro[2-benzofuran-1,4'-piperidin]-1'-yl)-1,3-thiazol-4(5H)-one, 5-[di(pyridin-2-yl)methylidene]-2-(1'H,3H-spiro[2-benzofuran-1,4'-piperidin]-1'-yl)-1,3-thiazol-4(5H)-one, 5-(1,1,1,3,3,3-hexafluoropropan-2-ylidene)-2-(1'H,3H-spiro[2-benzofuran-1,4'-piperidin]-1'-yl)-1,3-thiazol-4(5H)-one, (5E/Z)-5-[1-(2,4-dimethyl-1,3-thiazol-5-yl)ethylidene]-2-(1'H,3H-spiro[2-benzofuran-1,4'-piperidin]-1'-yl)-1,3-thiazol-4(5H)-one, 5-(1,3-dichloropropan-2-ylidene)-2-(1'H,3H-spiro[2-benzofuran-1,4'-piperidin]-1'-yl)-1,3-thiazol-4(5H)-one, 5-(heptan-4-ylidene)-2-(1'H,3H-spiro[2-benzofuran-1,4'-piperidin]-1'-yl)-1,3-thiazol-4(5H)-one, 5-(dicyclopropylmethylidene)-2-(1'H,3H-spiro[2-benzofuran-1,4'-piperidin]-1'-yl)-1,3-thiazol-4(5H)-one, 5-(2,6-dimethylheptan-4-ylidene)-2-(1'H,3H-spiro[2-benzofuran-1,4'-piperidin]-1'-yl)-1,3-thiazol-4(5H)-one, (5E/Z)-5-[1-(1H-imidazol-5-yl)ethylidene]-2-(1'H,3H-spiro[2-benzofuran-1,4'-piperidin]-1'-yl)-1,3-thiazol-4(5H)-one, 5-(dicyclopentylmethylidene)-2-(1'H,3H-spiro[2-benzofuran-1,4'-piperidin]-1'-yl)-1,3-thiazol-4(5H)-one, 5-[di(pyridin-3-yl)methylidene]-2-(1'H,3H-spiro[2-benzofuran-1,4'-piperidin]-1'-yl)-1,3-thiazol-4(5H)-one, 5-(2,4-dimethylpentan-3-ylidene)-2-(1'H,3H-spiro[2-benzofuran-1,4'-piperidin]-1'-yl)-1,3-thiazol-4(5H)-one, (5E/Z)-5-[1-(methylsulfonyl)propan-2-ylidene]-2-(1'H,3H-spiro[2-benzofuran-1,4'-piperidin]-1'-yl)-1,3-thiazol-4(5H)-one, 5-(di-1H-pyrrol-2-ylmethylidene)-2-(1'H,3H-spiro[2-benzofuran-1,4'-piperidin]-1'-yl)-1,3-thiazol-4(5H)-one, (5E)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one, (5E)-5-(2-hydroxy-1-phenylethylidene)-2-(1'H,3H-spiro[2-benzofuran-1,4'-piperidin]-1'-yl)-1,3-thiazol-4(5H)-one, 5-(dicyclohexylmethylidene)-2-(1'H,3H-spiro[2-benzofuran-1,4'-piperidin]-1'-yl)-1,3-thiazol-4(5H)-one, (5Z)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one, (5Z)-5-(2-hydroxy-1-phenylethylidene)-2-(1'H,3H-spiro[2-benzofuran-1,4'-piperidin]-1'-yl)-1,3-thiazol-4(5H)-one, (5Z)-5-(cyclopent-2-en-1-ylidene)-2-(1'H,3H-spiro[2-benzofuran-1,4'-piperidin]-1'-yl)-1,3-thiazol-4(5H)-one, (5E)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one, (5E)-5-[1-(6-chloropyridin-3-yl)-2-hydroxyethylidene]-2-(1'H,3H-spiro[2-benzofuran-1,4'-piperidin]-1'-yl)-1,3-thiazol-4(5H)-one, (5Z)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one, (5E)-5-[1-(6-chloropyridin-3-yl)-2-methylpropylidene]-2-(1'H,3H-spiro[2-benzofuran-1,4'-piperidin]-1'-yl)-1,3-thiazol-4(5H)-one, (5Z)-5-[1-(6-chloropyridin-3-yl)propylidene]-2-(1'H,3H-spiro[2-benzofuran-1,4'-piperidin]-1'-yl)-1,3-thiazol-4(5H)-one, (5E)-5-[1-(6-chloropyridin-3-yl)propylidene]-2-(1'H,3H-spiro[2-benzofuran-1,4'-piperidin]-1'-yl)-1,3-thiazol-4(5H)-one, 1'-{(5Z)-5-[1-(6-methylpyridin-3-yl)ethylidene]-4-oxo-4,5-dihydro-1,3-thiazol-2-yl}-3H-spiro[2-benzofuran-1,4'-piperidin]-3-one, 1'-{(5E)-5-[1-(6-methylpyridin-3-yl)ethylidene]-4-oxo-4,5-dihydro-1,3-thiazol-2-yl}-3H-spiro[2-benzofuran-1,4'-piperidin]-3-one, 1'-{(5Z)-5-[1-(6-chloropyridin-3-yl)ethylidene]-4-oxo-4,5-dihydro-1,3-thiazol-2-yl}-3H-spiro[2-benzofuran-1,4'-piperidin]-3-one, 1'-{(5E)-5-[1-(6-chloropyridin-3-yl)ethylidene]-4-oxo-4,5-dihydro-1,3-thiazol-2-yl}-3H-spiro[2-benzofuran-1,4'-piperidin]-3-one, 1'-[5-(dicyclopropylmethylidene)-4-oxo-4,5-dihydro-1,3-thiazol-2-yl]-3H-spiro[2-benzofuran-1,4'-piperidin]-3-one, 1'-[(5E)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one, 1'-[(5Z)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one, 1'-[(5Z)-5-(2-hydroxy-1-phenylethylidene)-4-oxo-4,5-dihydro-1,3-thiazol-2-yl]-3H-spiro[2-benzofuran-1,4'-piperidin]-3-one, 1'-[(5E)-5-(2-hydroxy-1-phenylethylidene)-4-oxo-4,5-dihydro-1,3-thiazol-2-yl]-3H-spiro[2-benzofuran-1,4'-piperidin]-3-one, 1'-{(5E)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one, 1'-{(5E)-5-[1-(6-chloropyridin-3-yl)-2-hydroxyethylidene]-4-oxo-4,5-dihydro-1,3-thiazol-2-yl}-3H-spiro[2-benzofuran-1,4'-piperidin]-3-one, 1'-{(5Z)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one, 1'-{(5Z)-5-[1-(6-chloropyridin-3-yl)-2-hydroxyethylidene]-4-oxo-4,5-dihydro-1,3-thiazol-2-yl}3H-spiro[2-benzofuran-1,4'-piperidin]-3-one, 1'-{(5E)-5-[1-(6-chloropyridin-3-yl)-2-methylpropylidene]-4-oxo-4,5-dihydro-1,3-thiazol-2-yl}-3H-spiro[2-benzofuran-1,4'-piperidin]-3-one, 1'-{(5E)-5-[1-(6-chloropyridin-3-yl)propylidene]-4-oxo-4,5-dihydro-1,3-thiazol-2-yl}-3H-spiro[2-benzofuran-1,4'-piperidin]-3-one, 1'-{(5Z)-5-[1-(6-chloropyridin-3-yl)propylidene]-4-oxo-4,5-dihydro-1,3-thiazol-2-yl}-3H-spiro[2-benzofuran-1,4'-piperidin]-3-one, (5Z)-5-(1-phenylethylidene)-2-(1'H,3H-spiro[2-benzofuran-1,4'-piperidin]-1'-yl)-1,3-thiazol-4(5H)-one, (5E)-5-(1-phenylethylidene)-2-(1'H,3H-spiro[2-benzofuran-1,4'-piperidin]-1'-yl)-1,3-thiazol-4(5H)-one, (5E)-5-[1-(6-methylpyridin-3-yl)ethylidene]-2-(1'H,3H-spiro[2-benzofuran-1,4'-piperidin]-1'-yl)-1,3-thiazol-4(5H)-one, (5E)-5-[1-(4-chlorophenyl)-2-methylpropylidene]-2-(1'H,3H-spiro[2-benzofuran-1,4'-piperidin]-1'-yl)-1,3-thiazol-4(5H)-one, (5E)-5-[1-(3-methylpyridin-2-yl)ethylidene]-2-(1'H,3H-spiro[2-benzofuran-1,4'-piperidin]-1'-yl)-1,3-thiazol-4(5H)-one, 1'-[(5Z)-4-oxo-5-(1-phenylethylidene)-4,5-dihydro-1,3-thiazol-2-yl]-3H-spiro[2-benzofuran-1,4'-piperidin]-3-one, 1'-[(5E)-4-oxo-5-(1-phenylethylidene)-4,5-dihydro-1,3-thiazol-2-yl]-3H-spiro[2-benzofuran-1,4'-piperidin]-3-one, (5Z)-5-[1-(3-fluoropyridin-4-yl)ethylidene]-2-(1'H,3H-spiro[2-benzofuran-1,4'-piperidin]-1'-yl)-1,3-thiazol-4(5H)-one, tert-butyl {(2E/Z)-2-[4-oxo-2-(1'H,3H-spiro[2-benzofuran-1,4'-piperidin]-1'-yl)-1,3-thiazol-5(4H)-ylidene]-2-phenylethyl}carbamate, (5E/Z)-5-(2-amino-1-phenylethylidene)-2-(1'H,3H-spiro[2-benzofuran-1,4'-piperidin]-1'-yl)-1,3-thiazol-4(5H)-one trifluoroacetate, 5-(1,3-dihydro-2H-inden-2-ylidene)-2-(1'H,3H-spiro[2-benzofuran-1,4'-piperidin]-1'-yl)-1,3-thiazol-4(5H)-one, (5E/Z)-5-[1-(6-chloropyridin-3-yl)ethylidene]-2-(1'H,7H-spiro[furo[3,4-b]pyridine-5,4'-piperidin]-1'-yl)-1,3-thiazol-4(5H)-one, 5-(1,3-dimethoxypropan-2-ylidene)-2-(1'H,7H-spiro[furo[3,4-b]pyridine-5,4'-piperidin]-1'-yl)-1,3-thiazol-4(5H)-one, (5E/Z)-5-(2-methoxycyclohexylidene)-2-(1'H,7H-spiro[furo[3,4-b]pyridine-5,4'-piperidin]-1'-yl)-1,3-thiazol-4(5H)-one, (5E/Z)-5-[1-(pyridin-3-yl)ethylidene]-2-(1'H,7H-spiro[furo[3,4-b]pyridine-5,4'-piperidin]-1'-yl)-1,3-thiazol-4(5H)-one, (5E/Z)-5-[1-(6-methylpyridin-3-yl)ethylidene]-2-(1'H,7H-spiro[furo[3,4-b]pyridine-5,4'-piperidin]-1'-yl)-1,3-thiazol-4(5H)-one, (5E/Z)-5-[1-(2,4-dimethyl-1,3-oxazol-5-yl)ethylidene]-2-(1'H,7H-spiro[furo[3,4-b]pyridine-5,4'-piperidin]-1'-yl)-1,3-thiazol-4(5H)-one, (5E/Z)-5-(1H-isochromen-4(3H)-ylidene)-2-(1'H,7H-spiro[furo[3,4-b]pyridine-5,4'-piperidin]-1'-yl)-1,3-thiazol-4(5H)-one, (5Z)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one, (5E)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one, (5Z)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one, (5E)-5-[1-(6-chloropyridin-3-yl($^2$H$_3$)ethylidene]-2-(1'H,3H-spiro[2-benzofuran-1,4'-piperidin]-1'-yl)-1,3-thiazol-4(5H)-one, (5Z)-5-[1-phenyl($^2$H$_3$)ethylidene]-2-(1'H,3H-spiro[2-benzofuran-1,4'-piperidin]-1'-yl)-1,3-thiazol-4(5H)-one, and (5E)-5-[1-phenyl($^2$H$_3$)ethylidene]-2-(1'H,3H-spiro[2-benzofuran-1,4'-piperidin]-1'-yl)-1,3-thiazol-4(5H)-one.

A certain embodiment of this invention refers to a compound of formula I as defined herein, that is selected from the group consisting of (5E/Z)-5-[1-(4-chlorophenyl)ethylidene]-2-(1'H,5H-spiro[furo[3,4-b]pyridine-7,4'-piperidin]-1'-yl)-1,3-thiazol-4(5H)-one, 1'-{(5E/Z)-5-[1-(4-chlorophenyl)ethylidene]-4-oxo-4,5-dihydro-1,3-thiazol-2-yl}-3H-spiro[2-benzofuran-1,4'-piperidin]-3-one, (5E/Z)-5-[1-(4-chlorophenyl)ethylidene]-2-(1'H,7H-spiro[furo[3,4-b]pyridine-5,4'-piperidin]-1'-yl)-1,3-thiazol-4(5H)-one, (5Z)-5-[1-(6-methylpyridin-3-yl)ethylidene]-2-(1'H,3H-spiro[2-benzofuran-1,4'-piperidin]-1'-yl)-1,3-thiazol-4(5H)-one, 5-(1,3-dimethoxypropan-2-ylidene)-2-(1'H,3H-spiro[2-benzofuran-1,4'-piperidin]-1'-yl)-1,3-thiazol-4(5H)-one, (5Z)-5-[1-(4-chlorophenyl)ethylidene]-2-(1'H,3H-spiro[2-benzofuran-1,4'-piperidin]-1'-yl)-1,3-thiazol-4(5H)-one, (5E/Z)-5-[1-(6-chloropyridin-3-yl)ethylidene]-2-(1'H,3H-spiro[2-benzofuran-1,4'-piperidin]-1'-yl)-1,3-thiazol-4(5H)-one, (5Z)-5-[1-(2-fluoropyridin-3-yl)ethylidene]-2-(1'H,3H-spiro[2-benzofuran-1,4'-piperidin]-1'-yl)-1,3-thiazol-4(5H)-one, (5E/Z)-5-[1-(2,4-dimethyl-1,3-oxazol-5-yl)ethylidene]-2-(1'H,3H-spiro[2-benzofuran-1,4'-piperidin]-1'-yl)-1,3-thiazol-4(5H)-one,
(5E)-5-(2-methoxy-1-phenylethylidene)-2-(1'H,3H-spiro[2-benzofuran-1,4'-piperidin]-1'-yl)-1,3-thiazol-4(5H)-one,
(5Z)-5-[1-(6-chloropyridin-3-yl)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)ethylidene]-2-(1'H,3H-spiro[2-benzofuran-1,4'-piperidin]-1'-yl)-1,3-thiazol-4(5H)-one,
(5E)-5-(2-hydroxy-1-phenylethylidene)-2-(1'H,3H-spiro[2-benzofuran-1,4'-piperidin]-1'-yl)-1,3-thiazol-4(5H)-one,
(5E)-5-[1-(6-chloropyridin-3-yl)-2-hydroxyethylidene]-2-(1'H,3H-spiro[2-benzofuran-1,4'-piperidin]-1'-yl)-1,3-thiazol-4(5H)-one,
(5Z)-5-(1-phenylethylidene)-2-(1'H,3H-spiro[2-benzofuran-1,4'-piperidin]-1'-yl)-1,3-thiazol-4(5H)-one,
(5E)-5-(1-phenylethylidene)-2-(1'H,3H-spiro[2-benzofuran-1,4'-piperidin]-1'-yl)-1,3-thiazol-4(5H)-one,
1'-[(5Z)-4-oxo-5-(1-phenylethylidene)-4,5-dihydro-1,3-thiazol-2-yl]-3H-spiro[2-benzofuran-1,4'-piperidin]-3-one,
(5Z)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one,
(5Z)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one,
(5Z)-5-[1-phenyl($^2$H$_3$)ethylidene]-2-(1'H,3H-spiro[2-benzofuran-1,4'-piperidin]-1'-yl)-1,3-thiazol-4(5H)-one, and
(5E)-5-[1-phenyl($^2$H$_3$)ethylidene]-2-(1'H,3H-spiro[2-benzofuran-1,4'-piperidin]-1'-yl)-1,3-thiazol-4(5H)-one.

A certain embodiment of this invention refers to a compound of formula I as described herein, whenever prepared by a process as defined herein.

A certain embodiment of this invention refers to a compound of formula I as described herein for use as therapeutically active substance.

A certain embodiment of this invention refers to a compound of formula I as described herein for the use as therapeutically active substance for the therapeutic and/or prophylactic treatment of diseases and disorders which are associated with V1a receptor antagonism.

A certain embodiment of this invention refers to a compound of formula I as described herein for the use as therapeutically active substance acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a pharmaceutical composition comprising a compound of formula I as described herein and a pharmaceutically acceptable carrier and/or a pharmaceutically acceptable auxiliary substance.

A certain embodiment of this invention refers to the use of a compound of formula I as described herein for the manufacture of a medicament for acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a method for the use of a compound as described herein, which is acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag, which method comprises administering said compound of formula I to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds of formula 1 can be prepared according to the following processes.

In a certain embodiment, the compounds of formula (I) of the invention can be manufactured according to a process comprising the step of reacting a compound of formula (II) with a compound of formula (III)

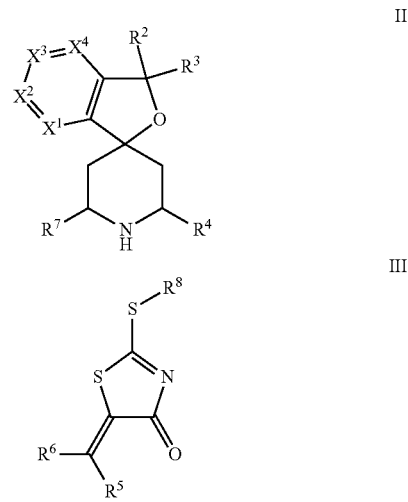

to obtain a compound of formula (I) wherein $X^1$, $X^2$, $X^3$, $X^4$, $R^2$, $R^3$, $R^4$, $R^5$, $R^6$ and $R^7$ are as defined hereinabove for formula (I).

The processes are described in more detail with the following general schemes A to I and procedures 1 to 7.

Scheme 1: General Scheme A

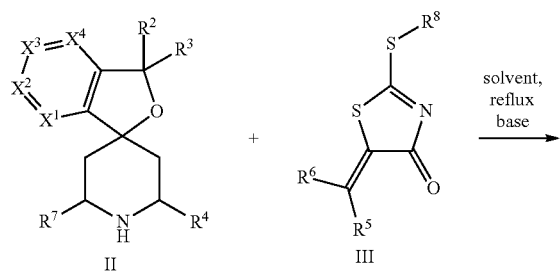

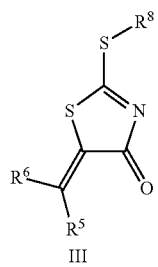

III

Compounds of formula (III) can be prepared from a 2-thioxo-thiazolidin-4-one intermediate of formula (IV) by alkylating the exocyclic sulfur with an alkylating agent $R^8$-LG (wherein $R^8$ is lower alkyl or $CH_2C(=O)OCH_2CH_3$ and LG is a leaving group such as halide or sulfonate) in solvents such as ethanol, 2-propanol or acetone in the presence of a base such as triethylamine or diisopropylethylamine. General Scheme B is hereinafter further illustrated with general procedure 2.

Scheme 3: General Scheme C

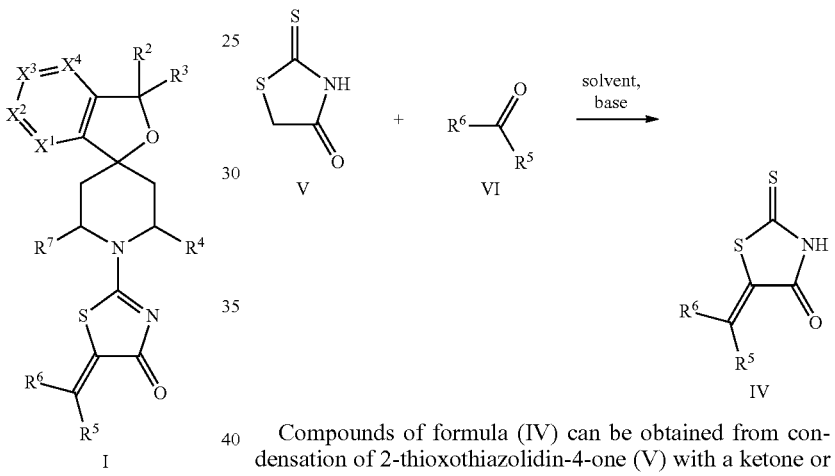

Compounds of formula (IV) can be obtained from condensation of 2-thioxothiazolidin-4-one (V) with a ketone or an aldehyde of formula (VI) that is either commercially available or easily prepared by someone skilled in the art. Reactions are carried out in a solvent such as toluene or dichloromethane at temperatures between 20 and 120° C. in the presence of a base such as an amine or sodium acetate. General Scheme C is hereinafter further illustrated with general procedure 1.

Compounds of formula (I) can be prepared by thermal condensation of a secondary amine of formula (II) and a 2-sulfanyl-thiazol-4-one of formula (III). Secondary amines of formula (II) are either commercially available or can be prepared by methods known in the art or described hereinafter. The syntheses of compounds of formula (III) are outlined in general schemes B and C hereinafter. General Scheme A is hereinafter further illustrated with general procedure 5.

Scheme 4: General Scheme D

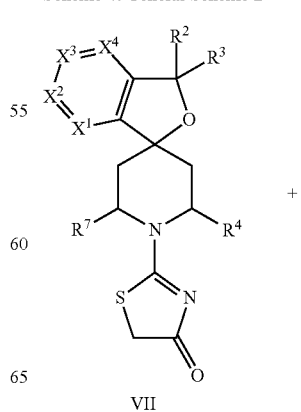

Scheme 2: General Scheme B

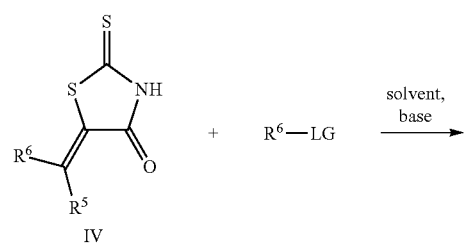

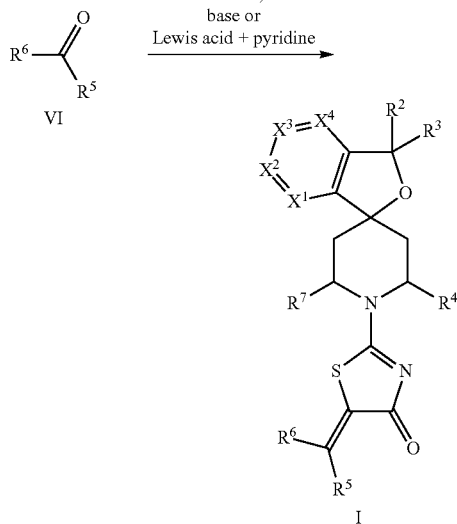

Alternatively, compounds of formula (I) can be prepared by the condensation of a 2-aminothiazol-4-one derivative of formula (VII) with an aldehyde or ketone of formula (VI) that is either commercially available or easily prepared by someone skilled in the art. The condensations are carried out in a solvent such as dichloromethane or toluene at temperatures between 20 and 120° C. in the presence of a base such as acetate or a Lewis acid such as titanium tetrachloride and pyridine. General Scheme D is hereinafter further illustrated with general procedures 6 and 7.

Scheme 5: General Scheme E

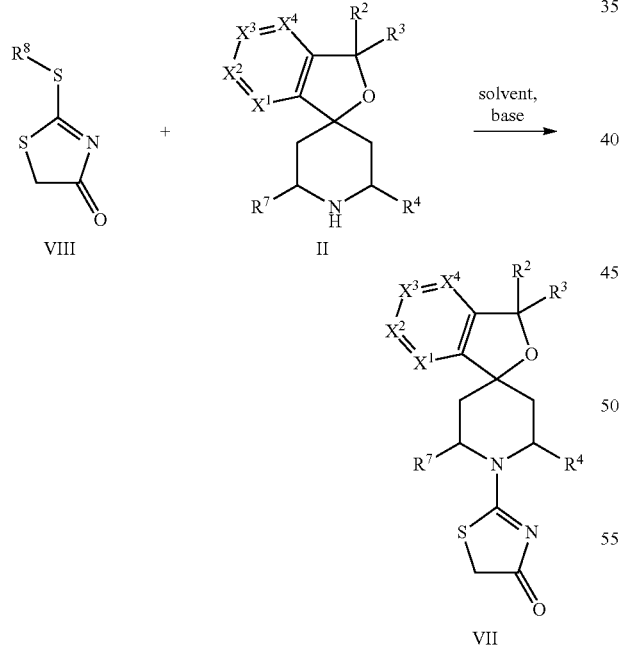

Compounds of formula (VII) are prepared by the condensation of a sulfanylthiazol-4-one of formula (VIII) with a secondary amine of formula (II). Secondary amines of formula (II) are either commercially available or can be prepared by methods known in the art or described hereinafter. The condensations are carried out in a solvent such as ethanol or 2-propanol at temperatures between 20 and 120° C. in the presence of an organic base such as triethylamine or diisopropylethylamine. General Scheme E is hereinafter further illustrated with general procedure 4.

Scheme 6: General Scheme F

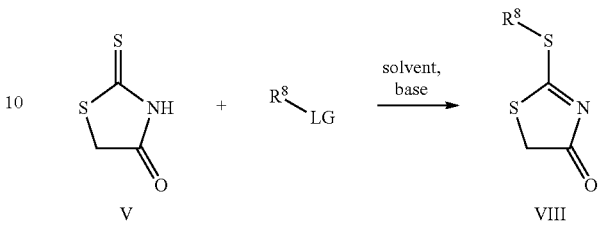

Compounds of formula (VIII) can be obtained by alkylation of 2-thioxothiazolidin-4-one (V) with an alkylating agent $R^8$-LG (wherein $R^8$ is lower alkyl or $CH_2C(=O)OCH_2CH_3$ and LG is a leaving group such as halide or sulfonate) in a solvent such as ethanol, 2-propanol or acetone in the presence of a base such as triethylamine or diisopropylethylamine. General Scheme F is hereinafter further illustrated with general procedure 3.

Scheme 13: General Scheme G

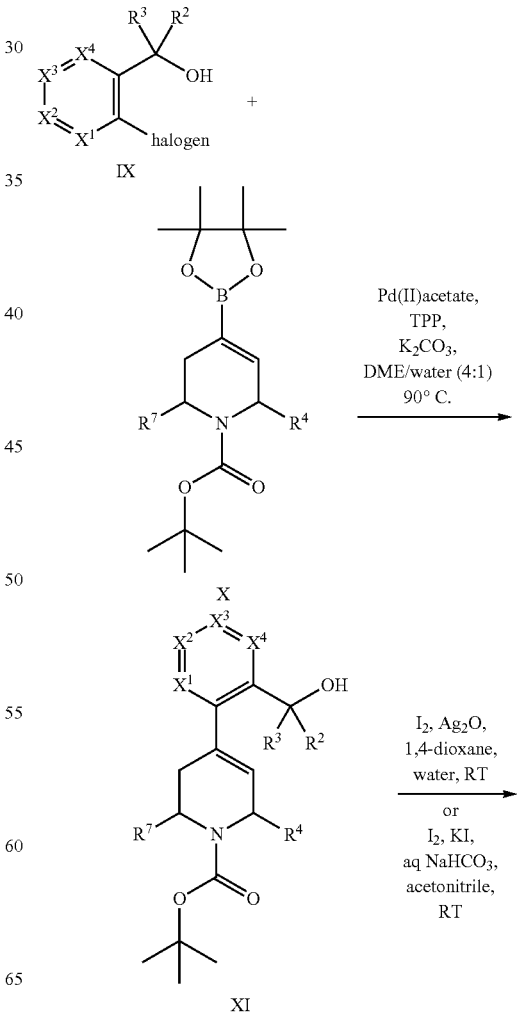

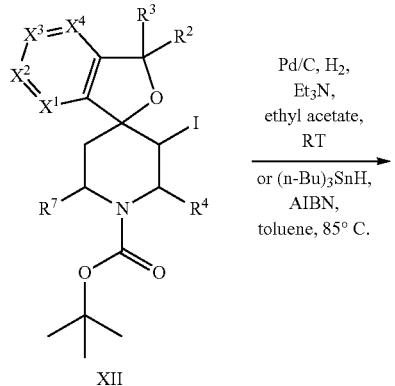

XII

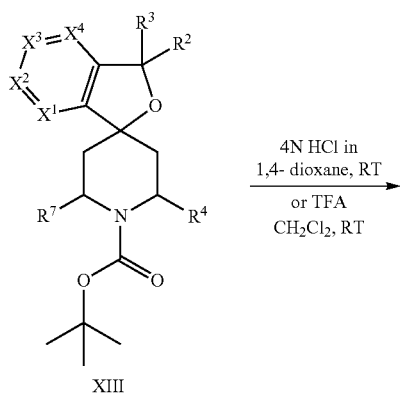

XIII

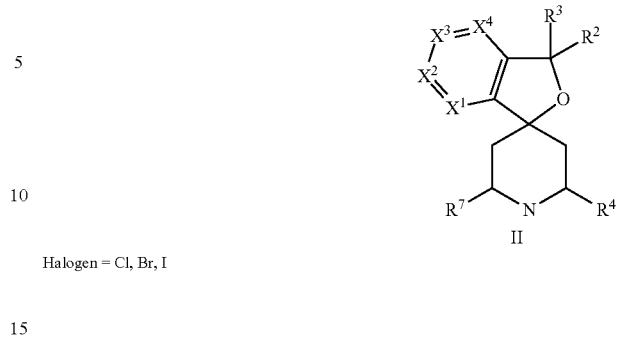

II

Halogen = Cl, Br, I

Amine intermediates of formula (II) can be prepared as described hereinafter: Cross coupling of an aromatic halide of formula (IX), which is commercially available or prepared by methods known in the art, with a boronic acid ester of formula (X) in the presence of a palladium catalyst, e.g. formed in situ from palladium acetate and triphenylphosphine, and an inorganic base such as potassium carbonate gives a tetrahydropyridine derivative of formula (XI). Compounds of formula (XI) can be cyclized with iodine and silver (I) oxide in a 1,4-dioxane/water mixture or with iodine and potassium iodide in a water/acetonitrile mixture to give spiro iodo-piperidines of formula (XII). Compounds of formula (XIII) can be obtained under hydrogenolytic conditions, e.g. using hydrogen gas in the presence of palladium on charcoal and an organic base such as triethyl amine, or using tri-n-butyltin hydride and a radical starter such as azobisisobutyronitrile. N-BOC-deprotection (BOC=tert-butyloxycarbonyl) of compounds of formula (XIII) under acidic conditions, e.g. hydrogen chloride in 1,4-dioxane or trifluoroacetic acid in dichloromethane, gives amine intermediates of formula (II).

Scheme 14: General Scheme H

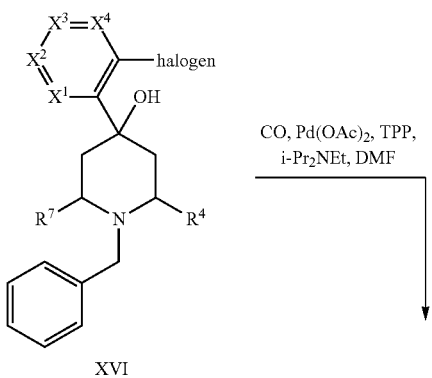

XVI

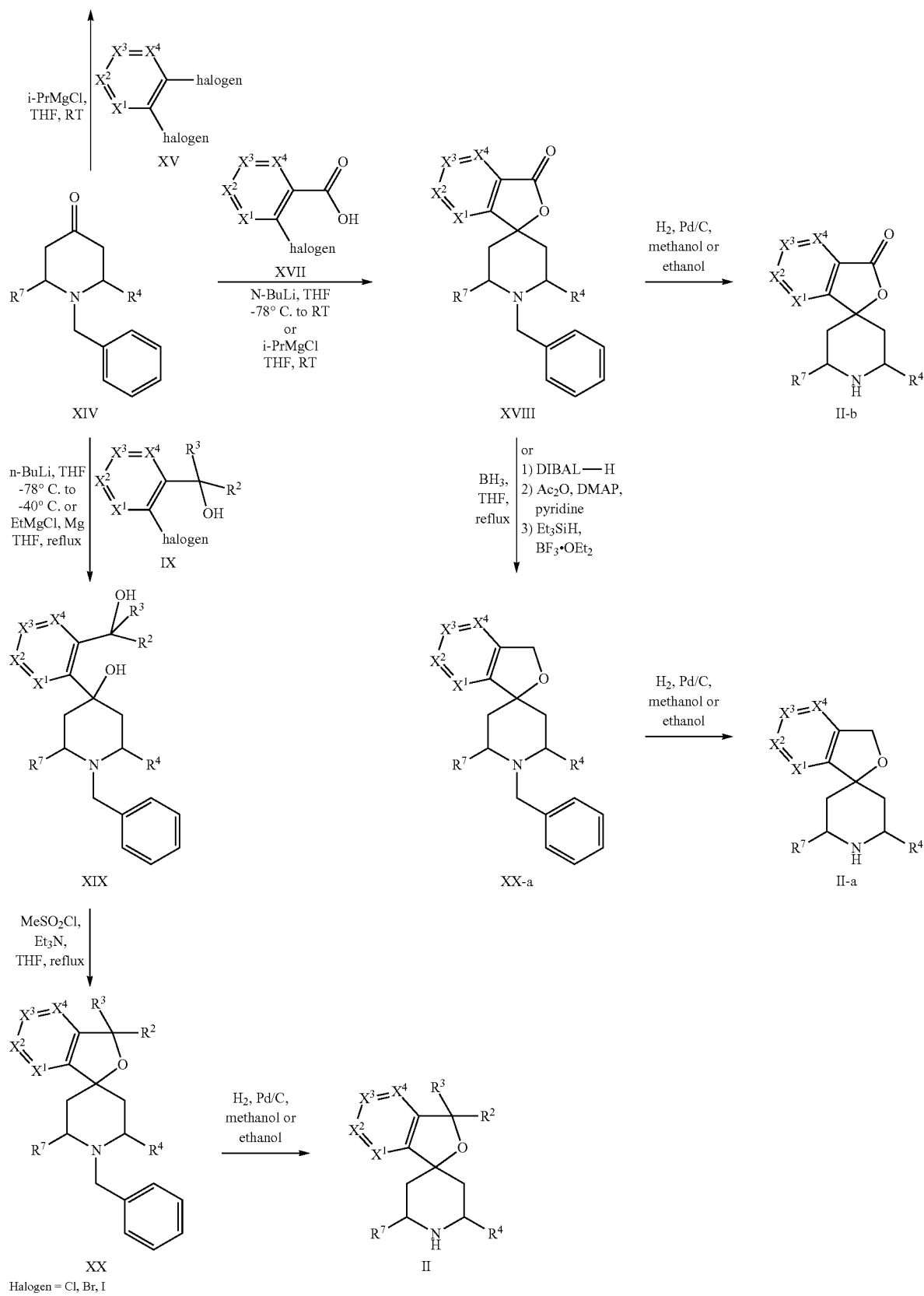

Amine intermediates of formulas (II), (II-a) and (II-b) can be prepared as described hereinafter: Double-lithiation of an o-halo-carboxylic acid derivative of formula (XVII) via O-deprotonation and halogen-lithium exchange with an alkyllithium reagent and subsequent addition to N-benzyl piperidone (XIV) leads to a spirolactone derivative of formula (XVIII). Compounds of formula (XVIII) can be reduced either directly with borane or using a stepwise procedure by consecutive treatment with diisopropylaluminum hydride, acetic anhydride in the presence of pyridine and 4-N,N-dimethylaminopyridine, and triethylsilane in the presence of boron trifluoride to yield compounds of formula (XX-a). Double-metallation of a compound of formula (IX), which is commercially available or prepared by methods known in the art, via O-deprotonation and halogen-metal exchange with magnesium, or a Grignard or alkyllithium reagent, and subsequent addition to N-benzylpiperidone (XIV) leads to a diol derivative of formula (XIX). Cyclization of the diol derivatives of formula (XIX) with methanesulfonyl chloride using a base such as triethylamine leads to spiro derivatives of formula (XX). Treatment of compounds of formula (XV), which are commercially available or prepared by methods known in the art, with isopropyl magnesium chloride leads to the formation of a Grignard reagent which is added to the carbonyl moiety of 1-benzyl-4-piperidone (XIV) to form compounds of formula (XVI). Treatment of a compound of formula (XVI) with carbon monoxide in the presence of a palladium catalyst e.g. formed in situ from palladium acetate and triphenylphosphine, and an amine base gives spirolactone compounds of formula (XVIII). Amine derivatives of formulas (II), (II-a) and (II-b) are obtained by palladium-catalyzed hydrogenolytic N-debenzylation of compounds of formulas (XVIII), (XX) and (XX-a), respectively.

Scheme 14: General Scheme I

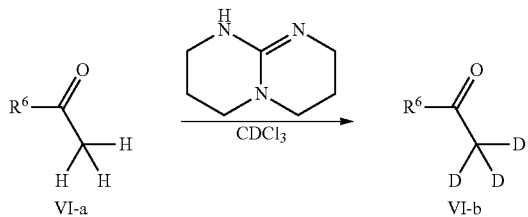

Trideuterated methyl ketones of the formula (VI-b) can easily be prepared by treating the corresponding triple-H compound with 2,3,4,6,7,8-hexahydro-1H-pyrimido[1,2-a]pyrimidine in deuterated chloroform.

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are re-suspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is re-suspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 μl of bead/membrane mixture is then added to each well of a 96 well plate, followed by 50 μl of 4 nM 3H-Vasopressin (American Radiolabeled Chemicals). For total binding measurement 100 μl of binding buffer are added to the respective wells, for non-specific binding 100 μl of 8.4 mM cold vasopressin and for compound testing 100 μl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the $K_i$ is calculated using the Cheng-Prussoff equation.

The following representative data show the antagonistic activity against human $V_{1a}$ receptor of compounds according to present invention:

TABLE 1
pKi values of selected examples
| Ex. | Structure | pK$_i$ hV$_{1a}$ |
|---|---|---|
| 1 | 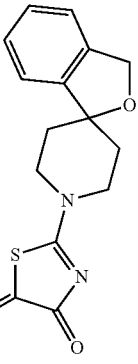 | 8.9 |
| 2 | 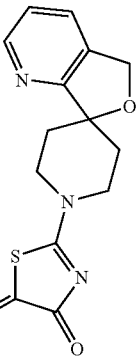 | 9.0 |
| 3 | 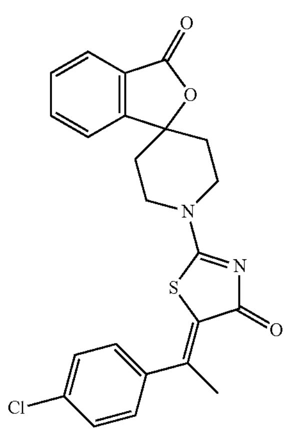 [SMILES: C/C(=C1/SC(N2CCC3(CC2)OC(=O)c2ccccc23)=NC1=O)c1ccc(Cl)cc1] | 9.0 |
| 4 | 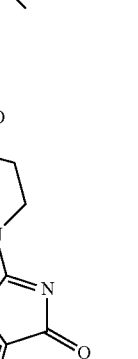 | 9.0 |
| 5 | 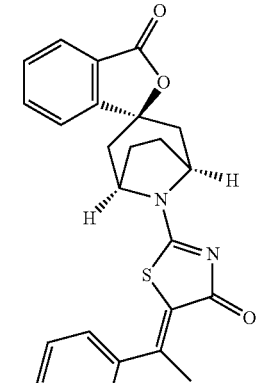 | 8.9 |
| 6 | 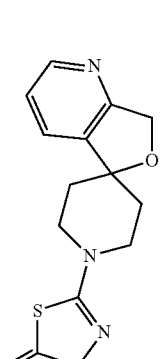 | 9.3 |
| 7 | 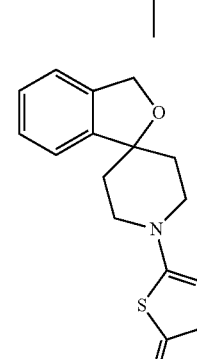 | 8.9 |
| 8 | 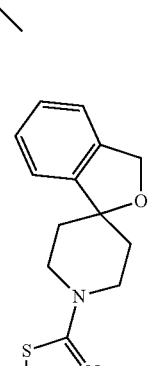 | 7.8 |

TABLE 1-continued
pKi values of selected examples
| Ex. | Structure | pK$_i$ hV$_{1a}$ |
|---|---|---|
| 9 | 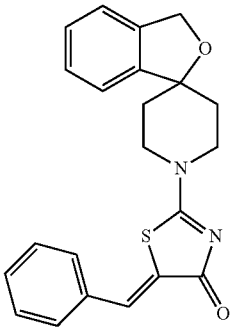 [SMILES: O=C1N=C(N2CCC3(CC2)OCc2ccccc23)S/C1=C\c1ccccc1] | 8.4 |
| 10 | 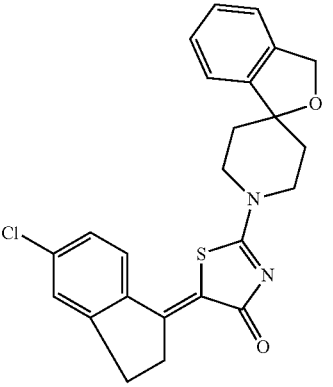 [SMILES: O=C1N=C(N2CCC3(CC2)OCc2ccccc23)S/C1=C1/CCc2cc(Cl)ccc21] | 6.9 |
| 11 | 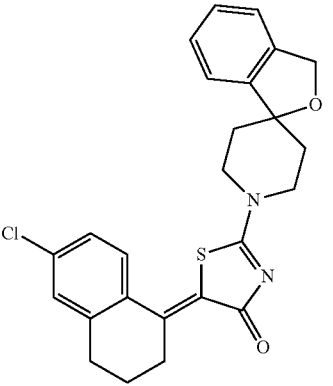 [SMILES: O=C1N=C(N2CCC3(CC2)OCc2ccccc23)S/C1=C1/CCCc2cc(Cl)ccc21] | 8.4 |
| 12 | 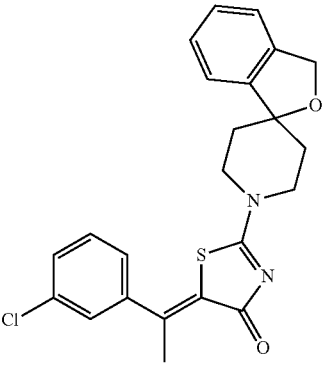 [SMILES: C/C(=C1/SC(N2CCC3(CC2)OCc2ccccc23)=NC1=O)c1cccc(Cl)c1] | 8.2 |
| 13 | 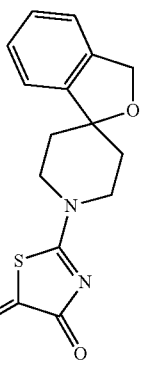 | 8.0 |
| 14 | 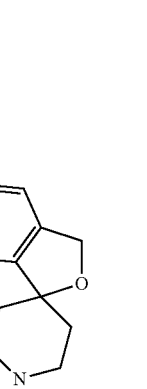 | 8.5 |
| 15 | 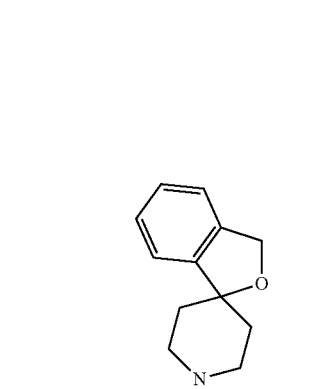 | 8.8 |

TABLE 1-continued pKi values of selected examples

| Ex. | Structure | pK$_i$ hV$_{1a}$ |
|---|---|---|
| 16 | 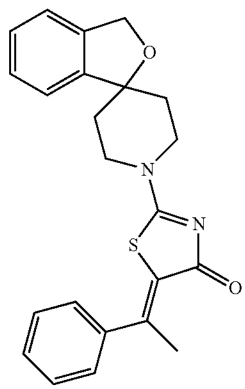 [SMILES: C/C(=C1/SC(N2CCC3(CC2)OCc2ccccc23)=NC1=O)c1ccccc1] | 8.5 |
| 17 | 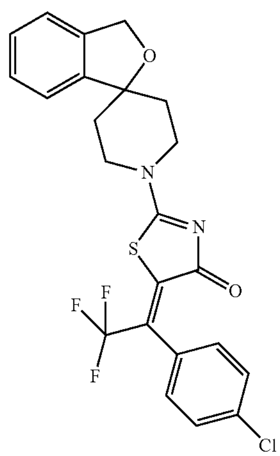 [SMILES: O=C1N=C(N2CCC3(CC2)OCc2ccccc23)S/C1=C(/c1ccc(Cl)cc1)C(F)(F)F] | 8.5 |
| 18 | 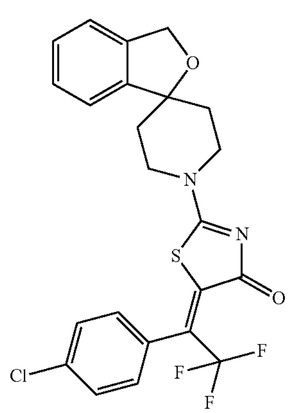 [SMILES: O=C1N=C(N2CCC3(CC2)OCc2ccccc23)S/C1=C(\c1ccc(Cl)cc1)C(F)(F)F] | 9.1 |
| 19 | | 7.7 |
| 20 | | 9.0 |
| 21 | | 7.9 |

TABLE 1-continued
pKi values of selected examples
| Ex. | Structure | pK$_i$ hV$_{1a}$ |
|---|---|---|
| 22 | 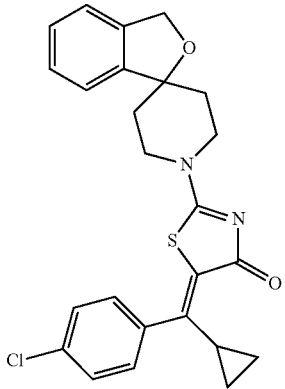 [SMILES: O=C1N=C(N2CCC3(CC2)OCc2ccccc23)S/C1=C(\c1ccc(Cl)cc1)C1CC1] | 7.8 |
| 23 | 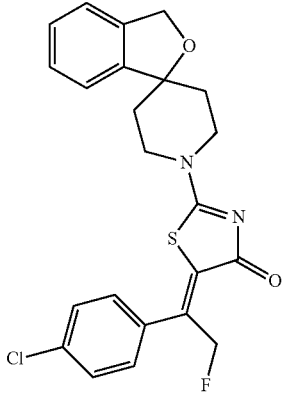 [SMILES: O=C1N=C(N2CCC3(CC2)OCc2ccccc23)S/C1=C(/CF)c1ccc(Cl)cc1] | 9.4 |
| 24 | 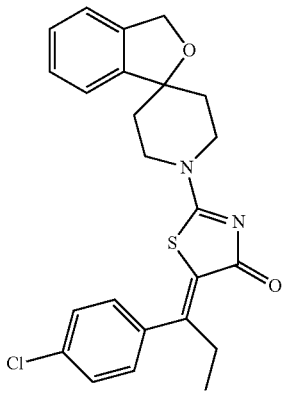 [SMILES: CC/C(=C1/SC(N2CCC3(CC2)OCc2ccccc23)=NC1=O)c1ccc(Cl)cc1] | 9.1 |
| 25 | 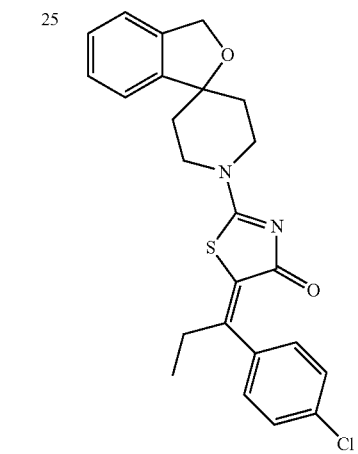 | 8.2 |
| 26 | 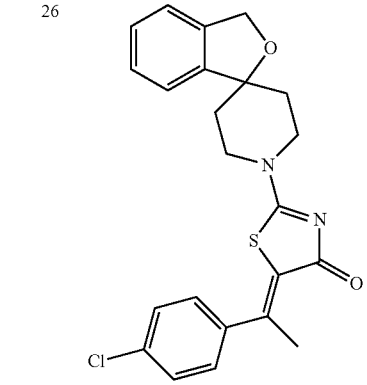 | 9.2 |
| 27 | 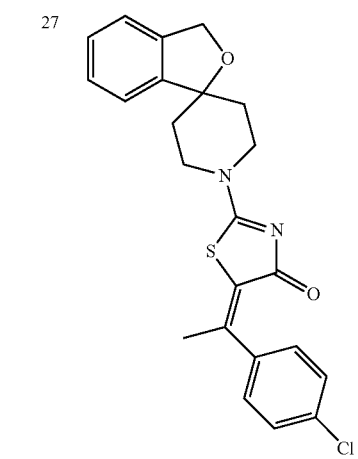 | 8.3 |

TABLE 1-continued pKi values of selected examples

| Ex. | Structure | pK$_i$ hV$_{1a}$ |
|---|---|---|
| 28 | (spiro isobenzofuran-piperidine-thiazolone with ethylidene-cyclohexyl) | 7.9 |
| 29 | (spiro isobenzofuran-piperidine-thiazolone with cyclohexyl-methyl ethylidene) | 8.7 |
| 30 | (spiro isobenzofuran-piperidine-thiazolone with isopropylidene) | 7.8 |
| 31 | (spiro isobenzofuran-piperidine-thiazolone with 1-(pyridin-4-yl)propylidene) | 8.4 |
| 32 | (spiro isobenzofuran-piperidine-thiazolone with 1-(pyridin-4-yl)propylidene) | 7.9 |
| 33 | (spiro isobenzofuran-piperidine-thiazolone with 1-(pyridin-4-yl)ethylidene) | 8.3 |
| 34 | (spiro isobenzofuran-piperidine-thiazolone with 1-(1H-pyrrol-2-yl)ethylidene) | 9.2 |

TABLE 1-continued
pKi values of selected examples
| Ex. | Structure | pK$_i$ hV$_{1a}$ |
|---|---|---|
| 35 | 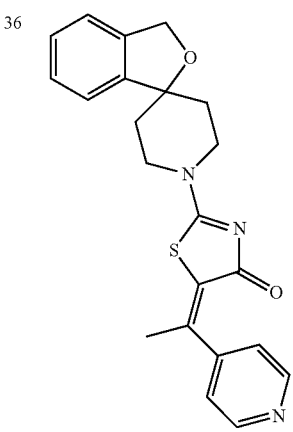 | 8.9 |
| 36 | 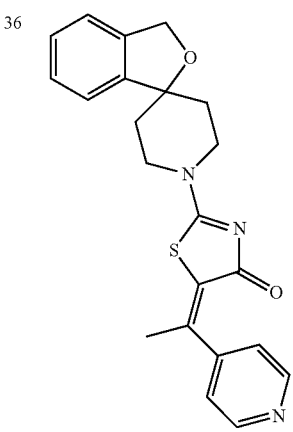 | 7.5 |
| 37 | 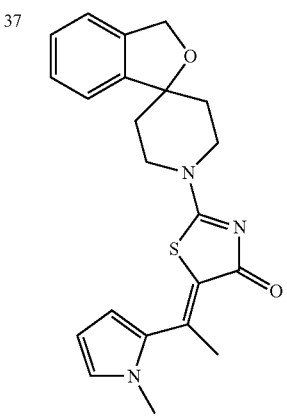 | 9.1 |
| 38 | 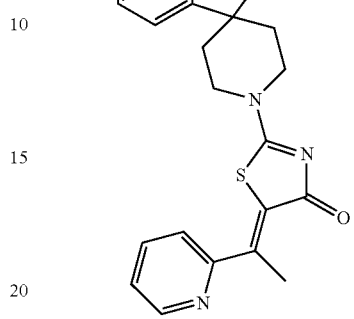 | 8.8 |
| 39 | 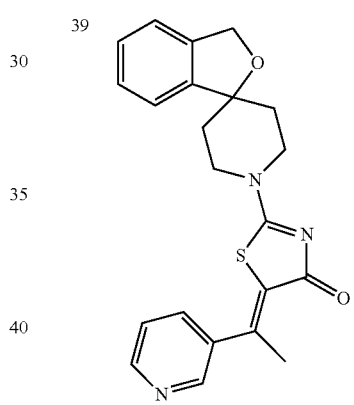 | 8.9 |
| 40 | 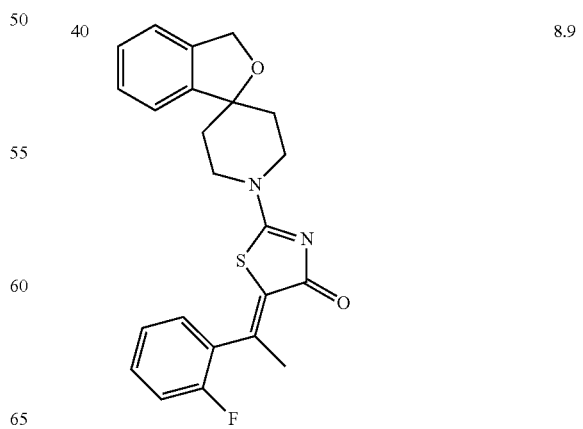 | 8.9 |

TABLE 1-continued pKi values of selected examples

| Ex. | Structure | pK$_i$ hV$_{1a}$ |
|---|---|---|
| 41 | 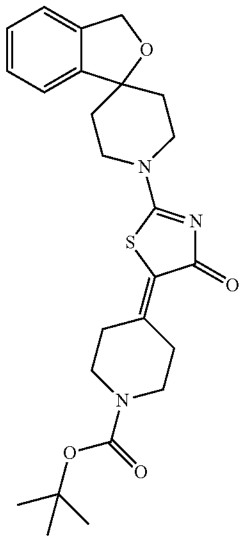 [SMILES: CC(C)(C)OC(=O)N1CCC(=C2SC(N3CCC4(CC3)OCc3ccccc34)=NC2=O)CC1] | 7.6 |
| 42 | 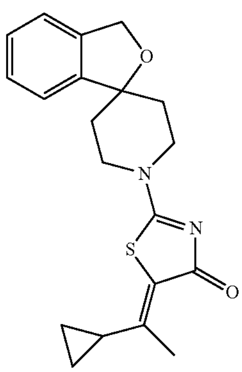 [SMILES: C/C(=C1/SC(N2CCC3(CC2)OCc2ccccc23)=NC1=O)C1CC1] | 8.4 |
| 43 | 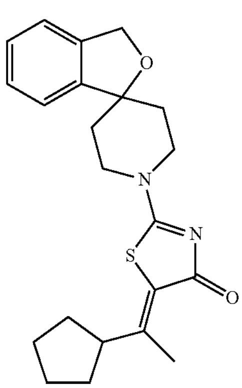 [SMILES: C/C(=C1/SC(N2CCC3(CC2)OCc2ccccc23)=NC1=O)C1CCCC1] | 8.8 |
| 44 | | 8.1 |
| 45 | | 8.7 |
| 46 | | 8.3 |

TABLE 1-continued pKi values of selected examples

| Ex. | Structure | pK$_i$ hV$_{1a}$ |
|---|---|---|
| 47 | | 9.3 |
| 48 | | 8.6 |
| 49 | | 9.1 |
| 50 | 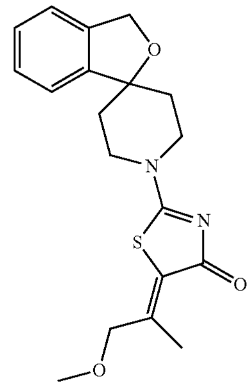 [SMILES: COC/C(C)=C1\SC(N2CCC3(CC2)OCc2ccccc23)=NC1=O] | 8.4 |
| 51 | 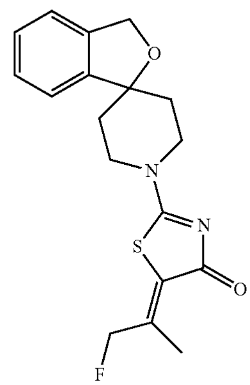 [SMILES: C/C(CF)=C1/SC(N2CCC3(CC2)OCc2ccccc23)=NC1=O] | 7.9 |
| 52 | 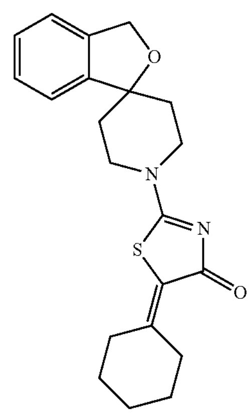 [SMILES: O=C1N=C(N2CCC3(CC2)OCc2ccccc23)SC1=C1CCCCC1] | 8.5 |
| 53 | 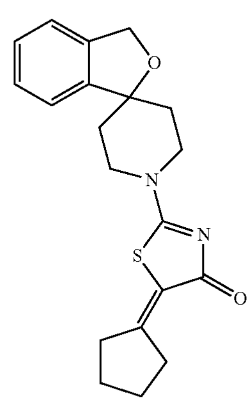 [SMILES: O=C1N=C(N2CCC3(CC2)OCc2ccccc23)SC1=C1CCCC1] | 8.3 |

TABLE 1-continued
pKi values of selected examples
| Ex. | Structure | pK$_i$ hV$_{1a}$ |
|---|---|---|
| 54 | 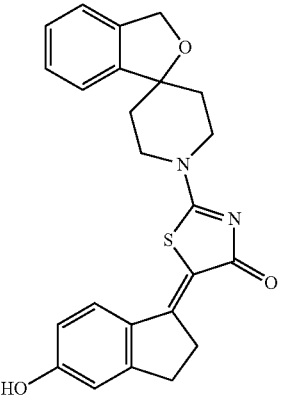 [SMILES: O=C1N=C(N2CCC3(CC2)OCc2ccccc23)S/C1=C1/CCc2cc(O)ccc21] | 7.5 |
| 55 | 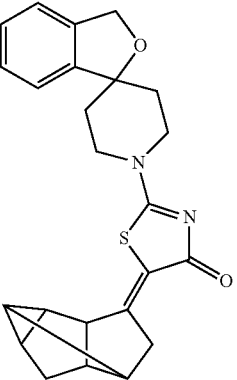 [SMILES: O=C1N=C(N2CCC3(CC2)OCc2ccccc23)S/C1=C1/CC2C3CC4C2C4C13] | 8.3 |
| 56 | 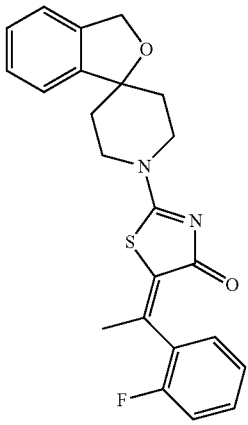 [SMILES: C/C(=C1\SC(N2CCC3(CC2)OCc2ccccc23)=NC1=O)c1ccccc1F] | 8.3 |
| 57 | 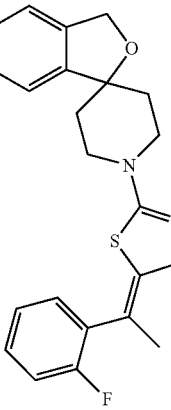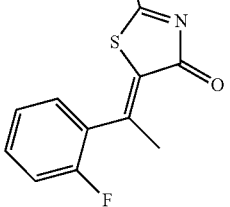 | 9.0 |
| 58 | 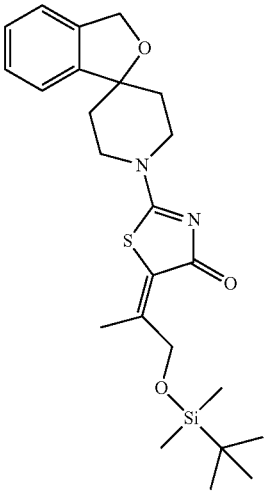 [SMILES: C/C(CO[Si](C)(C)C(C)(C)C)=C1\SC(N2CCC3(CC2)OCc2ccccc23)=NC1=O] | 7.2 |
| 59 | 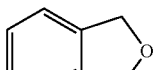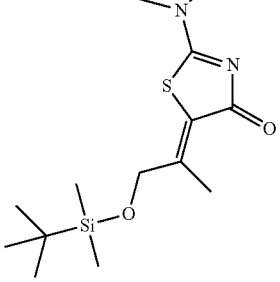 | 6.5 |

TABLE 1-continued
pKi values of selected examples
| Ex. | Structure | pK$_i$ hV$_{1a}$ |
|---|---|---|
| 60 | 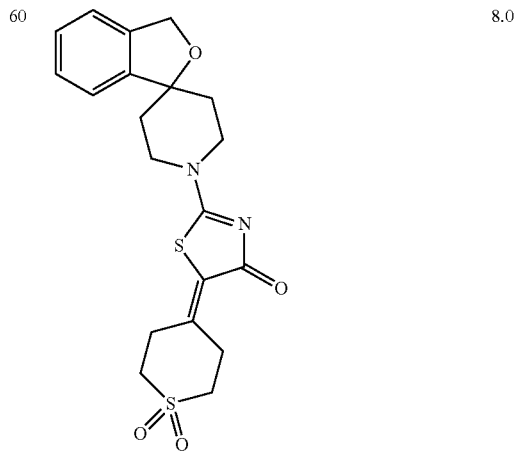 | 8.0 |
| 61 | 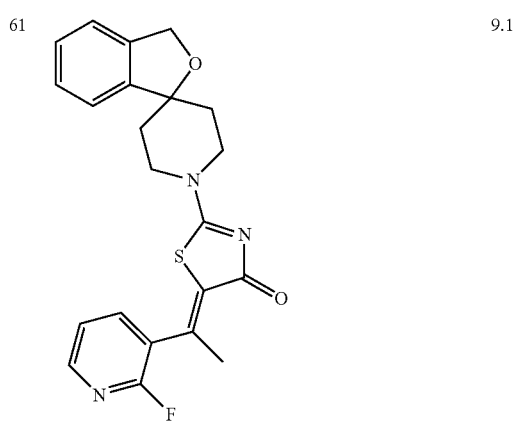 | 9.1 |
| 62 | 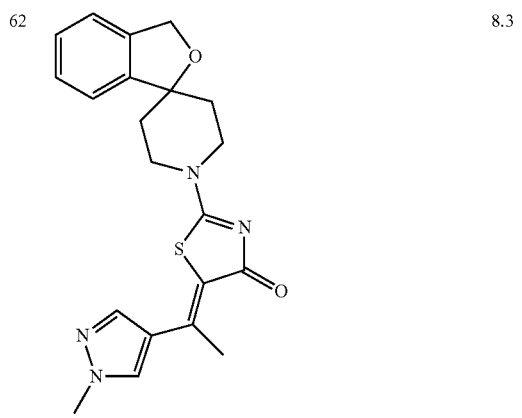 | 8.3 |
TABLE 1-continued
pKi values of selected examples
| Ex. | Structure | pK$_i$ hV$_{1a}$ |
|---|---|---|
| 63 | 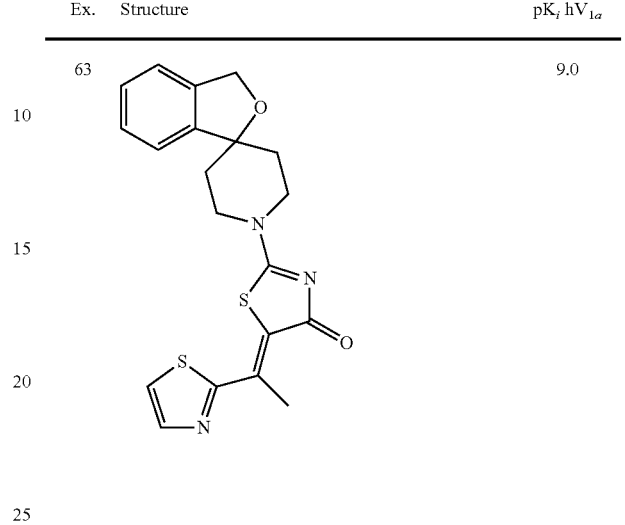 | 9.0 |
| 64 | 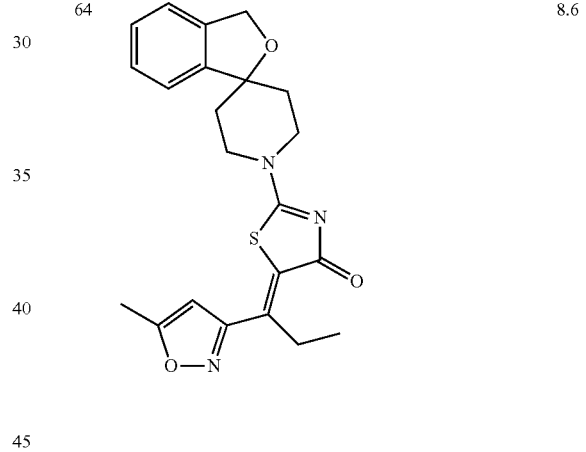 | 8.6 |
| 65 | 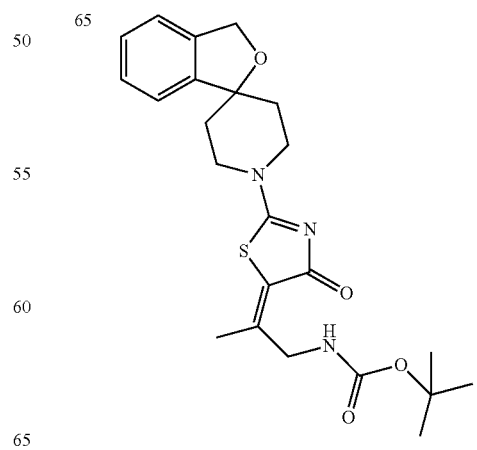 | 7.7 |

TABLE 1-continued
pKi values of selected examples
| Ex. | Structure | pK$_i$ hV$_{1a}$ |
|---|---|---|
| 66 | 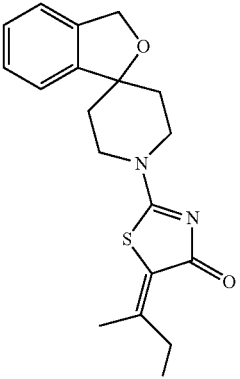 | 6.6 |
| 67 | 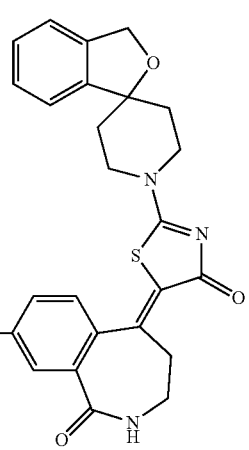 | 8.7 |
| 68 | 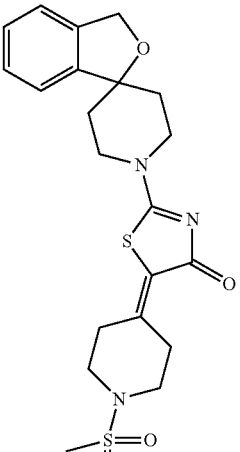 | 7.7 |
| 69 | 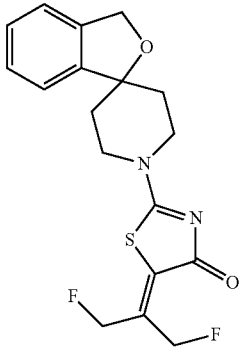 [SMILES: O=C1N=C(N2CCC3(CC2)OCc2ccccc23)SC1=C(CF)CF] | 8.0 |
| 70 | 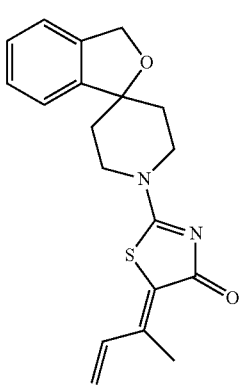 [SMILES: C=C/C(C)=C1\SC(N2CCC3(CC2)OCc2ccccc23)=NC1=O] | 7.6 |
| 71 | 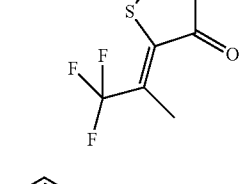 | 8.3 |
| 72 | 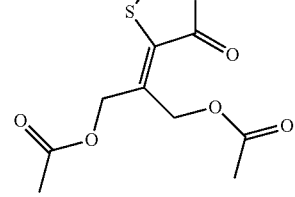 | 8.3 |

TABLE 1-continued
pKi values of selected examples
| Ex. | Structure | pK$_i$ hV$_{1a}$ |
|---|---|---|
| 73 | 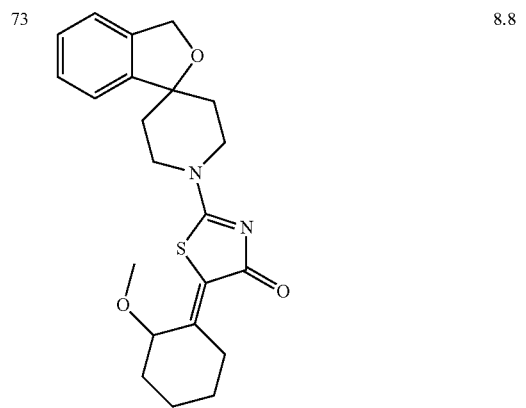 | 8.8 |
| 74 | 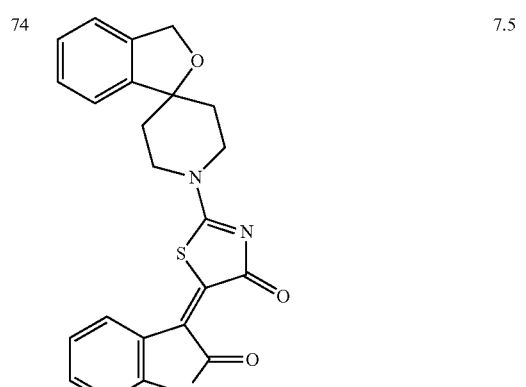 | 7.5 |
| 75 | 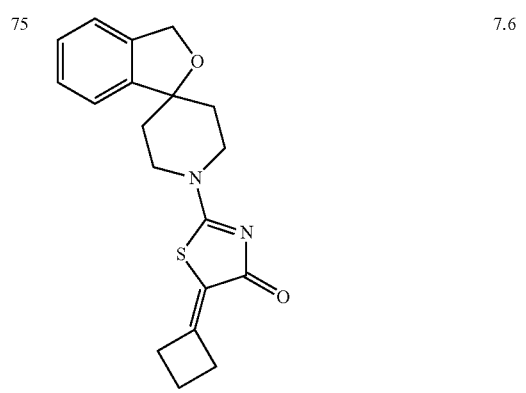 | 7.6 |
| 76 | | 7.8 |
| 77 | | 7.6 |
| 78 | | 7.9 |
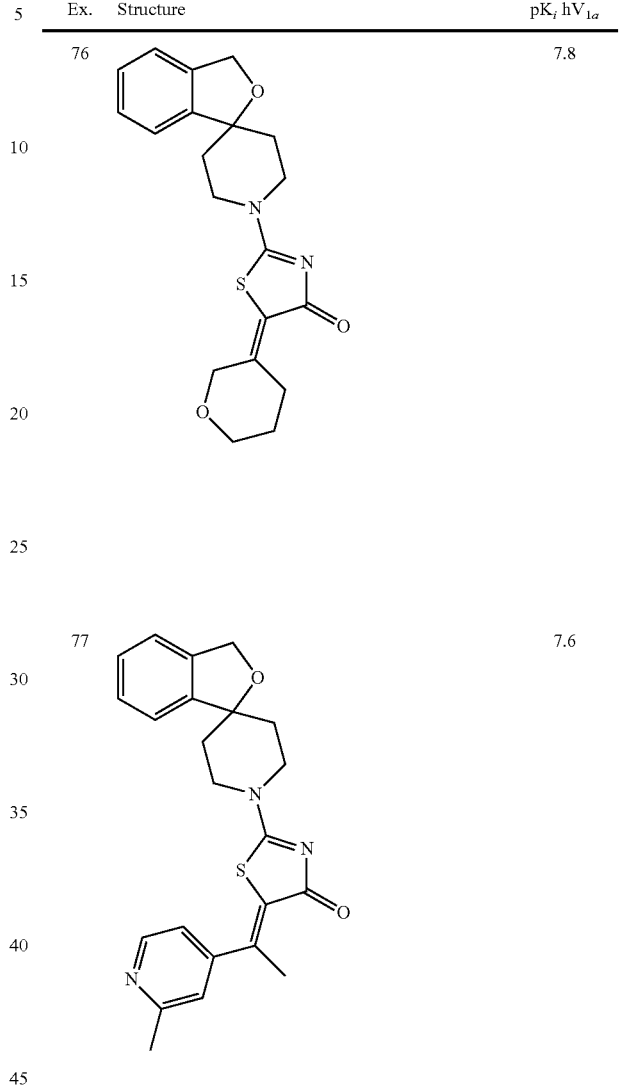
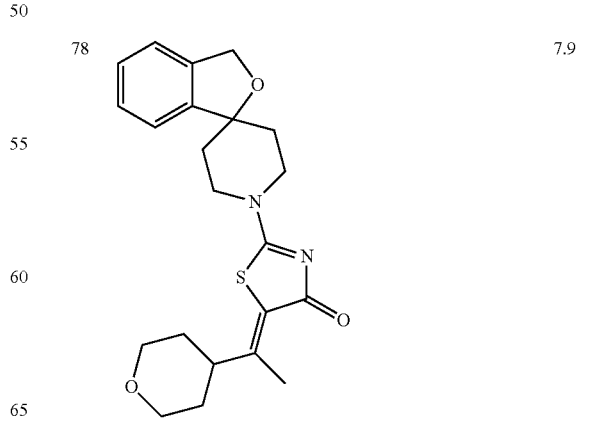

TABLE 1-continued
pKi values of selected examples
| Ex. | Structure | pK$_i$ hV$_{1a}$ |
|---|---|---|
| 79 | 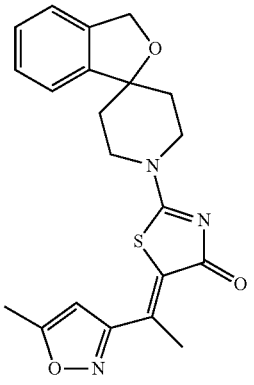 [SMILES: C/C(=C1/SC(N2CCC3(CC2)OCc2ccccc23)=NC1=O)c1cc(C)on1] | 8.4 |
| 80 | 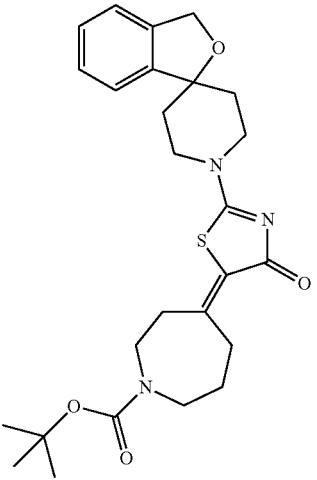 [SMILES: CC(C)(C)OC(=O)N1CCC/C(=C2/SC(N3CCC4(CC3)OCc3ccccc34)=NC2=O)CC1] | 7.1 |
| 81 | 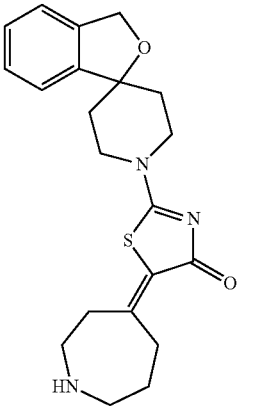 HCl | 6.9 |
| 82 | 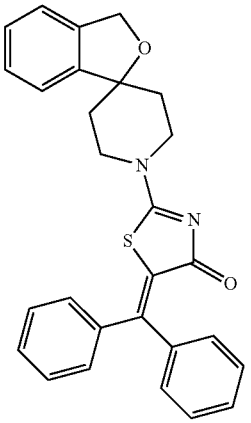 [SMILES: O=C1N=C(N2CCC3(CC2)OCc2ccccc23)SC1=C(c1ccccc1)c1ccccc1] | 8.4 |
| 83 | 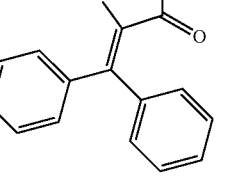 | 8.8 |
| 84 | 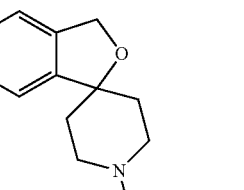 | 7.7 |

TABLE 1-continued
pKi values of selected examples
| Ex. | Structure | pK$_i$ hV$_{1a}$ |
|---|---|---|
| 85 | 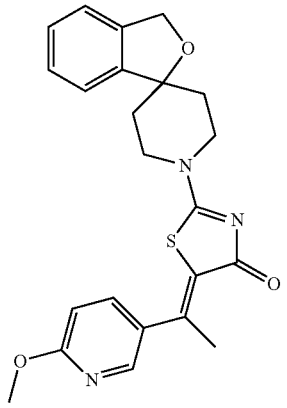 [SMILES: COc1ccc(/C(C)=C2\SC(N3CCC4(CC3)OCc3ccccc34)=NC2=O)cn1] | 8.4 |
| 86 | 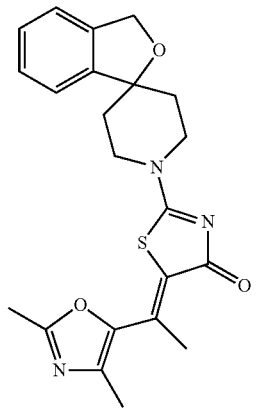 [SMILES: C/C(=C1/SC(N2CCC3(CC2)OCc2ccccc23)=NC1=O)c1oc(C)nc1C] | 8.9 |
| 87 | 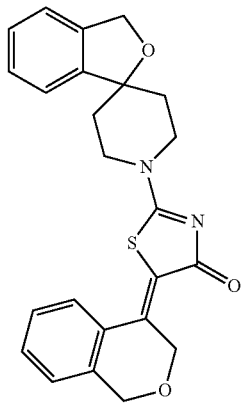 [SMILES: O=C1N=C(N2CCC3(CC2)OCc2ccccc23)S/C1=C1/COCc2ccccc21] | 8.9 |
| 88 | 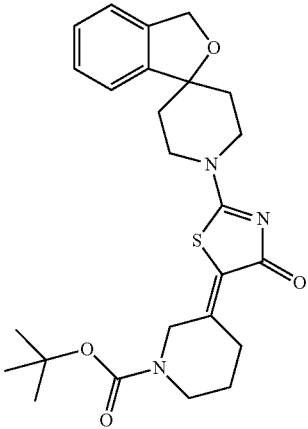 [SMILES: CC(C)(C)OC(=O)N1CCC/C(=C2/SC(N3CCC4(CC3)OCc3ccccc34)=NC2=O)C1] | 6.7 |
| 89 | 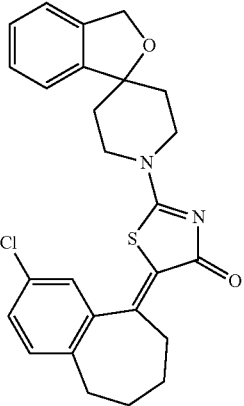 [SMILES: O=C1N=C(N2CCC3(CC2)OCc2ccccc23)S/C1=C1/CCCCc2ccc(Cl)cc21] | 9.0 |
| 90 | 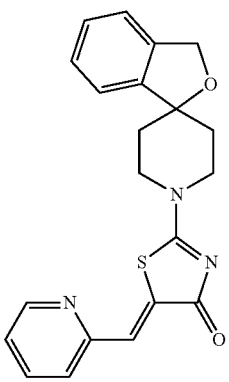 [SMILES: O=C1N=C(N2CCC3(CC2)OCc2ccccc23)S/C1=C\c1ccccn1] | 7.3 |

TABLE 1-continued pKi values of selected examples

| Ex. | Structure | pK$_i$ hV$_{1a}$ |
|---|---|---|
| 91 | 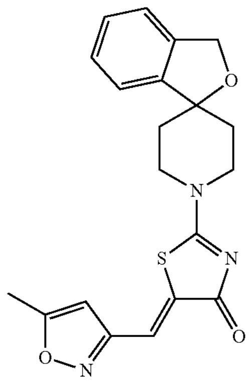 [SMILES: Cc1cc(/C=C2\SC(N3CCC4(CC3)OCc3ccccc34)=NC2=O)no1] | 7.5 |
| 92 | 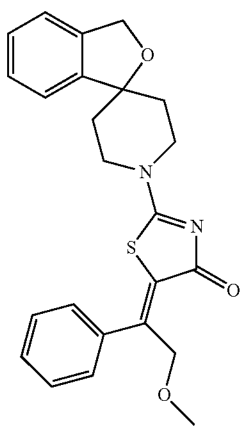 [SMILES: COC/C(=C1/SC(N2CCC3(CC2)OCc2ccccc23)=NC1=O)c1ccccc1] | 9.0 |
| 93 | 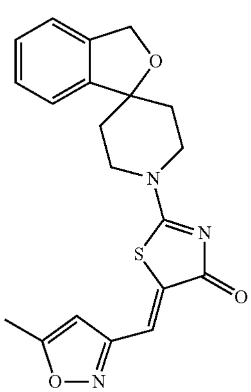 [SMILES: Cc1cc(/C=C2\SC(N3CCC4(CC3)OCc3ccccc34)=NC2=O)no1] | 8.1 |
| 94 | 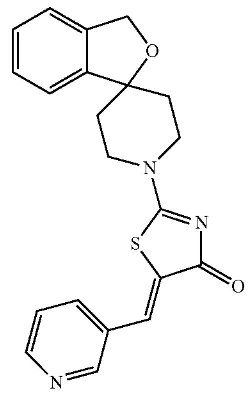 [SMILES: O=C1N=C(N2CCC3(CC2)OCc2ccccc23)S/C1=C\c1cccnc1] | 7.1 |
| 95 | 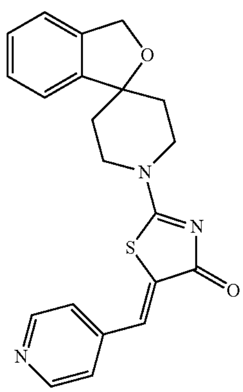 [SMILES: O=C1N=C(N2CCC3(CC2)OCc2ccccc23)S/C1=C\c1ccncc1] | 7.1 |
| 96 | 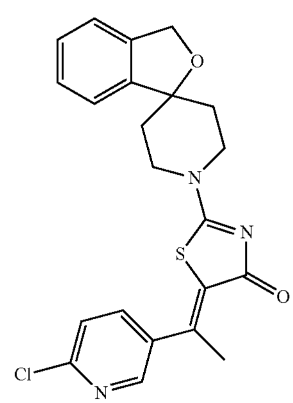 [SMILES: C/C(=C1/SC(N2CCC3(CC2)OCc2ccccc23)=NC1=O)c1ccc(Cl)nc1] | 9.4 |

TABLE 1-continued
pKi values of selected examples
| Ex. | Structure | pK$_i$ hV$_{1a}$ |
|---|---|---|
| 97 | 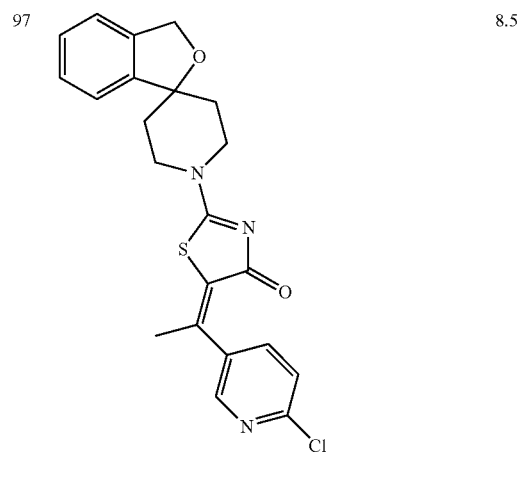 | 8.5 |
| 98 | 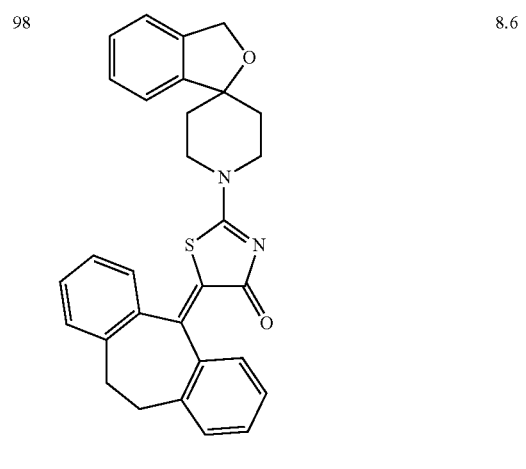 | 8.6 |
| 99 | 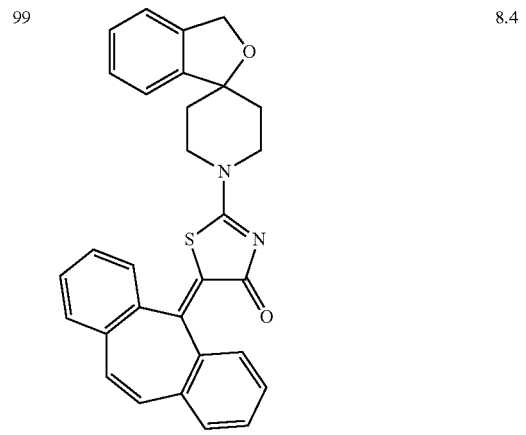 | 8.4 |
| 100 | 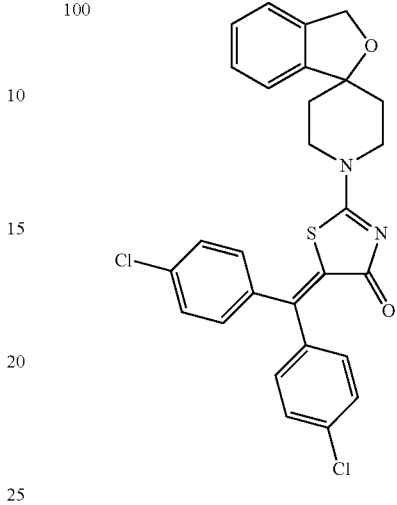 | 7.1 |
| 101 | 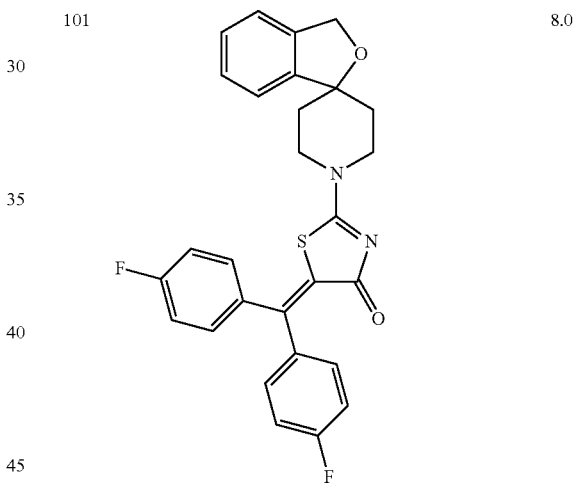 | 8.0 |
| 102 | 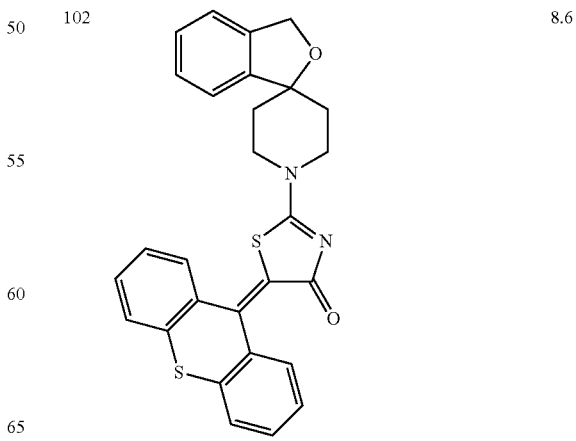 | 8.6 |

TABLE 1-continued
pKi values of selected examples
| Ex. | Structure | pK$_i$ hV$_{1a}$ |
|---|---|---|
| 103 | 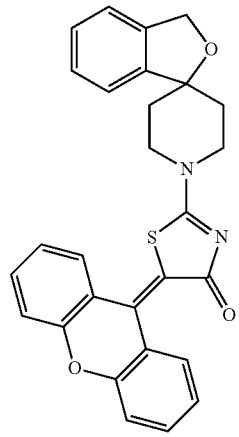 [SMILES: O=C1N=C(N2CCC3(CC2)OCc2ccccc23)SC1=C1c2ccccc2Oc2ccccc21] | 8.6 |
| 104 | 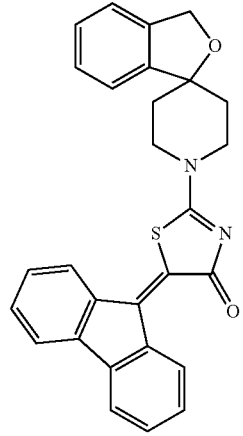 [SMILES: O=C1N=C(N2CCC3(CC2)OCc2ccccc23)SC1=C1c2ccccc2-c2ccccc21] | 8.2 |
| 105 | 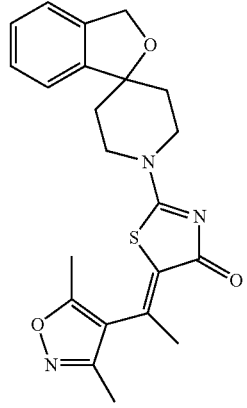 [SMILES: C/C(=C1/SC(N2CCC3(CC2)OCc2ccccc23)=NC1=O)c1c(C)noc1C] | 8.7 |
TABLE 1-continued
pKi values of selected examples
| Ex. | Structure | pK$_i$ hV$_{1a}$ |
|---|---|---|
| 106 | 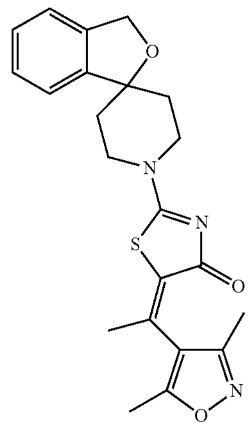 [SMILES: C/C(=C1\SC(N2CCC3(CC2)OCc2ccccc23)=NC1=O)c1c(C)noc1C] | 7.3 |
| 107 | 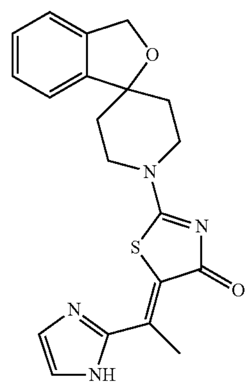 [SMILES: C/C(=C1/SC(N2CCC3(CC2)OCc2ccccc23)=NC1=O)c1ncc[nH]1] | 6.8 |
| 108 | 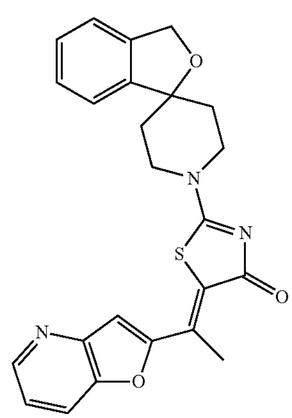 [SMILES: C/C(=C1/SC(N2CCC3(CC2)OCc2ccccc23)=NC1=O)c1cc2ncccc2o1] | 7.0 |

TABLE 1-continued
pKi values of selected examples
| Ex. | Structure | pK$_i$ hV$_{1a}$ |
|---|---|---|
| 109 | 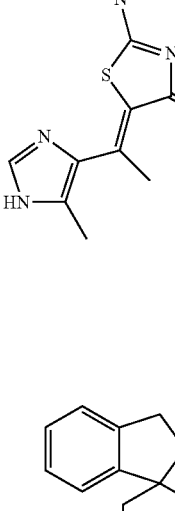 | 6.6 |
| 110 | 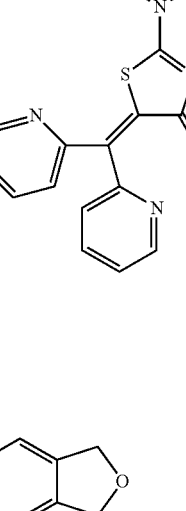 | 7.6 |
| 111 | 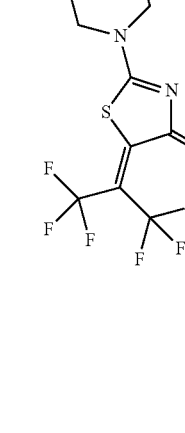 | 7.5 |
| 112 | 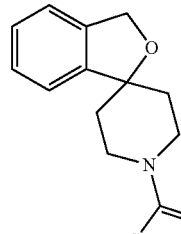 | 8.6 |
| 113 | 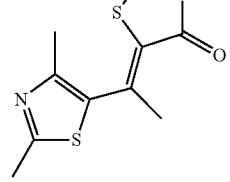 | 7.0 |
| 114 | 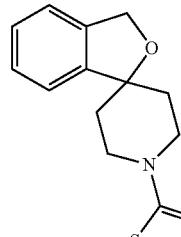 | 8.9 |
| 115 | 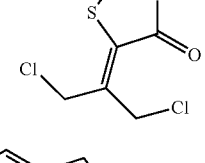 | 8.9 |

TABLE 1-continued
pKi values of selected examples
| Ex. | Structure | pK$_i$ hV$_{1a}$ |
|---|---|---|
| 116 | 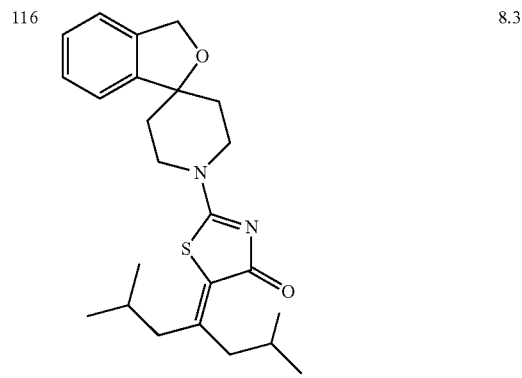 | 8.3 |
| 117 | 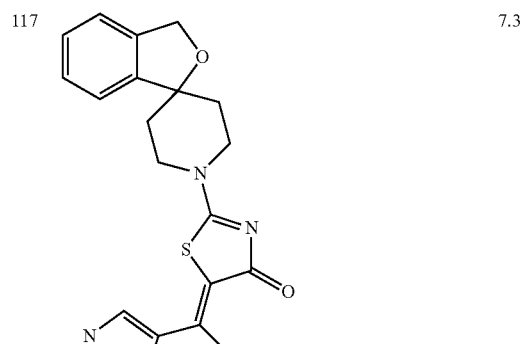 | 7.3 |
| 118 | 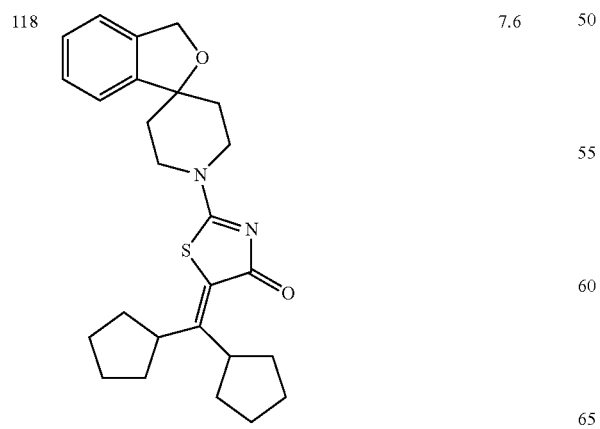 | 7.6 |
| 119 | 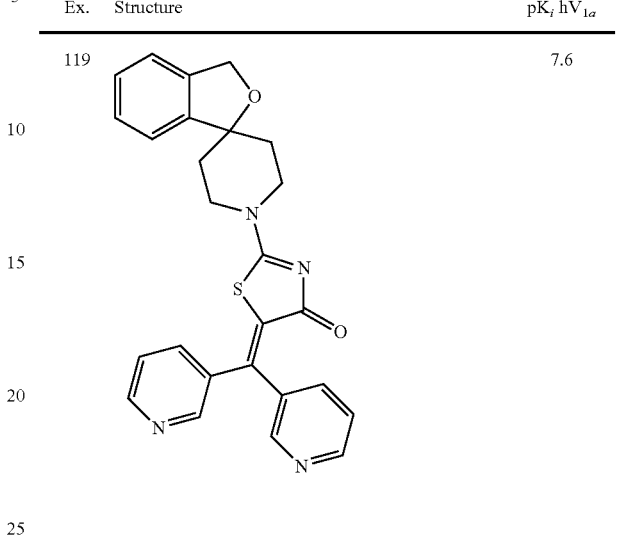 | 7.6 |
| 120 | 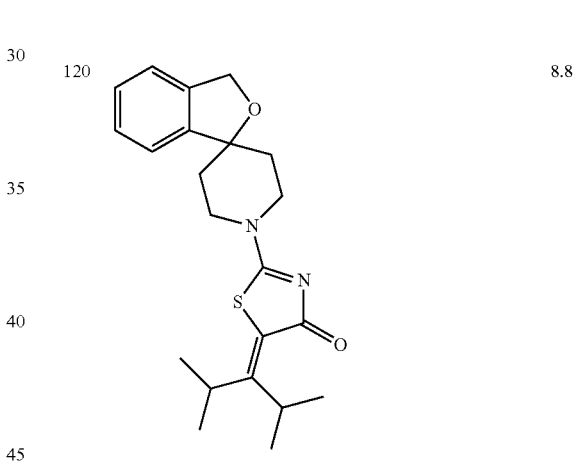 | 8.8 |
| 121 | 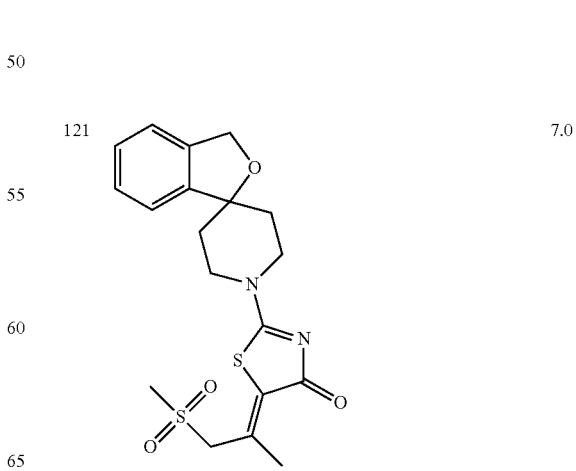 | 7.0 |

TABLE 1-continued
pKi values of selected examples
| Ex. | Structure | pK$_i$ hV$_{1a}$ |
|---|---|---|
| 122 | 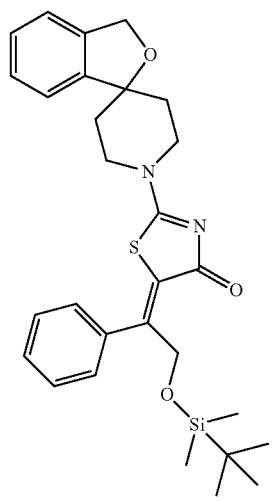 [SMILES: CC(C)(C)[Si](C)(C)OC/C(=C1/SC(N2CCC3(CC2)OCc2ccccc23)=NC1=O)c1ccccc1] | 9.0 |
| 123 | 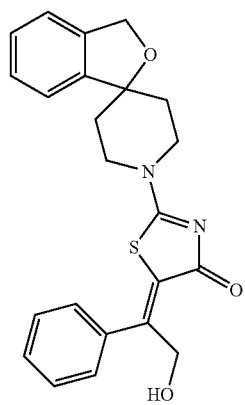 | 8.5 |
| 124 | 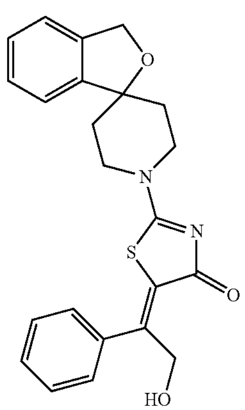 [SMILES: O=C1N=C(N2CCC3(CC2)OCc2ccccc23)S/C1=C(/CO)c1ccccc1] | 9.3 |
| 125 | 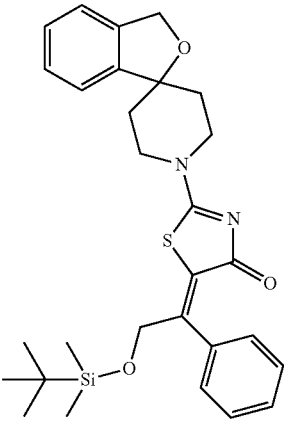 [SMILES: CC(C)(C)[Si](C)(C)OC/C(=C1\SC(N2CCC3(CC2)OCc2ccccc23)=NC1=O)c1ccccc1] | 7.2 |
| 126 | 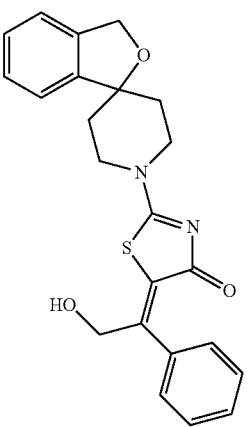 [SMILES: O=C1N=C(N2CCC3(CC2)OCc2ccccc23)S/C1=C(\CO)c1ccccc1] | |
| 127 | | 9.0 |

TABLE 1-continued
pKi values of selected examples
| Ex. | Structure | pK$_i$ hV$_{1a}$ |
|---|---|---|
| 128 | 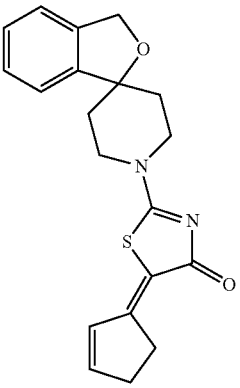 [SMILES: O=C1N=C(N2CCC3(CC2)OCc2ccccc23)S/C1=C1\C=CCC1] | 7.6 |
| 129 | 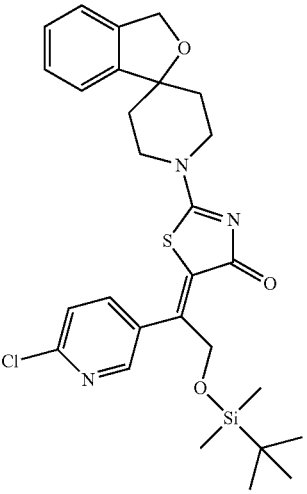 [SMILES: CC(C)(C)[Si](C)(C)OC/C(=C1/SC(N2CCC3(CC2)OCc2ccccc23)=NC1=O)c1ccc(Cl)nc1] | 8.2 |
| 130 | 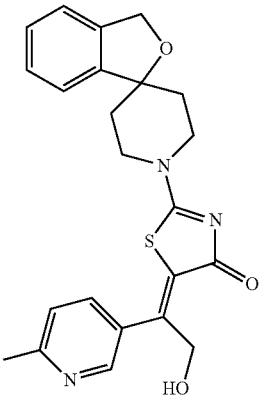 | 8.9 |
| 131 | 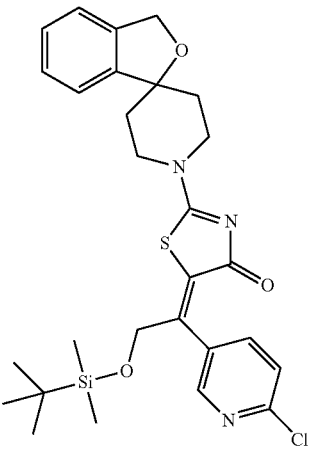 [SMILES: CC(C)(C)[Si](C)(C)OC/C(=C1\SC(N2CCC3(CC2)OCc2ccccc23)=NC1=O)c1ccc(Cl)nc1] | 7.8 |
| 132 | 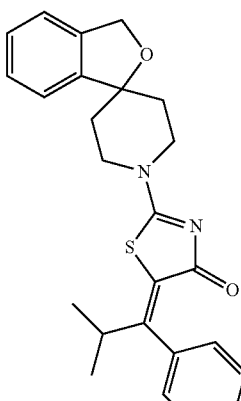 | 7.8 |
| 133 | 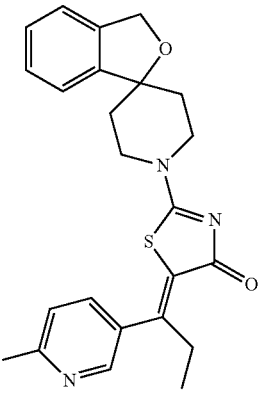 | 9.2 |

TABLE 1-continued
pKi values of selected examples
| Ex. | Structure | pK$_i$ hV$_{1a}$ |
|---|---|---|
| 134 | 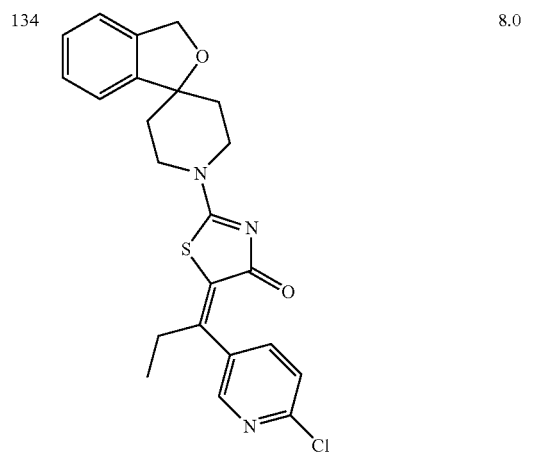 | 8.0 |
| 135 | 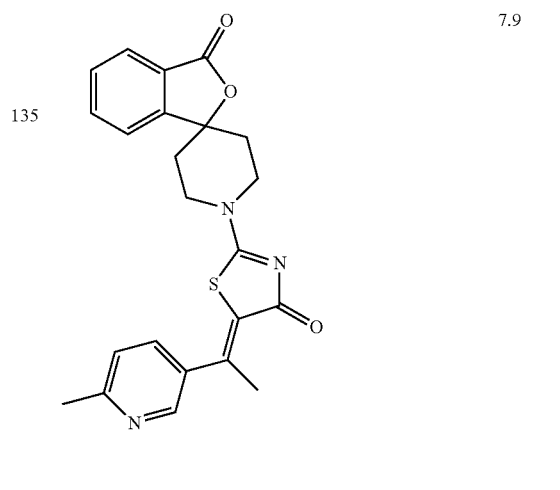 | 7.9 |
| 136 | 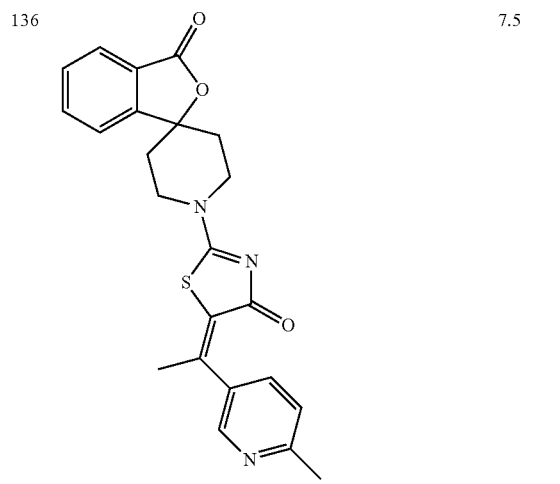 | 7.5 |
| 137 | 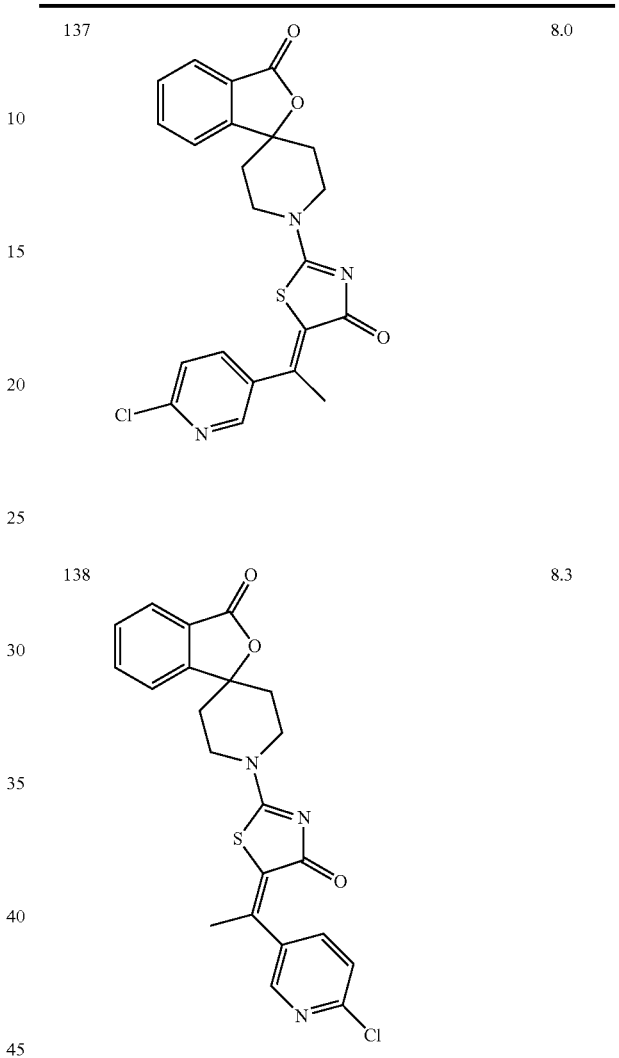 | 8.0 |
| 138 | 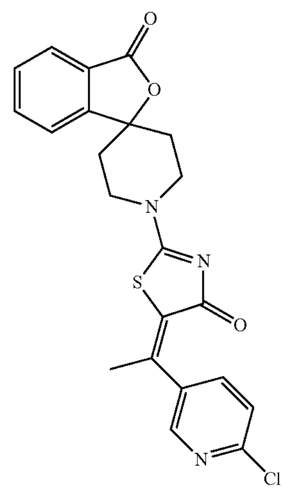 [SMILES: C/C(=C1\SC(N2CCC3(CC2)OC(=O)c2ccccc23)=NC1=O)c1ccc(Cl)nc1] | 8.3 |
| 139 | 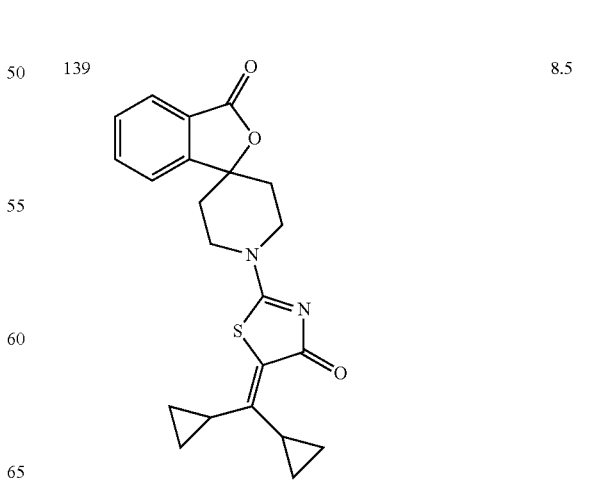 | 8.5 |

TABLE 1-continued pKi values of selected examples

| Ex. | Structure | pK$_i$ hV$_{1a}$ |
|---|---|---|
| 140 | 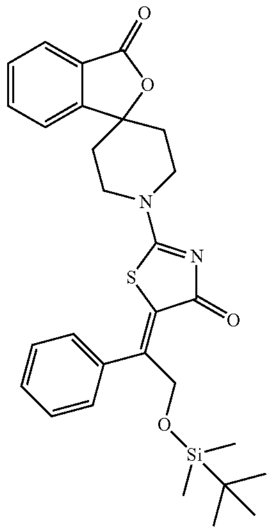 [SMILES: CC(C)(C)[Si](C)(C)OC/C(=C1/SC(N2CCC3(CC2)OC(=O)c2ccccc23)=NC1=O)c1ccccc1] | 8.9 |
| 141 | 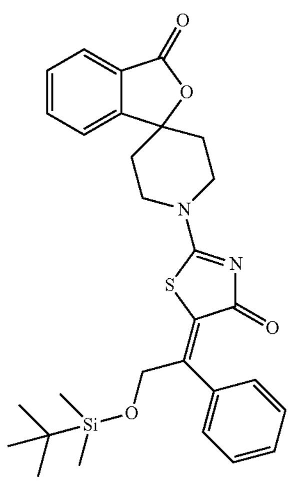 [SMILES: CC(C)(C)[Si](C)(C)OC/C(=C1\SC(N2CCC3(CC2)OC(=O)c2ccccc23)=NC1=O)c1ccccc1] | 7.6 |
| 142 | 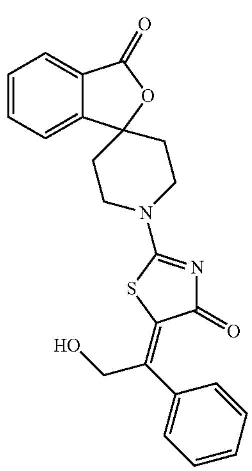 [SMILES: O=C1N=C(N2CCC3(CC2)OC(=O)c2ccccc23)S/C1=C(\CO)c1ccccc1] | 8.4 |
| 143 | 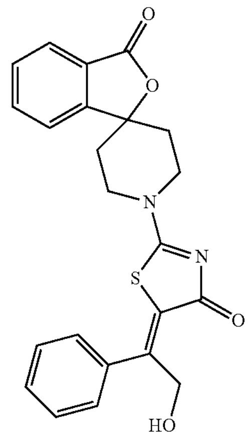 [SMILES: O=C1N=C(N2CCC3(CC2)OC(=O)c2ccccc23)S/C1=C(/CO)c1ccccc1] | 8.8 |
| 144 | 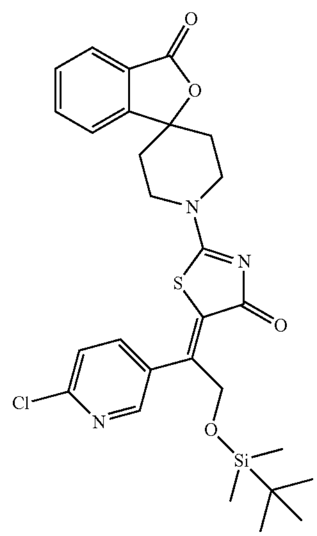 [SMILES: CC(C)(C)[Si](C)(C)OC/C(=C1/SC(N2CCC3(CC2)OC(=O)c2ccccc23)=NC1=O)c1ccc(Cl)nc1] | 8.0 |
| 145 | 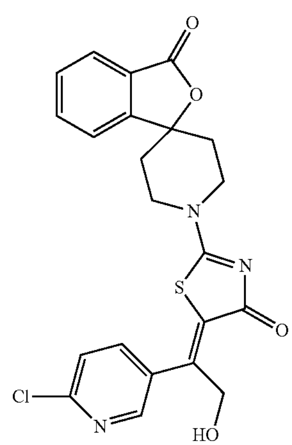 [SMILES: O=C1N=C(N2CCC3(CC2)OC(=O)c2ccccc23)S/C1=C(/CO)c1ccc(Cl)nc1] | 8.0 |

TABLE 1-continued
pKi values of selected examples
| Ex. | Structure | pK$_i$ hV$_{1a}$ |
|---|---|---|
| 146 | 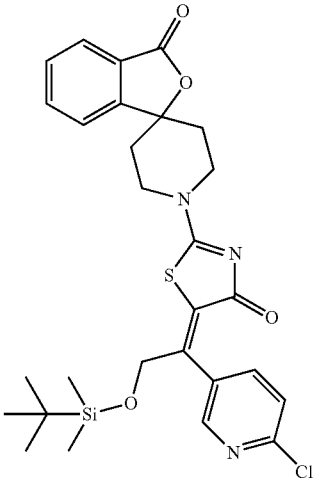 [SMILES: CC(C)(C)[Si](C)(C)OC/C(=C1\SC(N2CCC3(CC2)OC(=O)c2ccccc23)=NC1=O)c1ccc(Cl)nc1] | 7.3 |
| 147 | 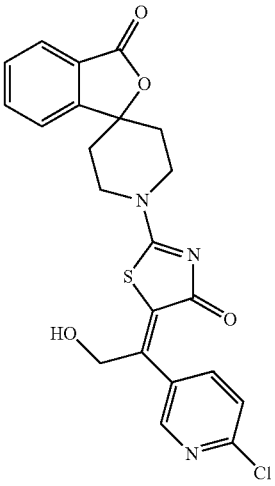 [SMILES: O=C1N=C(N2CCC3(CC2)OC(=O)c2ccccc23)S/C1=C(\CO)c1ccc(Cl)nc1] | 8.0 |
| 148 | 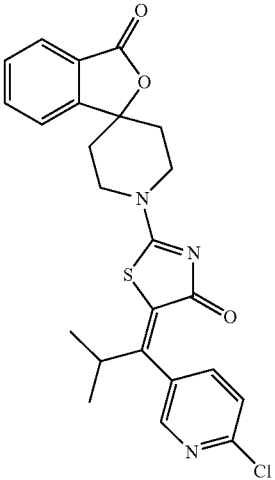 [SMILES: CC(C)/C(=C1\SC(N2CCC3(CC2)OC(=O)c2ccccc23)=NC1=O)c1ccc(Cl)nc1] | 6.8 |
| 149 | 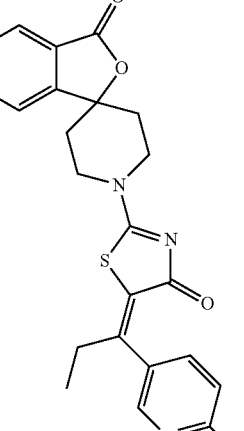 | 8.2 |
| 150 | 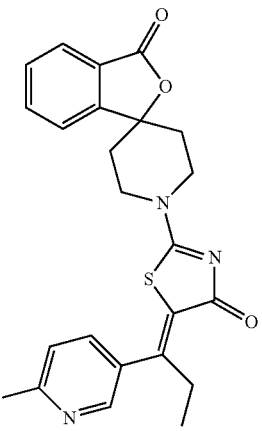 | 9.0 |
| 151 | 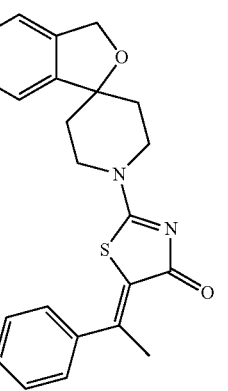 | 9.2 |

TABLE 1-continued
pKi values of selected examples
| Ex. | Structure | pK$_i$ hV$_{1a}$ |
|---|---|---|
| 152 | 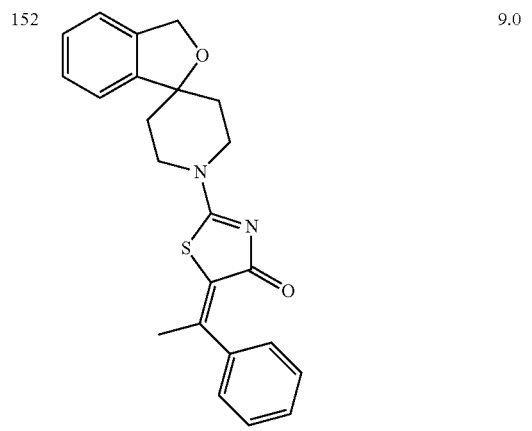 | 9.0 |
| 153 | 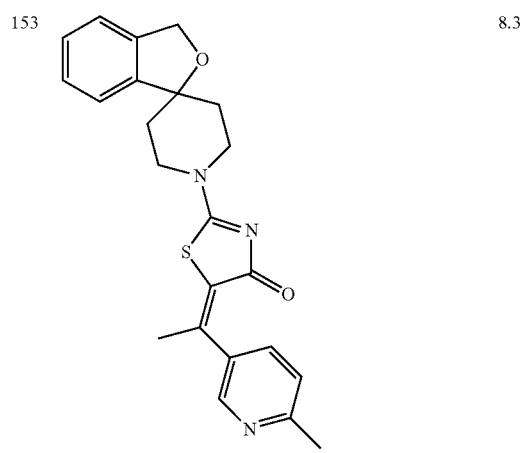 | 8.3 |
| 154 | 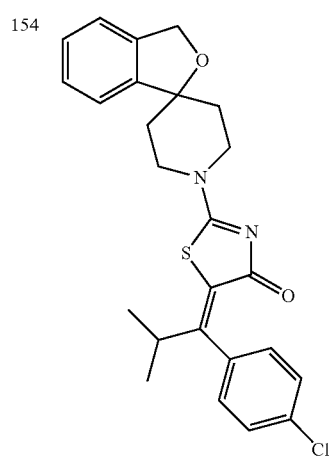 | 7.8 |
| 155 | 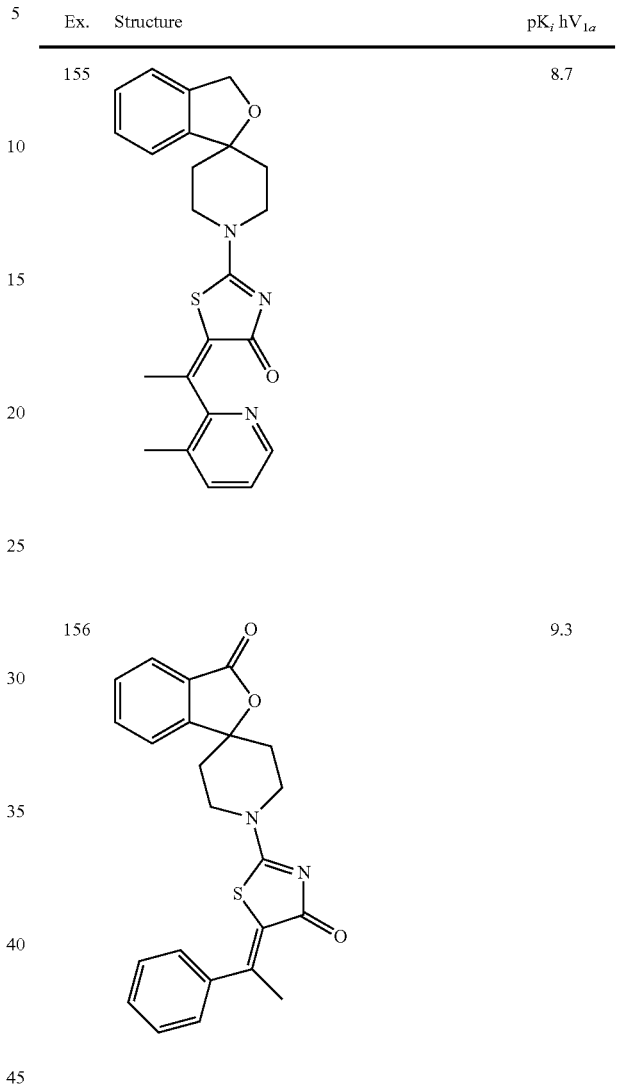 | 8.7 |
| 156 | 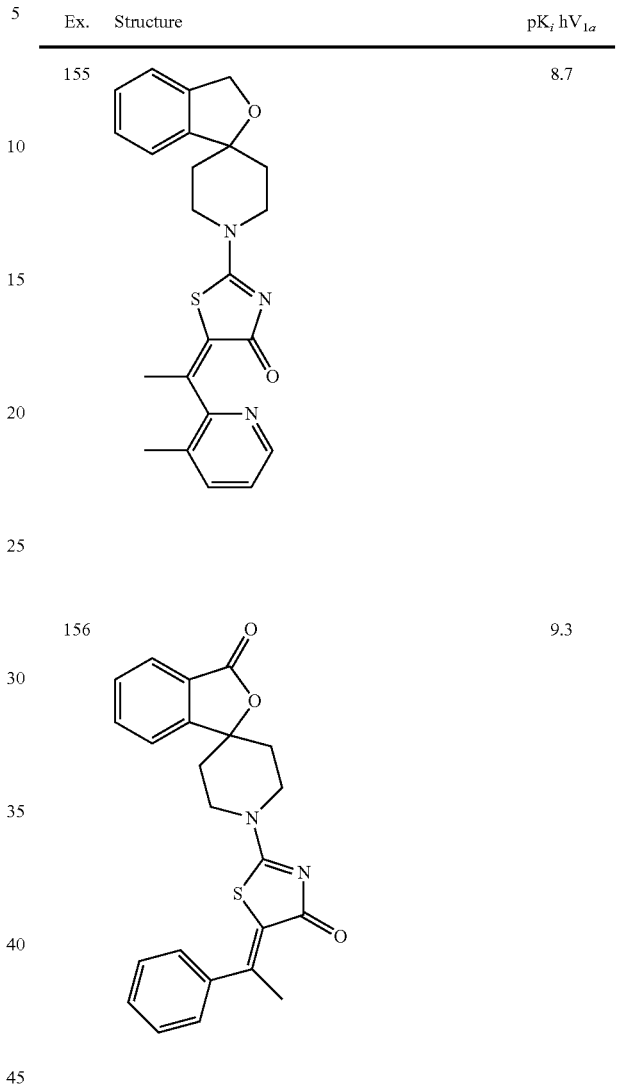 | 9.3 |
| 157 | 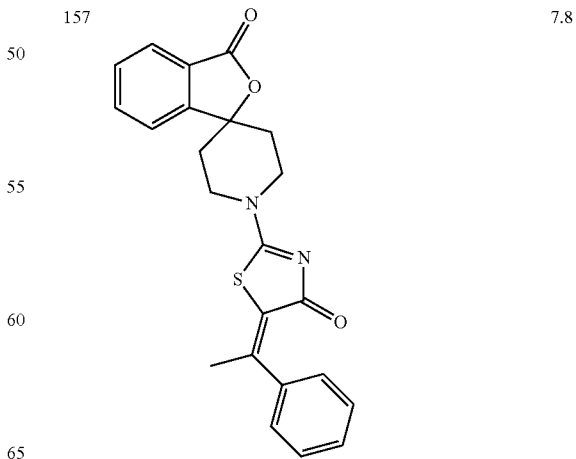 | 7.8 |

TABLE 1-continued
pKi values of selected examples
| Ex. | Structure | pK$_i$ hV$_{1a}$ |
|---|---|---|
| 158 | 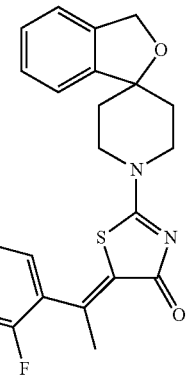 | 8.4 |
| 159 | 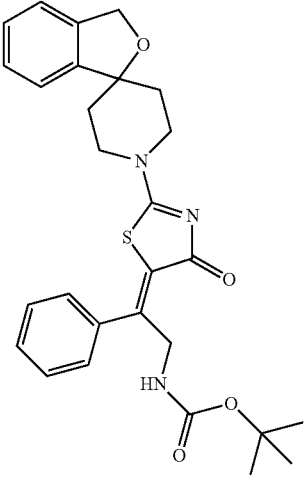 [SMILES: CC(C)(C)OC(=O)NC/C(=C1/SC(N2CCC3(CC2)OCc2ccccc23)=NC1=O)c1ccccc1] | 9.3 |
| 160 | 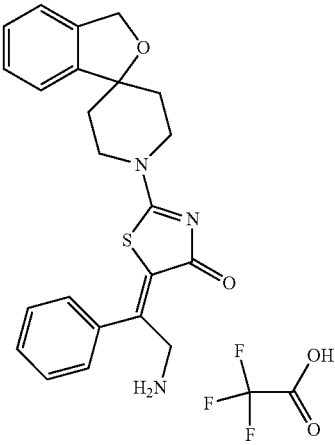 | 8.3 |
| 161 | 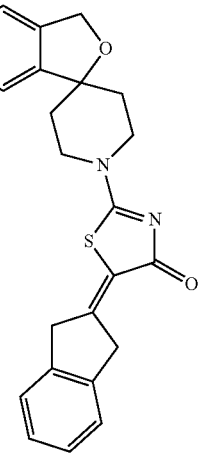 | 7.8 |
| 162 | 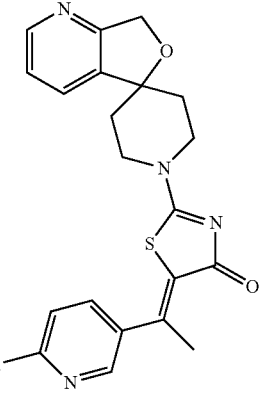 | 7.9 |
| 163 | 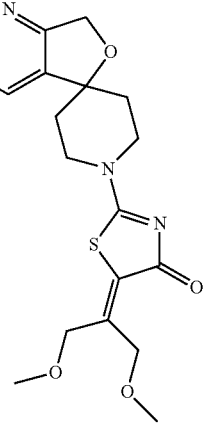 | 7.0 |

TABLE 1-continued
pKi values of selected examples
| Ex. | Structure | pK$_i$ hV$_{1a}$ |
|---|---|---|
| 164 | 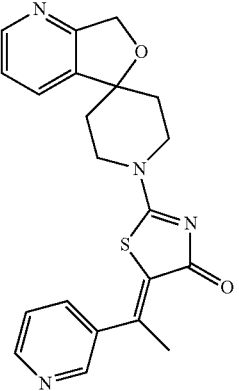 [SMILES: C/C(=C1/SC(N2CCC3(CC2)OCc2ncccc23)=NC1=O)c1cccnc1] | 6.9 |
| 165 | 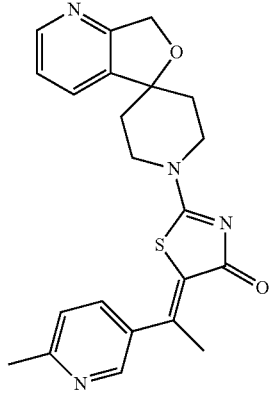 | 7.5 |
| 166 | 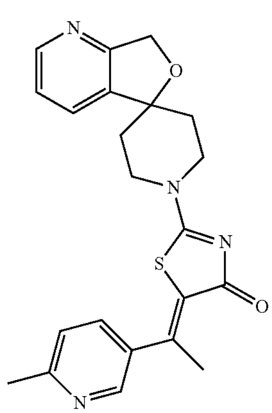 [SMILES: C/C(=C1/SC(N2CCC3(CC2)OCc2ncccc23)=NC1=O)c1ccc(C)nc1] | 7.1 |
| 167 | 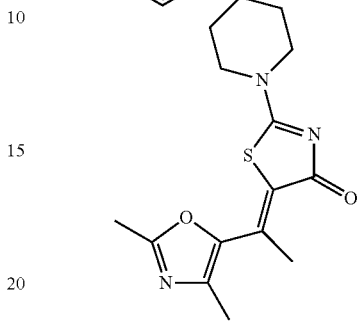 | 6.5 |
| 168 | 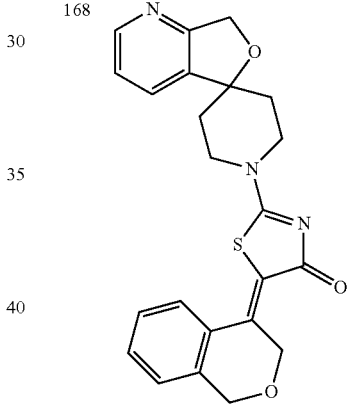 | 8.2 |
| 169 | 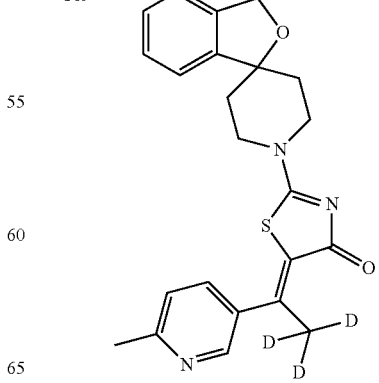 | 8.8 |

TABLE 1-continued pKi values of selected examples

| Ex. | Structure | pK$_i$ hV$_{1a}$ |
|---|---|---|
| 170 | 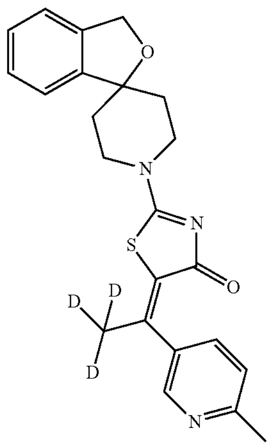 [SMILES: [2H]C([2H])([2H])/C(=C1\SC(N2CCC3(CC2)OCc2ccccc23)=NC1=O)c1ccc(C)nc1] | 8.0 |
| 171 | 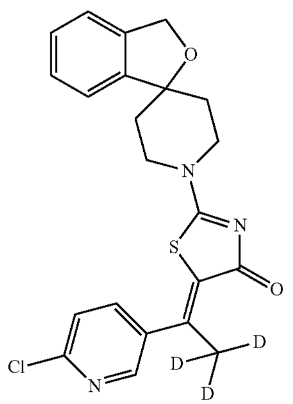 [SMILES: [2H]C([2H])([2H])/C(=C1/SC(N2CCC3(CC2)OCc2ccccc23)=NC1=O)c1ccc(Cl)nc1] | 9.3 |
| 172 | 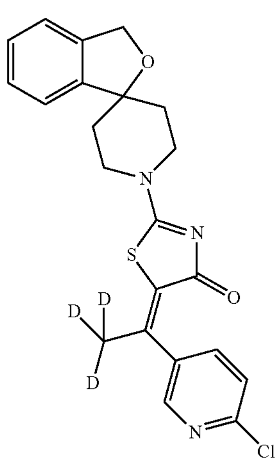 [SMILES: [2H]C([2H])([2H])/C(=C1\SC(N2CCC3(CC2)OCc2ccccc23)=NC1=O)c1ccc(Cl)nc1] | 8.9 |
| 173 | 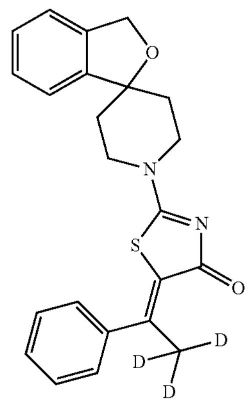 [SMILES: [2H]C([2H])([2H])/C(=C1/SC(N2CCC3(CC2)OCc2ccccc23)=NC1=O)c1ccccc1] | 8.8 |
| 174 | 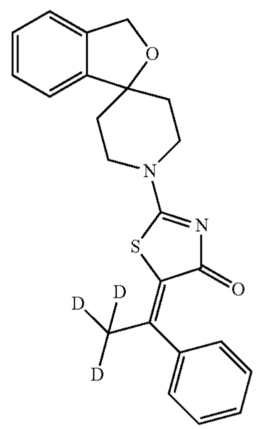 [SMILES: [2H]C([2H])([2H])/C(=C1\SC(N2CCC3(CC2)OCc2ccccc23)=NC1=O)c1ccccc1] | 8.7 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |

TABLE 3-continued possible capsule ingredient composition

| ingredient | mg/capsule | | | |
|---|---|---|---|---|
| | 5 | 25 | 100 | 500 |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Synthesis of amines of formula (II)

3'H-8-azaspiro[bicyclo[3.2.1]octane-3,1'-isobenzofuran]-3'-one a) 8-methyl-3'H-8-azaspiro[bicyclo[3.2.1]octane-3,1'-isobenzofuran]-3'-one

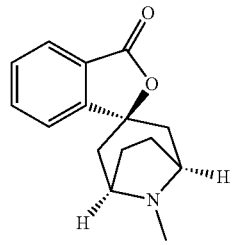 [SMILES: CN1[C@@H]2CC[C@H]1C[C@@]1(C2)OC(=O)c2ccccc21]

A solution of 2-bromobenzoic acid (10.0 g, 49.7 mmol) in tetrahydrofuran (290 ml) was cooled to −78° C. and butyllithium-solution 1.6M in hexane (62.2 ml, 99.5 mmol) was added over 30 min. The mixture was stirred at −78° C. for 1 h, then 8-methyl-8-azabicyclo[3.2.1]octan-3-one (8.3 g, 59.7 mmol) was added slowly at −78° C., stirred for 1 h at −78° C. and for 3 h at 20° C. The mixture was diluted with ethylacetate (200 ml) and water (250 ml). The aqueous phase was acidified with 25% hydrochloric acid to pH=1 and heated at 100° C. for 1 h, then basified with 4M sodium hydroxide solution to pH=12 at 20° C., extracted with dichloromethane (3×300 ml), dried over anhydrous sodium sulfate and concentrated to dryness. Purification by flash chromatography (silica gel, 100 g, 0% to 10% ethyl acetate in heptane) gave the title compound (1.6 g, 6.6 mmol, 13% yield) as an off-white solid. MS m/e: 243.3 ([M+H]+)

b) 3'H-8-azaspiro[bicyclo[3.2.1]octane-3,1'-isobenzofuran]-3'-one

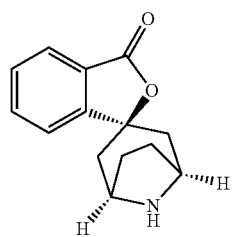 [SMILES: O=C1O[C@@]2(C[C@H]3CC[C@@H](C2)N3)c2ccccc21]

A solution of 8-methyl-3'H-8-azaspiro[bicyclo[3.2.1]octane-3,1'-isobenzofuran]-3'-one (200.0 mg, 822 μmol) in chloroform (4 ml) was dropped slowly in a stirring, boiling solution of cyanic bromide (174.0 mg, 1.64 mmol) in chloroform (4 ml). The mixture was heated to 65° C. and stirred for 6 h, then poured into 1 M hydrochloric acid solution (10 ml) and washed with water (10 ml). The organic layers were dried over anhydrous magnesium sulfate and concentrated to dryness. 25% Hydrochloric acid solution (3.5 ml) was added and the mixture refluxed for 15 h, then poured into dichloromethane (15 ml) and extracted with water (4×10 ml). The mixture was basified to pH=12 and extracted with dichloromethane (6×15 ml). The combined organic layers were dried over anhydrous magnesium sulfate and concentrated to dryness to give the title compound (99.2 mg, 46 μmol, 53% yield) as an off-white solid. MS m/e: 230.3 ([M+H]+)

Synthesis of intermediates of formula (XVI)

1-benzyl-4-(2-bromopyridin-3-yl)piperidin-4-ol

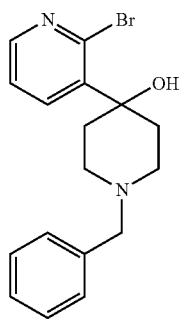 [SMILES: OC1(c2cccnc2Br)CCN(Cc2ccccc2)CC1]

To a solution of 2,3-dibromopyridine (12.0 g, 50.7 mmol) in tetrahydrofuran (250 ml) was added isopropylmagnesium chloride (26 ml, 52.0 mmol). The mixture was stirred for 30 min at 20° C. 1-benzylpiperidin-4-one (9.5 g, 50.2 mmol) was added and the mixture was stirred for 45 min, then poured into water (25 ml) and extracted with methyl tert-butyl ether (3×50 ml). The combined organic layers were dried over anhydrous sodium sulfate and concentrated to dryness. Purification by flash chromatography (amine-silica, split in 3×40 g, 0% to 50% ethyl acetate in heptane) gave the title compound (5.8 g, 16.8 mmol, 33% yield) as light brown solid.
MS m/e: 347.1 ([M+H]+)

Synthesis of intermediates of formula (XX)

1'-benzyl-7H-spiro[furo[3,4-b]pyridine-5,4'-piperidin]-7-one

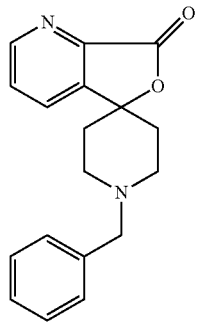 [SMILES: O=C1OC2(CCN(Cc3ccccc3)CC2)c2cccnc21]

A mixture of 1-benzyl-4-(2-bromopyridin-3-yl)piperidin-4-ol (5.30 g, 15.3 mmol), N,N-diisopropylethylamine (3.95 g, 5.33 ml, 30.5 mmol), palladium (II) acetate (0.34 g, 1.53 mmol) and triphenylphosphine (0.40 g, 1.53 mmol) in dimethylformamide (100 ml) was purged with carbon monoxide (balloon), and heated to 80° C. The reaction mixture was stirred for 12 h, poured into water (500 ml) and extracted with methyl tert-butyl ether (4×200 ml). The organic layers were dried over anhydrous sodium sulfate and concentrated to dryness. Purification by flash chromatography (amine-silica, 100 g, 0% to 100% ethyl acetate in heptane) gave the title compound (2.76 g, 9.38 mmol, 61% yield) as yellow solid. MS m/e: 295.1 ([M+H]+)

Synthesis of intermediates of formula (XVI)

1'-benzyl-7H-spiro[furo[3,4-b]pyridine-5,4'-piperidine]

a) 1'-benzyl-7H-spiro[furo[3,4-b]pyridine-5,4'-piperidine]-7-yl acetate

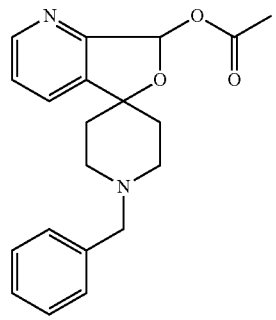 [SMILES: CC(=O)OC1OC2(CCN(Cc3ccccc3)CC2)c2cccnc21]

To a solution of 1'-benzyl-7H-spiro[furo[3,4-b]pyridine-5,4'-piperidin]-7-one (2.75 g, 9.34 mmol) in dichloromethane (90 ml) at −78° C. was added diisobutylaluminium hydride (18.70 ml, 18.7 mmol). The mixture was stirred at −78° C. for 1 hr. Pyridine (2.22 g, 2.27 ml, 28.0 mmol), then 4-dimethylaminopyridine (2.28 g, 18.7 mmol) in dichloromethane (10 ml) and finally acetic anhydride (5.72 g, 5.29 ml, 56.1 mmol) were added. The mixture was stirred at −78° C. for 15 hrs, then poured into saturated sodium bicarbonate solution (50 ml) and 1M aqueous sodium potassium tartrate solution (50 ml) and extracted with dichloromethane (3×150 ml). The combined organic layers were dried over anhydrous sodium sulfate and concentrated to dryness. Purification by flash chromatography (amine-silica, 100 g, 0% to 80% ethyl acetate in heptane) gave the title compound (2.47 g, 7.3 mmol, 78% yield) as light yellow solid. MS m/e: 339 ([M+H]+)

b) 1'-benzyl-7H-spiro[furo[3,4-b]pyridine-5,4'-piperidine]

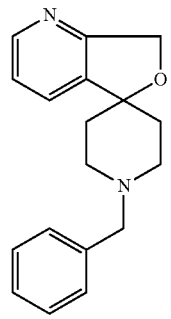 [SMILES: c1ccc(CN2CCC3(CC2)OCc2ncccc23)cc1]

A solution of 1'-benzyl-7H-spiro[furo[3,4-b]pyridine-5,4'-piperidine]-7-yl acetate (2.47 g, 7.3 mmol), triethylsilane (6.37 g, 8.74 ml, 54.7 mmol) and boron trifluoride etherate (7.77 g, 6.94 ml, 54.7 mmol) in dichloromethane (50 ml) was heated to 40° C. and stirred for 10 h. The mixture was poured into 1 M sodium hydroxide solution (100 ml) and extracted with dichloromethane (3×50 ml). The combined organic layers were dried over anhydrous sodium sulfate and concentrated to dryness. Purification by flash chromatography (amine-silica, 50 g, 0% to 100% ethyl acetate in heptane) gave the title compound (1.68 g, 6.0 mmol, 82% yield) as colorless oil. MS m/e: 281 ([M+H]+)

Synthesis of amines of formula (II)

7H-spiro[furo[3,4-b]pyridine-5,4'-piperidine]

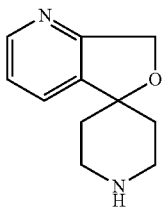 [SMILES: c1cnc2c(c1)C1(CCNCC1)OC2]

A solution of 1'-benzyl-7H-spiro[furo[3,4-b]pyridine-5,4'-piperidine] (1.68 g, 5.99 mmol) and 10% palladium on carbon (0.64 g, 0.60 mmol) in trifluoroethanol (60 ml) was stirred under hydrogen atmosphere at 22° C. for 12 hr. The reaction mixture was filtered through a pad of dicalite. The filtrate was concentrated to dryness to give the title compound (1.06 g, 5.57 mmol, 93% yield) as light yellow solid. MS m/e: 191 ([M+H]+)

Synthesis of carbonyl compounds of formula (VI)

2-chloro-5-(1-(trimethylsilyloxy)vinyl)pyridine

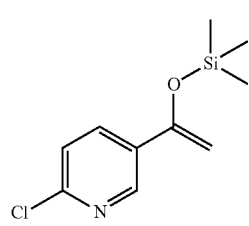

To a solution of 1-(6-chloropyridin-3-yl)ethanone (500 mg, 3.21 mmol) and N,N-diisopropylethylamine (623 mg, 842 µl, 4.82 mmol) in dichloromethane (32 ml) was added at 0° C. trimethylsilyl trifluoromethanesulfonate (857 mg, 698 µl, 3.86 mmol). The mixture was stirred for 1 h at 0-5° C., then washed with saturated sodium bicarbonate solution (2×20 ml), dried over magnesium sulfate and concentrated to dryness to give the title compound (683 mg, 2.12 mmol, 66% yield) as brown solid. MS m/e: 228.8 ([M+H]+)

1-(6-chloropyridin-3-yl)-2-hydroxyethanone

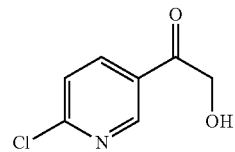 [SMILES: O=C(CO)c1ccc(Cl)nc1]

To a solution of 2-chloro-5-(1-(trimethylsilyloxy)vinyl)pyridine (300 mg, 869 µmol) in dichloromethane (9 ml) at −40° C., was added meta-chloroperoxybenzoic acid (225 mg, 1.3 mmol). The mixture was stirred at −40° C. for 2 h and at 22° C. for 14 h, then saturated sodium bicarbonate solution was added. The organic layer were separated, dried over anhydrous magnesium sulfate and concentrated to dryness. Purification by flash chromatography (silica gel, 20 g, 0% to 100% ethyl acetate in heptane) gave the title compound (80 mg, 467 µmol, 54% yield) as off-white solid. MS m/e: 172.6 ([M+H]+)

2-(tert-butyldimethylsilyloxy)-1-(6-chloropyridin-3-yl)ethanone

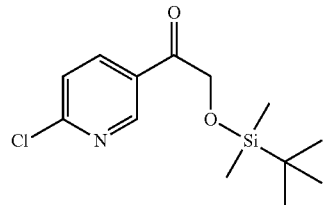 [SMILES: CC(C)(C)[Si](C)(C)OCC(=O)c1ccc(Cl)nc1]

To a solution of 1-(6-chloropyridin-3-yl)-2-hydroxyethanone (80.0 mg, 466 µmol) and imidazole (38.1 mg, 560 µmol) in dichloromethane (2.5 ml) was added tert-butyldimethylsilyl chloride (70.3 mg, 466 µmol). The mixture was stirred for 1 h at 20° C., then poured into water (5 ml) and extracted with dichloromethane (2×5 ml). The combined organic layers were dried over anhydrous magnesium sulfate and concentrated to dryness to give the title compound (121.0 mg, 424 µmol, 91% yield) as yellow solid. MS m/e: 286.8 ([M+H]+)

6-chloro-N-methoxy-N-methylnicotinamide

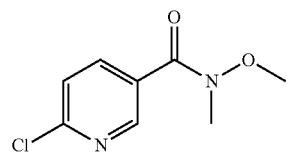

To a mixture of 6-chloronicotinoyl chloride (10.00 g, 56.8 mmol) and N,O-dimethylhydroxylamine hydrochloride (6.65 g, 68.2 mmol) in dichloromethane (180 ml) was added dropwise triethylamine (17.20 g, 23.8 ml, 170.0 mmol) at 0° C. The mixture was stirred for 1 h at 22° C., then poured into water (200 ml) and extracted with 1 M sodium hydroxide solution (2×100 ml). The combined organic layers were dried over anhydrous sodium sulfate and concentrated to dryness to give the title compound (9.31 g, 46.4 mmol, 82% yield) as yellow oil.

1-(6-chloropyridin-3-yl)-2-methylpropan-1-one

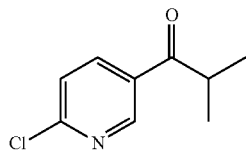

To a solution of 6-chloro-N-methoxy-N-methylnicotinamide (1.00 g, 4.98 mmol) in tetrahydrofuran (30 ml) was added isopropylmagnesium bromide (5.75 ml, 7.48 mmol) at 0° C. The mixture was stirred for 1 h, then poured into saturated sodium bicarbonate solution (50 ml) and extracted with dichloromethane (2×100 ml). The combined organic layers were dried over anhydrous sodium sulfate and concentrated to dryness. Purification by flash chromatography (silica gel, 20 g, 0% to 100% ethyl acetate in heptane) gave the title compound (97 mg, 0.53 mmol, 11% yield) as yellow oil.

1-(6-chloropyridin-3-yl)propan-1-one

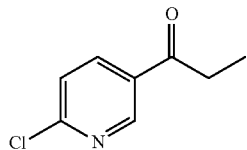

To a solution of 6-chloro-N-methoxy-N-methylnicotinamide (1.00 g, 4.98 mmol) in tetrahydrofuran (30 ml) was added ethylmagnesium bromide (1.76 ml, 5.98 mmol) at 0° C. The mixture was stirred at 0-5° C. for 1 h, then poured into saturated ammonium chloride solution (250 ml) and extracted with diethyl ether (2×50 ml). The combined organic layers were dried over anhydrous sodium sulfate and concentrated in vacuo. Purification by flash chromatography (silica gel, 20 g, 0% to 50% ethyl acetate in heptane) gave the title compound (480 mg, 2.83 mmol, 57% yield) as white powder.

2-(tert-butyldimethylsilyloxy)-1-phenylethanone

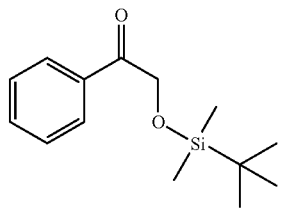 [SMILES: CC(C)(C)[Si](C)(C)OCC(=O)c1ccccc1]

To a solution of 2-hydroxy-1-phenylethanone (1.24 g, 9.11 mmol) and imidazole (0.74 g, 10.9 mmol) in dichloromethane (20 ml) was added tert-butyldimethylsilyl chloride (1.37 g, 9.11 mmol). The mixture was stirred at 22° C. for 1 h, then poured into water (100 ml) and extracted with dichloromethane (2×50 ml). The combined organic layers were dried over anhydrous sodium sulfate and concentrated to dryness. Purification by flash chromatography (silica gel, 50 g, 0% to 50% ethyl acetate in heptane) gave the title compound (2.00 g, 7.99 mmol, 88% yield) as colorless liquid.

2-(tert-butyldimethylsilyloxy)-1-(6-chloropyridin-3-yl)ethanone

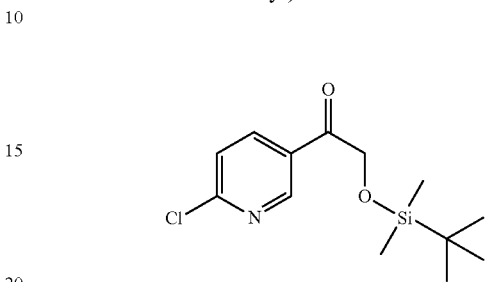

To a solution of 1-(6-chloropyridin-3-yl)-2-hydroxyethanone (80.0 mg, 466 μmol) and imidazole (38.1 mg, 560 μmol) in dichloromethane (2.5 ml) was added tert-butyldimethylsilyl chloride (70.3 mg, 466 μmol). The mixture was stirred at 22° C. for 1 h, then poured into water (5 ml) and extracted with dichloromethane (2×5 ml). The combined organic layers were dried over anhydrous sodium sulfate and concentrated to dryness to give the title compound (121.0 mg, 424 μmol, 91% yield) as yellow solid. MS m/e: 286.8 ([M+H]+)

1-(6-chloropyridin-3-yl)-2-methylpropan-1-one

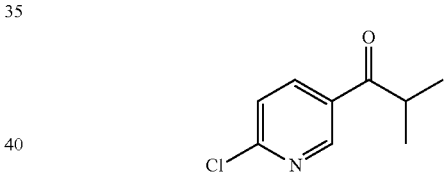

To a solution of 6-chloro-N-methoxy-N-methylnicotinamide (1.00 g, 4.98 mmol) in tetrahydrofuran (30 ml) was added isopropylmagnesium bromide (5.75 ml, 7.48 mmol) at 0° C. The mixture was stirred at 0-5° C. for 1 h, then poured into saturated sodium bicarbonate solution (50 ml) and extracted with dichloromethane (2×100 ml). The organic layers were dried over anhydrous sodium sulfate and concentrated to dryness. Purification by flash chromatography (silica gel, 20 g, 0% to 100% ethyl acetate in heptane) gave the title compound (97.0 mg, 0.53 mmol, 11% yield) as white powder.

Synthesis of intermediates of formula (VI-b)

2,2,2-trideuterio-1-(6-methylpyridin-3-yl)ethanone

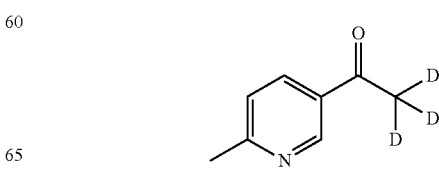

A solution of 1-(6-methylpyridin-3-yl)ethanone (550 mg, 4.07 mmol) and 2,3,4,6,7,8-hexahydro-1H-pyrimido[1,2-a]pyrimidine (57 mg, 407 µmol) in deuterated chloroform (10 ml) was stirred at 22° C. for 30 min. The reaction mixture was concentrated to dryness. The process was repeated three times to give the title compound (612 mg, 4.03 mmol, 99% yield) as light brown liquid.

1-(4-chlorophenyl)-2,2,2-trideuterioethanone

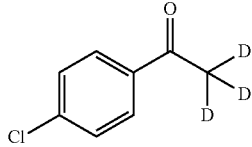 [SMILES: [2H]C([2H])([2H])C(=O)c1ccc(Cl)cc1]

A solution of 1-(4-chlorophenyl)ethanone (1.10 g, 7.12 mmol) and 2,3,4,6,7,8-hexahydro-1H-pyrimido[1,2-a]pyrimidine (0.99 g, 712 µmol) in deuterated chloroform (20 ml) was stirred at 22° C. for 30 min. The reaction mixture was concentrated to dryness. The process was repeated three times to give the title compound (1.12 g, 7.11 mmol, 100% yield) as light yellow liquid.

MS m/e: 158.4 ([M+H]+)

2,2,2-trideuterio-1-phenylethanone

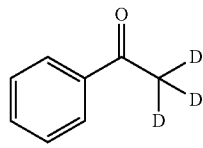 [SMILES: [2H]C([2H])([2H])C(=O)c1ccccc1]

A solution of acetophenone (1.10 g, 9.16 mmol) and 2,3,4,6,7,8-hexahydro-1H-pyrimido[1,2-a]pyrimidine (127 mg, 0.92 mmol) in deuterated chloroform (20 ml) was stirred at 22° C. for 30 min. The reaction mixture was concentrated to dryness. The process was repeated three times to give the title compound (0.95 mg, 7.7 mmol, 84% yield) as light yellow liquid.

Synthesis of thiazolones of formula (IV)

General Procedure 1:

Condensation of 2-thioxothiazolidin-4-one with carbonyl compounds

To a solution of 2-thioxothiazolidin-4-one (V) (1.0 eq) in a solvent such as acetic acid (0.3 M) or toluene (0.3 M) and a ketone or aldehyde of formula (VI), which is either commercially available or easily prepared according to methods and starting materials well known in the art (1.0 eq) is added either sodium acetate (4.0 eq) or ammonium acetate (1.0 eq). The reaction mixture is heated at 130° C. for 25 h or in a microwave reactor to 170-180° C. for 2-10 h, then concentrated to dryness. Purification by flash-chromatography gave a compound of formula (IV).

(E/Z)-5-(1-(4-chlorophenyl)ethylidene)-2-thioxothiazolidin-4-one

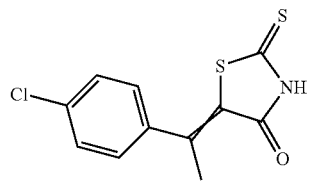 [SMILES: CC(=C1SC(=S)NC1=O)c1ccc(Cl)cc1]

To a solution of 1-(4-chlorophenyl)ethanone (7.31 g, 6.14 ml, 47.3 mmol) and 2-thioxothiazolidin-4-one (6.30 g, 47.3 mmol) in toluene (80 ml) was added ammonium acetate (3.65 g, 47.3 mmol). The reaction mixture was heated to 130° C. for 25 h, then diluted with saturated sodium bicarbonate solution (200 ml) and extracted with ethyl acetate (2×150 ml). The combined organic layers were washed with brine (saturated sodium chloride solution in water) (1×50 ml), dried over sodium sulfate and concentrated to dryness. Purification by flash-chromatography with n-heptane/ethyl acetate gave the title compound (1.57 g, 5.82 mmol, 12% yield) as yellow solid. MS m/e: 269.9 ([M+H]+)

(E/Z)-5-(1-(6-methylpyridin-3-yl)ethylidene)-2-thioxothiazolidin-4-one

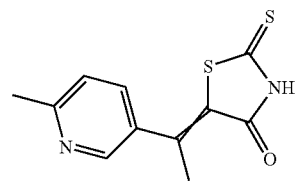 [SMILES: CC(=C1SC(=S)NC1=O)c1ccc(C)nc1]

The title compound was obtained according to the general procedure 1 from 1-(6-methylpyridin-3-yl)ethanone and 2-thioxothiazolidin-4-one and used in the subsequent step without further purification.

Synthesis of 2-sulfanyl-thiazol-4-ones of formula (III)

General Procedure 2:

Activation of 2-thioxo-thiazolidin-4-one intermediates

To a solution of a 2-thioxo-thiazolidin-4-one intermediate of formula (IV) (1.0 eq) and N,N-diisopropylethylamine (2.0 eq) in ethanol (0.3 M) is added an electrophilic reactant $R^8$-LG (wherein LG is a leaving group like halogen) which is either commercially available or easily prepared according to methods and starting materials well known in the art (2.0 eq). The reaction mixture is stirred for 12 h, diluted with saturated sodium bicarbonate solution, and then extracted with three portions of an organic solvent such as ethyl acetate or dichloromethane. The combined organic layers are washed with one portion of water and one portion of brine, dried over anhydrous sodium sulfate, filtered and concentrated to dryness. Purification by flash-chromatography gives an intermediate of formula (III).

(E/Z)-5-(1-(4-chlorophenyl)ethylidene)-2-(methylthio)thiazol-4(5H)-one

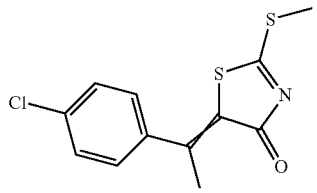 [SMILES: CSC1=NC(=O)C(=C(C)c2ccc(Cl)cc2)S1]

To a solution of (E/Z)-5-(1-(4-chlorophenyl)ethylidene)-2-thioxothiazolidin-4-one (590 mg, 2.19 mmol) and N,N-diisopropylethylamine (565 mg, 764 µl, 4.37 mmol) in ethanol (8 ml) was added methyl iodide (621 mg, 274 µl, 4.37 mmol). The reaction mixture was stirred for 12 h, diluted with saturated sodium bicarbonate solution (50 ml) and extracted with dichloromethane (3×50 ml). The combined organic layers were dried over sodium sulfate, filtered and concentrated to dryness. Purification by flash-chromatography with n-heptane/ethyl acetate gave the title compound (530 mg, 1.87 mmol, 85% yield) as off-white solid. MS m/e: 284.0 ([M+H]+)

(E/Z)-5-(1-(6-methylpyridin-3-yl)ethylidene)-2-(methylthio)thiazol-4(5H)-one

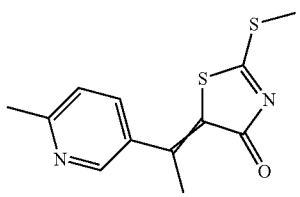

The title compound was obtained as light brown solid in 12% yield according to the general procedure 2 from (E/Z)-5-(1-(6-methylpyridin-3-yl)ethylidene)-2-thioxothiazolidin-4-one and methyl iodide. MS m/e: 265.0 ([M+H]+)

Synthesis of 2-sulfanyl-thiazol-4-ones of formula (VIII)

General Procedure 3:
Activation of 2-thiooxo-thiazolidin-4-one

To a solution of a compound of formula (V) (1.0 eq) and N,N-diisopropylethylamine (2.0 eq) in ethanol (0.3 M) is added an electrophilic reactant $R^3$-LG (wherein LG is a leaving group like halogen) which is either commercially available or easily prepared according to methods and starting materials well known in the art (2.0 eq). The reaction mixture is stirred for 12 h, diluted with saturated sodium bicarbonate solution, and then extracted with three portions of an organic solvent such as ethyl acetate or dichloromethane. The combined organic layers are washed with one portion of water and one portion of brine, dried over anhydrous sodium sulfate, filtered and concentrated to dryness. Purification by flash-chromatography gives an intermediate of formula (VIII).

Ethyl 2-(4-oxo-4,5-dihydrothiazol-2-ylthio)acetate

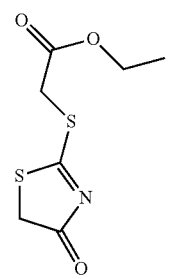

To a solution of 2-mercaptothiazol-4(5H)-one (13.2 g, 99.1 mmol) in 2-propanol (250 ml) was added triethylamine (10.0 g, 13.7 ml, 99.1 mmol). The reaction mixture was heated to 85° C. and stirred for 2 h, then concentrated to dryness. The residue was suspended in acetone (250 ml). Ethyl 2-chloroacetate (12.1 g, 10.6 ml, 99.1 mmol) was added, and the reaction was heated to 85° C. for 3 h, then filtered, and concentrated to dryness. Purification by flash chromatography (silica gel, 450 g, 20% to 60% ethyl acetate in hexanes) gave the title compound (13.1 g, 59.7 mmol, 60% yield) as light yellow solid. MS m/e: 220.0 [(M+H)+]

Synthesis of 2-amino-thiazol-4-ones of formula (VII)

General Procedure 4:
Aminolysis of 2-sulfanyl-thiazolo-4-ones

To a suspension of a secondary amine of formula (II) (1.0 eq) or its hydrochloride salt and a 2-sulfanyl-thiazol-4-one of formula (VIII) (1.0 eq) in ethanol (0.07-0.11 M), N,N-diisopropylethylamine (1.2-2.0 eq) is added. The reaction mixture is heated either in a microwave reactor at 120° C. for 5-10 min or under conventional heating at 90° C. for 12 h. The reaction mixture is concentrated to dryness. Purification by flash-chromatography gives a compound of formula (VII).

2-(3H-spiro[isobenzofuran-1,4'-piperidine]-1'-yl)thiazol-4(5H)-one

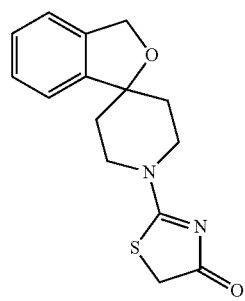 [SMILES: O=C1CSC(N2CCC3(CC2)OCc2ccccc23)=N1]

A solution of 3H-spiro[isobenzofuran-1,4'-piperidine] (4.00 g, 21.1 mmol) and ethyl 2-(4-oxo-4,5-dihydrothiazol-2-ylthio)acetate (4.63 g, 21.1 mmol) in 2-propanol (36 ml) was heated to 85° C. and stirred for 1.5 h. The reaction mixture was concentrated, whereas the product crystallizes. Filtration of the solid, washing with 2-propanol and drying gave the title compound (5.38 g, 18.7 mmol, 88% yield) as off-white solid. MS m/e: 289.1 [(M+H)+]

1'-(4-oxo-4,5-dihydrothiazol-2-yl)-3H-spiro[isobenzofuran-1,4'-piperidin]-3-one

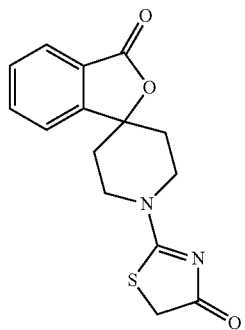 [SMILES: O=C1CSC(N2CCC3(CC2)OC(=O)c2ccccc23)=N1]

The title compound was obtained as off-white solid in 96% yield according to the general procedure 4 from 3H-spiro[isobenzofuran-1,4'-piperidin]-3-one and ethyl 2-(4-oxo-4,5-dihydrothiazol-2-ylthio)acetate. MS m/e: 303.5 ([M+H]+)

2-(7H-spiro[furo[3,4-b]pyridine-5,4'-piperidine]-1'-yl)thiazol-4(5H)-one

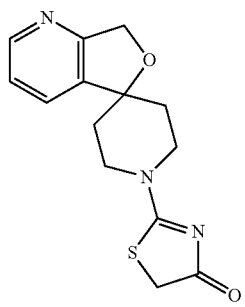 [SMILES: O=C1CSC(N2CCC3(CC2)OCc2ncccc23)=N1]

The title compound was obtained as light yellow solid in 62% yield according to the general procedure 4 from ethyl 2-(4-oxo-4,5-dihydrothiazol-2-ylthio)acetate and 7H-spiro[furo[3,4-b]pyridine-5,4'-piperidine]. MS m/e: 290.1 ([M+H]+)

General Procedure 5:
Aminolysis of 2-sulfanyl-thazolo-4-ones

To a suspension of a secondary amine of formula (II) (1.0 eq) or its hydrochloride salt and a 2-sulfanyl-thiazol-4-one of formula (III) (1.0 eq) in ethanol (0.07-0.11 M), N,N-diisopropylethylamine (1.2-2.0 eq) is added. The reaction mixture is heated to reflux by conventional heating or in a microwave reactor to 120° C. and stirred for 5-10 min. The reaction mixture is concentrated to dryness. Purification by flash-chromatography gives an compound of formula (I).

General Procedure 6:
Condensation of 2-aminothiazol-4-ones with Carbonyl Compounds in the Presence of TiCl4

To a suspension of a 2-aminothiazol-4-one of formula (VII) (1.0 eq) and a ketone or aldehyde of formula (VI), which is either commercially available or easily prepared according to methods and starting materials well known in the art (1.0-1.5 eq) in dichloromethane (0.18-0.29 M) is added titanium(IV) chloride (1 M in dichloromethane, 1.4-2.3 eq) and pyridine (10.0 eq). The reaction mixture is either stirred at 22-40° C. for 5 min-12 h or heated in a microwave reactor to 100° C. and stirred for 10-20 min. The reaction mixture is then diluted with water and extracted with three portions of dichloromethane. The combined organic layers are washed with one portion of brine, dried over anhydrous sodium sulfate and concentrated to dryness. Purification by flash-chromatography gives a compound of formula (I).

General Procedure 7:
Condensation of 2-aminothiazol-4-ones with Carbonyls in the Presence of Acetate To a solution of a 2-aminothiazol-4-one of formula (VII) (1.0 eq) in a solvent such as acetic acid (0.3 M) or toluene (0.3 M) and a ketone or aldehyde of formula (VI) which is either commercially available or easily prepared according to methods and starting materials well known in the art (1.0 eq) is added either sodium acetate (4.0 eq) or ammonium acetate (1.0 eq). The reaction mixture is heated at 130° C. for 25 h or in a microwave reactor to 170-180° C. for 2-10 h, then concentrated to dryness. Purification by flash-chromatography gives a compound of formula (I).

Example 1

(5E/Z)-5-[1-(4-chlorophenyl)ethylidene]-2-(1'H,3H-spiro[2-benzofuran-1,4'-piperidin]-1'-yl)-1,3-thiazol-4(5H)-one The title compound was obtained as off-white solid in 85% yield according to the general procedure 5 from (E/Z)-5-(1-(4-chlorophenyl)ethylidene)-2-(methylthio)thiazol-4(5H)-one and 3H-spiro[isobenzofuran-1,4'-piperidine]. MS m/e: 425.1 ([M+H]+)

Example 2

(5E/Z)-5-[1-(4-chlorophenyl)ethylidene]-2-(1'H,5H-spiro[furo[3,4-b]pyridine-7,4'-piperidin]-1'-yl)-1,3-thiazol-4(5H)-one The title compound was obtained as colorless oil in 92% yield according to the general procedure 5 from (E/Z)-5-(1-(4-chlorophenyl)ethylidene)-2-(methylthio)thiazol-4(5H)-one and 5H-spiro[furo[3,4-b]pyridine-7,4'-piperidine]. MS m/e: 426.1 ([M+H]+)

Example 3

1'-{(5E/Z)-5-[1-(4-chlorophenyl)ethylidene]-4-oxo-4,5-dihydro-1,3-thiazol-2-yl}-3H-spiro[2-benzofuran-1,4'-piperidin]-3-one The title compound was obtained as off-white solid in 73% yield according to the general procedure 5 from (E/Z)-5-(1-(4-chlorophenyl)ethylidene)-2-(methylthio)thiazol-4(5H)-one and 3H-spiro[isobenzofuran-1,4'-piperidin]-3-one. MS m/e: 439.3 ([M+H]+)

Example 4

(5E/Z)-5-[1-(4-chlorophenyl)ethylidene]-2-(1H,1'H-spiro[furo[3,4-c]pyridin-3,4'-piperidin]-1'-yl)-1,3-thiazol-4(5H)-one and (5Z)-5-[1-(4-chlorophenyl)ethylidene]-2-(1H,1'H-spiro[furo[3,4-c]pyridin-3,4'-piperidin]-1'-yl)-1,3-thiazol-4(5H)-one The title compound was obtained as off-white solid in 45% yield according to the general procedure 5 from (E/Z)-

5-(1-(4-chlorophenyl)ethylidene)-2-(methylthio)thiazol-4 (5H)-one and 1H-spiro[furo[3,4-c]pyridine-3,4'-piperidine]. MS m/e: 426.4 ([M+H]+)

Example 5

8-{(5E/Z)-5-[1-(4-chlorophenyl)ethylidene]-4-oxo-4, 5-dihydro-1,3-thiazol-2-yl}-3'H-spiro[8-azabicyclo [3.2.1]octane-3,1'-[2]benzofuran]-3'-one The title compound was obtained as off-white solid in 38% yield according to the general procedure 5 from (E/Z)-5-(1-(4-chlorophenyl)ethylidene)-2-(methylthio)thiazol-4 (5H)-one and 3'H-8-azaspiro[bicyclo[3.2.1]octane-3,1'-isobenzofuran]-3'-one. MS m/e: 465.4 ([M+H]+)

Example 6

(5E/Z)-5-[1-(4-chlorophenyl)ethylidene]-2-(1'H,7H-spiro[furo[3,4-b]pyridine-5,4'-piperidin]-1'-yl)-1,3-thiazol-4(5H)-one The title compound was obtained as white solid in 98% yield according to the general procedure 5 from (E/Z)-5-(1-(4-chlorophenyl)ethylidene)-2-(methylthio)thiazol-4(5H)-one and 7H-spiro[furo[3,4-b]pyridine-5,4'-piperidine]. MS m/e: 426.1 ([M+H]+)

Example 7

(5E/Z)-5-[1-(6-methylpyridin-3-yl)ethylidene]-2-(1'H,3H-spiro[2-benzofuran-1,4'-piperidin]-1'-yl)-1, 3-thiazol-4(5H)-one The title compound was obtained as orange gum in 29% yield according to the general procedure 5 from (E/Z)-5-(1-(6-methylpyridin-3-yl)ethylidene)-2-(methylthio)thiazol-4 (5H)-one and 3H-spiro[isobenzofuran-1,4'-piperidine]. MS m/e: 406.3 ([M+H]+)

Example 8

(5Z)-5-(4-chlorobenzylidene)-2-(1'H,3H-spiro[2-benzofuran-1,4'-piperidin]-1'-yl)-1,3-thiazol-4(5H)-one A suspension of 4-chlorobenzaldehyde (9.8 mg, 69.4 µmol), 2-(3H-spiro[isobenzofuran-1,4'-piperidine]-1'-yl)thiazol-4(5H)-one (20.0 mg, 69.4 µmol) and sodium acetate (22.8 mg, 277 µmol) in acetic acid (200 µl) was heated in the microwave at 170° C. and stirred for 2 h. The reaction mixture was concentrated to dryness. Purification by flash-chromatography with n-heptane/ethyl acetate gave the title compound (8.8 mg, 21.4 µmol, 31% yield) as white solid. MS m/e: 411.1 ([M+H]+)

Example 9

(5Z)-5-benzylidene-2-(1'H,3H-spiro[2-benzofuran-1, 4'-piperidin]-1'-yl)-1,3-thiazol-4(5H)-one The title compound was obtained as white solid in 55% yield according to the general procedure 7 from 2-(3H-spiro [isobenzofuran-1,4'-piperidine]-1'-yl)thiazol-4(5H)-one and benzaldehyde. MS m/e: 377.4 ([M+H]+)

Example 10

(5E/Z)-5-(5-chloro-2,3-dihydro-1H-inden-1-ylidene)-2-(1'H,3H-spiro[2-benzofuran-1,4'-piperidin]-1'-yl)-1,3-thiazol-4(5H)-one The title compound was obtained as white solid in 10% yield according to the general procedure 7 from 2-(3H-spiro [isobenzofuran-1,4'-piperidine]-1'-yl)thiazol-4(5H)-one and 5-chloro-2,3-dihydro-1H-inden-1-one. MS m/e: 437.1 ([M+H]+)

Example 11

(5E/Z)-5-(6-chloro-3,4-dihydronaphthalen-1(2H)-ylidene)-2-(1'H,3H-spiro[2-benzofuran-1,4'-piperidin]-1'-yl)-1,3-thiazol-4(5H)-one The title compound was obtained as white solid in 5% yield according to the general procedure 7 from 2-(3H-spiro [isobenzofuran-1,4'-piperidine]-1'-yl)thiazol-4(5H)-one and 6-chloro-3,4-dihydronaphthalen-1(2H)-one. MS m/e: 451.1 ([M+H]+)

Example 12

(5E/Z)-5-[1-(3-chlorophenyl)ethylidene]-2-(1'H,3H-spiro[2-benzofuran-1,4'-piperidin]-1'-yl)-1,3-thiazol-4(5H)-one The title compound was obtained as off-white solid in 12% yield according to the general procedure 7 from 2-(3H-spiro[isobenzofuran-1,4'-piperidine]-1'-yl)thiazol-4(5H)-one and 1-(3-chlorophenyl)ethanone. MS m/e: 425.1 ([M+H]+)

Example 13

(5E/Z)-5-[1-(4-chlorophenyl)propylidene]-2-(1'H, 3H-spiro[2-benzofuran-1,4'-piperidin]-1'-yl)-1,3-thiazol-4(5H)-one The title compound was obtained as light brown oil in 1% yield according to the general procedure 7 from 2-(3H-spiro [isobenzofuran-1,4'-piperidine]-1'-yl)thiazol-4(5H)-one and 1-(4-chlorophenyl)propan-1-one. MS m/e: 439.1 ([M+H]+)

Example 14

(5E/Z)-5-[1-(2-chlorophenyl)ethylidene]-2-(1'H,3H-spiro[2-benzofuran-1,4'-piperidin]-1'-yl)-1,3-thiazol-4(5H)-one The title compound was obtained as white solid in 3% yield according to the general procedure 7 from 2-(3H-spiro [isobenzofuran-1,4'-piperidine]-1'-yl)thiazol-4(5H)-one and 1-(2-chlorophenyl)ethanone. MS m/e: 425.1 ([M+H]+)

Example 15

5-(1,3-dimethoxypropan-2-ylidene)-2-(1'H,3H-spiro[2-benzofuran-1,4'-piperidin]-1'-yl)-1,3-thiazol-4(5H)-one To a suspension of 2-(3H-spiro[isobenzofuran-1,4'-piperidine]-1'-yl)thiazol-4(5H)-one (4.00 g, 13.9 mmol) and 1,3-dimethoxypropan-2-one (1.97 g, 16.6 mmol) in dichloromethane (48 ml) was added titanium(IV) chloride, 1 M in dichloromethane (33.40 g, 19.4 ml, 19.4 mmol) and pyridine (11.00 g, 11.2 ml, 139 mmol). The reaction mixture was stirred at 40° C. for 12 h, then poured into brine (300 ml) and 1M hydrochloric acid (100 ml) and extracted with dichloromethane (3×500 ml). The organic layers were dried over sodium sulfate and concentrated to dryness. Purification by flash-chromatography with n-heptane/ethyl acetate gave the title compound (2.40 g, 6.18 mmol, 45% yield) as light brown foam. MS m/e: 389.1 ([M+H]+)

Example 16

(5E/Z)-5-(1-phenylethylidene)-2-(1'H,3H-spiro[2-benzofuran-1,4'-piperidin]-1'-yl)-1,3-thiazol-4(5H)-one The title compound was obtained as orange solid in 50% yield according to the general procedure 6 from 2-(3H-spiro[isobenzofuran-1,4'-piperidine]-1'-yl)thiazol-4(5H)-one and acetophenone. MS m/e: 391.1 ([M+H]+)

Example 17

(5Z)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one The title compound was obtained as light yellow solid in 42% yield according to the general procedure 6 from 2-(3H-spiro[isobenzofuran-1,4'-piperidine]-1'-yl)thiazol-4(5H)-one and 1-(4-chlorophenyl)-2,2,2-trifluoroethanone. MS m/e: 479.1 ([M+H]+)

Example 18

(5E)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one The title compound was obtained as yellow solid in 10% yield according to the general procedure 6 from 2-(3H-spiro[isobenzofuran-1,4'-piperidine]-1'-yl)thiazol-4(5H)-one and 1-(4-chlorophenyl)-2,2,2-trifluoroethanone. MS m/e: 479.1 ([M+H]+)

Example 19

(5E/Z)-5-(5-chloro-3,4-dihydronaphthalen-1(2H)-ylidene)-2-(1'H,3H-spiro[2-benzofuran-1,4'-piperidin]-1'-yl)-1,3-thiazol-4(5H)-one The title compound was obtained as light yellow solid in 60% yield according to the general procedure 6 from 2-(3H-spiro[isobenzofuran-1,4'-piperidine]-1'-yl)thiazol-4(5H)-one and 5-chloro-3,4-dihydronaphthalen-1(2H)-one. MS m/e: 451.1 ([M+H]+)

Example 20

(5E/Z)-5-(7-chloro-3,4-dihydronaphthalen-1(2H)-ylidene)-2-(1'H,3H-spiro[2-benzofuran-1,4'-piperidin]-1'-yl)-1,3-thiazol-4(5H)-one The title compound was obtained as yellow solid in 61% yield according to the general procedure 6 from 2-(3H-spiro[isobenzofuran-1,4'-piperidine]-1'-yl)thiazol-4(5H)-one and 7-chloro-3,4-dihydronaphthalen-1(2H)-one. MS m/e: 451.1 ([M+H]+)

Example 21

(5E/Z)-5-[1-(4-chlorophenyl)-2,2-dimethylpropylidene]-2-(1'H,3H-spiro[2-benzofuran-1,4'-piperidin]-1'-yl)-1,3-thiazol-4(5H)-one The title compound was obtained as yellow solid in 25% yield according to the general procedure 6 from 2-(3H-spiro[isobenzofuran-1,4'-piperidine]-1'-yl)thiazol-4(5H)-one and 7-chloro-3,4-dihydronaphthalen-1(2H)-one. MS m/e: 467.1 ([M+H]+)

Example 22

(5E/Z)-5-[(4-chlorophenyl)(cyclopropyl)methylidene]-2-(1'H,3H-spiro[2-benzofuran-1,4'-piperidin]-1'-yl)-1,3-thiazol-4(5H)-one The title compound was obtained as light yellow solid in 65% yield according to the general procedure 6 from 2-(3H-spiro[isobenzofuran-1,4'-piperidine]-1'-yl)thiazol-4(5H)-one and (4-chlorophenyl)(cyclopropyl)methanone. MS m/e: 451.1 ([M+H]+)

Example 23

(5E/Z)-5-[1-(4-chlorophenyl)-2-fluoroethylidene]-2-(1'H,3H-spiro[2-benzofuran-1,4'-piperidin]-1'-yl)-1,3-thiazol-4(5H)-one The title compound was obtained as orange solid in 68% yield according to the general procedure 6 from 2-(3H-spiro[isobenzofuran-1,4'-piperidine]-1'-yl)thiazol-4(5H)-one and 1-(4-chlorophenyl)-2-fluoroethanone. MS m/e: 443.1 ([M+H]+)

Example 24

(5Z)-5-[1-(4-chlorophenyl)propylidene]-2-(1'H,3H-spiro[2-benzofuran-1,4'-piperidin]-1'-yl)-1,3-thiazol-4(5H)-one The title compound was obtained as white solid in 28% yield according to the general procedure 6 from 2-(3H-spiro[isobenzofuran-1,4'-piperidine]-1'-yl)thiazol-4(5H)-one and 1-(4-chlorophenyl)propan-1-one. MS m/e: 439.1 ([M+H]+)

Example 25

(5E)-5-[1-(4-chlorophenyl)propylidene]-2-(1'H,3H-spiro[2-benzofuran-1,4'-piperidin]-1'-yl)-1,3-thiazol-4(5H)-one The title compound was obtained as white solid in 31% yield according to the general procedure 6 from 2-(3H-spiro[isobenzofuran-1,4'-piperidine]-1'-yl)thiazol-4(5H)-one and 1-(4-chlorophenyl)propan-1-one. MS m/e: 439.1 ([M+H]+)

Example 26

(5Z)-5-[1-(4-chlorophenyl)ethylidene]-2-(1'H,3H-spiro[2-benzofuran-1,4'-piperidin]-1'-yl)-1,3-thiazol-4(5H)-one The title compound was obtained as off-white solid in 54% yield according to the general procedure 6 from 2-(3H- spiro[isobenzofuran-1,4'-piperidine]-1'-yl)thiazol-4(5H)-one and 1-(4-chlorophenyl)ethanone. MS m/e: 425.1 ([M+H]+)

Example 27

(5E)-5-[1-(4-chlorophenyl)ethylidene]-2-(1'H,3H-spiro[2-benzofuran-1,4'-piperidin]-1'-yl)-1,3-thiazol-4(5H)-one The title compound was obtained as off-white solid in 8% yield according to the general procedure 6 from 2-(3H-spiro[isobenzofuran-1,4'-piperidine]-1'-yl)thiazol-4(5H)-one and 1-(4-chlorophenyl)ethanone. MS m/e: 425.1 ([M+H]+)

Example 28

(5E)-5-(1-cyclohexylethylidene)-2-(1'H,3H-spiro[2-benzofuran-1,4'-piperidin]-1'-yl)-1,3-thiazol-4(5H)-one The title compound was obtained as white solid in 48% yield according to the general procedure 6 from 2-(3H-spiro[isobenzofuran-1,4'-piperidine]-1'-yl)thiazol-4(5H)-one and 1-cyclohexylethanone. MS m/e: 397.2 ([M+H]+)

Example 29

(5Z)-5-(1-cyclohexylethylidene)-2-(1'H,3H-spiro[2-benzofuran-1,4'-piperidin]-1'-yl)-1,3-thiazol-4(5H)-one The title compound was obtained as white solid in 48% yield according to the general procedure 6 from 2-(3H-spiro[isobenzofuran-1,4'-piperidine]-1'-yl)thiazol-4(5H)-one and 1-cyclohexylethanone. MS m/e: 397.2 ([M+H]+)

Example 30

5-(propan-2-ylidene)-2-(1'H,3H-spiro[2-benzofuran-1,4'-piperidin]-1'-yl)-1,3-thiazol-4(5H)-one The title compound was obtained as white solid in 52% yield according to the general procedure 6 from 2-(3H-spiro[isobenzofuran-1,4'-piperidine]-1'-yl)thiazol-4(5H)-one and acetone. MS m/e: 329.1 ([M+H]+)

Example 31

(5Z)-5-[1-(pyridin-4-yl)propylidene]-2-(1'H,3H-spiro[2-benzofuran-1,4'-piperidine]-1'-yl)-1,3-thiazol-4(5H)-one The title compound was obtained as orange oil in 39% yield according to the general procedure 6 from 2-(3H-spiro[isobenzofuran-1,4'-piperidine]-1'-yl)thiazol-4(5H)-one and 1-(pyridin-4-yl)propan-1-one. MS m/e: 406.1 ([M+H]+)

Example 32

(5E)-5-[1-(pyridin-4-yl)propylidene]-2-(1'H,3H-spiro[2-benzofuran-1,4'-piperidin]-1'-yl)-1,3-thiazol-4(5H)-one The title compound was obtained as orange oil in 26% yield according to the general procedure 6 from 2-(3H-spiro[isobenzofuran-1,4'-piperidine]-1'-yl)thiazol-4(5H)-one and 1-(pyridin-4-yl)propan-1-one. MS m/e: 406.1 ([M+H]+)

Example 33

(5Z)-5-[1-(pyridin-4-yl)ethylidene]-2-(1'H,3H-spiro[2-benzofuran-1,4'-piperidin]-1'-yl)-1,3-thiazol-4(5H)-one The title compound was obtained as orange solid in 41% yield according to the general procedure 6 from 2-(3H-spiro[isobenzofuran-1,4'-piperidine]-1'-yl)thiazol-4(5H)-one and 1-(pyridin-4-yl)ethanone. MS m/e: 392.1 ([M+H]+)

Example 34

(5E/Z)-5-[1-(1H-pyrrol-2-yl)ethylidene]-2-(1'H,3H-spiro[2-benzofuran-1,4'-piperidin]-1'-yl)-1,3-thiazol-4(5H)-one The title compound was obtained as yellow oil in 89% yield according to the general procedure 6 from 2-(3H-spiro[isobenzofuran-1,4'-piperidine]-1'-yl)thiazol-4(5H)-one and 1-(1H-pyrrol-2-yl)ethanone. MS m/e: 380.1 ([M+H]+)

Example 35

(5Z)-5-[1-(furan-2-yl)ethylidene]-2-(1'H,3H-spiro[2-benzofuran-1,4'-piperidin]-1'-yl)-1,3-thiazol-4(5H)-one The title compound was obtained as yellow solid in 53% yield according to the general procedure 6 from 2-(3H-spiro[isobenzofuran-1,4'-piperidine]-1'-yl)thiazol-4(5H)-one and 1-(furan-2-yl)ethanone. MS m/e: 381.1 ([M+H]+)

Example 36

(5E)-5-[1-(pyridin-4-yl)ethylidene]-2-(1'H,3H-spiro[2-benzofuran-1,4'-piperidin]-1'-yl)-1,3-thiazol-4(5H)-one The title compound was obtained as orange oil in 56% yield according to the general procedure 6 from 2-(3H-spiro[isobenzofuran-1,4'-piperidine]-1'-yl)thiazol-4(5H)-one and 1-(pyridin-4-yl)ethanone. MS m/e: 392.1 ([M+H]+)

Example 37

(5Z)-5-[1-(1-methyl-1H-pyrrol-2-yl)ethylidene]-2-(1'H,3H-spiro[2-benzofuran-1,4'-piperidin]-1'-yl)-1,3-thiazol-4(5H)-one The title compound was obtained as yellow solid in 20% yield according to the general procedure 6 from 2-(3H-spiro[isobenzofuran-1,4'-piperidine]-1'-yl)thiazol-4(5H)-one and 1-(1-methyl-1H-pyrrol-2-yl)ethanone.
MS m/e: 394.1 ([M+H]+)

Example 38

(5Z)-5-[1-(pyridin-2-yl)ethylidene]-2-(1'H,3H-spiro[2-benzofuran-1,4'-piperidin]-1'-yl)-1,3-thiazol-4(5H)-one The title compound was obtained as yellow oil in 5% yield according to the general procedure 6 from 2-(3H-spiro

[isobenzofuran-1,4'-piperidine]-1'-yl)thiazol-4(5H)-one and 1-(pyridin-2-yl)ethanone. MS m/e: 392.1 ([M+H]+)

Example 39

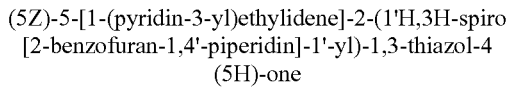

(5Z)-5-[1-(pyridin-3-yl)ethylidene]-2-(1'H,3H-spiro[2-benzofuran-1,4'-piperidin]-1'-yl)-1,3-thiazol-4(5H)-one The title compound was obtained as light yellow solid in 32% yield according to the general procedure 6 from 2-(3H-spiro[isobenzofuran-1,4'-piperidine]-1'-yl)thiazol-4(5H)-one and 1-(pyridin-3-yl)ethanone. MS m/e: 392.2 ([M+H]+)

Example 40

(5E/Z)-5-[1-(2-fluorophenyl)ethylidene]-2-(1'H,3H-spiro[2-benzofuran-1,4'-piperidin]-1'-yl)-1,3-thiazol-4(5H)-one The title compound was obtained as orange solid in 71% yield according to the general procedure 6 from 2-(3H-spiro[isobenzofuran-1,4'-piperidine]-1'-yl)thiazol-4(5H)-one and 1-(2-fluorophenyl)ethanone. MS m/e: 409.3 ([M+H]+)

Example 41

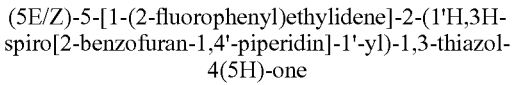

tert-butyl 4-[4-oxo-2-(1'H,3H-spiro[2-benzofuran-1,4'-piperidin]-1'-yl)-1,3-thiazol-5(4H)-ylidene]piperidine-1-carboxylate The title compound was obtained as yellow solid in 14% yield according to the general procedure 6 from 2-(3H-spiro[isobenzofuran-1,4'-piperidine]-1'-yl)thiazol-4(5H)-one and tert-butyl 4-oxopiperidine-1-carboxylate. MS m/e: 470.3 ([M+H]+)

Example 42

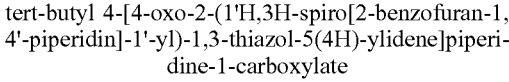

(5E/Z)-5-(1-cyclopropylethylidene)-2-(1'H,3H-spiro[2-benzofuran-1,4'-piperidin]-1'-yl)-1,3-thiazol-4(5H)-one The title compound was obtained as orange gum in 94% yield according to the general procedure 6 from 2-(3H-spiro[isobenzofuran-1,4'-piperidine]-1'-yl)thiazol-4(5H)-one and 1-cyclopropylethanone. MS m/e: 355.2 ([M+H]+)

Example 43

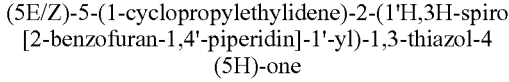

(5E/Z)-5-(1-cyclopentylethylidene)-2-(1'H,3H-spiro[2-benzofuran-1,4'-piperidin]-1'-yl)-1,3-thiazol-4(5H)-one The title compound was obtained as orange gum in 63% yield according to the general procedure 6 from 2-(3H-spiro[isobenzofuran-1,4'-piperidine]-1'-yl)thiazol-4(5H)-one and 1-cyclopentylethanone. MS m/e: 383.3 ([M+H]+)

Example 44

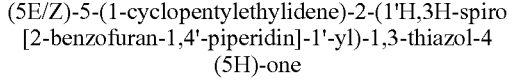

2-(1'H,3H-spiro[2-benzofuran-1,4'-piperidin]-1'-yl)-5-(tetrahydro-4H-pyran-4-ylidene)-1,3-thiazol-4(5H)-one The title compound was obtained as off-white solid in 41% yield according to the general procedure 6 from 2-(3H-spiro[isobenzofuran-1,4'-piperidine]-1'-yl)thiazol-4(5H)-one and dihydro-2H-pyran-4(3H)-one. MS m/e: 371.1 ([M+H]+)

Example 45

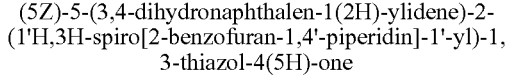

(5Z)-5-(3,4-dihydronaphthalen-1(2H)-ylidene)-2-(1'H,3H-spiro[2-benzofuran-1,4'-piperidin]-1'-yl)-1,3-thiazol-4(5H)-one The title compound was obtained as orange solid in 98% yield according to the general procedure 6 from 2-(3H-spiro[isobenzofuran-1,4'-piperidine]-1'-yl)thiazol-4(5H)-one and 3,4-dihydronaphthalen-1(2H)-one. MS m/e: 417.3 ([M+H]+)

Example 46

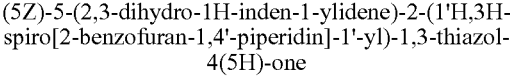

(5Z)-5-(2,3-dihydro-1H-inden-1-ylidene)-2-(1'H,3H-spiro[2-benzofuran-1,4'-piperidin]-1'-yl)-1,3-thiazol-4(5H)-one The title compound was obtained as brown solid in 66% yield according to the general procedure 6 from 2-(3H-spiro[isobenzofuran-1,4'-piperidine]-1'-yl)thiazol-4(5H)-one and 2,3-dihydro-1H-inden-1-one. MS m/e: 403.4 ([M+H]+)

Example 47

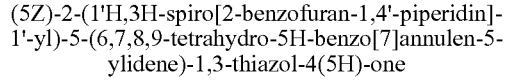

(5Z)-2-(1'H,3H-spiro[2-benzofuran-1,4'-piperidin]-1'-yl)-5-(6,7,8,9-tetrahydro-5H-benzo[7]annulen-5-ylidene)-1,3-thiazol-4(5H)-one The title compound was obtained as orange gum in 90% yield according to the general procedure 6 from 2-(3H-spiro[isobenzofuran-1,4'-piperidine]-1'-yl)thiazol-4(5H)-one and 6,7,8,9-tetrahydro-5H-benzo[7]annulen-5-one. MS m/e: 431.4 ([M+H]+)

Example 48

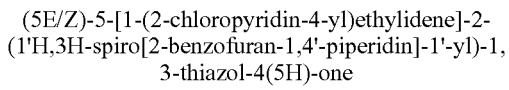

(5E/Z)-5-[1-(2-chloropyridin-4-yl)ethylidene]-2-(1'H,3H-spiro[2-benzofuran-1,4'-piperidin]-1'-yl)-1,3-thiazol-4(5H)-one The title compound was obtained as orange solid in 76% yield according to the general procedure 6 from 2-(3H-spiro[isobenzofuran-1,4'-piperidine]-1'-yl)thiazol-4(5H)-one and 1-(2-chloropyridin-4-yl)ethanone. MS m/e: 426.1 ([M]+)

Example 49

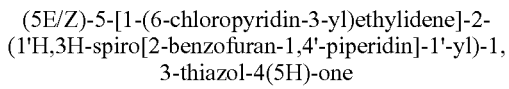

(5E/Z)-5-[1-(6-chloropyridin-3-yl)ethylidene]-2-(1'H,3H-spiro[2-benzofuran-1,4'-piperidin]-1'-yl)-1,3-thiazol-4(5H)-one The title compound was obtained as orange solid in 85% yield according to the general procedure 6 from 2-(3H-spiro[isobenzofuran-1,4'-piperidine]-1'-yl)thiazol-4(5H)-one and 1-(6-chloropyridin-3-yl)ethanone. MS m/e: 426.1 ([M]+)

Example 50

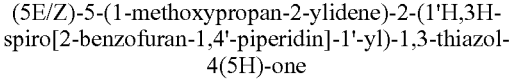

(5E/Z)-5-(1-methoxypropan-2-ylidene)-2-(1'H,3H-spiro[2-benzofuran-1,4'-piperidin]-1'-yl)-1,3-thiazol-4(5H)-one The title compound was obtained as orange gum in 60% yield according to the general procedure 6 from 2-(3H-spiro

[isobenzofuran-1,4'-piperidine]-1'-yl)thiazol-4(5H)-one and 1-methoxypropan-2-one. MS m/e: 359.1 ([M+H]+)

Example 51

(5E/Z)-5-(1-fluoropropan-2-ylidene)-2-(1'H,3H-spiro[2-benzofuran-1,4'-piperidin]-1'-yl)-1,3-thiazol-4(5H)-one The title compound was obtained as yellow solid in 55% yield according to the general procedure 6 from 2-(3H-spiro[isobenzofuran-1,4'-piperidine]-1'-yl)thiazol-4(5H)-one and 1-fluoropropan-2-one. MS m/e: 347.2 ([M+H]+)

Example 52

5-cyclohexylidene-2-(1'H,3H-spiro[2-benzofuran-1,4'-piperidin]-1'-yl)-1,3-thiazol-4(5H)-one The title compound was obtained as yellow gum in 64% yield according to the general procedure 6 from 2-(3H-spiro[isobenzofuran-1,4'-piperidine]-1'-yl)thiazol-4(5H)-one and cyclohexanone. MS m/e: 369.2 ([M+H]+)

Example 53

5-cyclopentylidene-2-(1'H,3H-spiro[2-benzofuran-1,4'-piperidin]-1'-yl)-1,3-thiazol-4(5H)-one The title compound was obtained as yellow solid in 37% yield according to the general procedure 6 from 2-(3H-spiro[isobenzofuran-1,4'-piperidine]-1'-yl)thiazol-4(5H)-one and cyclopentanone. MS m/e: 355.2 ([M+H]+)

Example 54

(5E/Z)-5-(5-hydroxy-2,3-dihydro-1H-inden-1-ylidene)-2-(1'H,3H-spiro[2-benzofuran-1,4'-piperidin]-1'-yl)-1,3-thiazol-4(5H)-one The title compound was obtained as orange solid in 3% yield according to the general procedure 6 from 2-(3H-spiro[isobenzofuran-1,4'-piperidine]-1'-yl)thiazol-4(5H)-one and 5-hydroxy-2,3-dihydro-1H-inden-1-one. MS m/e: 419.2 ([M+H]+)

Example 55

(5E/Z)-5-[hexahydro-1,2,4-(methanetriyl)pentalen-5(1H)-ylidene]-2-(1'H,3H-spiro[2-benzofuran-1,4'-piperidin]-1'-yl)-1,3-thiazol-4(5H)-one The title compound was obtained as orange solid in 64% yield according to the general procedure 6 from 2-(3H-spiro[isobenzofuran-1,4'-piperidine]-1'-yl)thiazol-4(5H)-one and 1,2,4-methenopentalen-5(1H)-one. MS m/e: 405.2 ([M+H]+)

Example 56

(5E)-5-[1-(2-fluorophenyl)ethylidene]-2-(1'H,3H-spiro[2-benzofuran-1,4'-piperidin]-1'-yl)-1,3-thiazol-4(5H)-one The title compound was obtained as brown solid in 22% yield according to the general procedure 6 from 2-(3H-spiro[isobenzofuran-1,4'-piperidine]-1'-yl)thiazol-4(5H)-one and 1-(2-fluorophenyl)ethanone. MS m/e: 409.4 ([M+H]+)

Example 57

(5Z)-5-[1-(2-fluorophenyl)ethylidene]-2-(1'H,3H-spiro[2-benzofuran-1,4'-piperidin]-1'-yl)-1,3-thiazol-4(5H)-one The title compound was obtained as orange solid in 42% yield according to the general procedure 6 from 2-(3H-spiro[isobenzofuran-1,4'-piperidine]-1'-yl)thiazol-4(5H)-one and 1-(2-fluorophenyl)ethanone. MS m/e: 409.4 ([M+H]+)

Example 58

(5E)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one The title compound was obtained as off-white solid in 24% yield according to the general procedure 6 from 2-(3H-spiro[isobenzofuran-1,4'-piperidine]-1'-yl)thiazol-4(5H)-one and 1-(tert-butyldimethylsilyloxy)propan-2-one. MS m/e: 459.2 ([M+H]+)

Example 59

(5Z)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one The title compound was obtained as yellow oil in 47% yield according to the general procedure 6 from 2-(3H-spiro[isobenzofuran-1,4'-piperidine]-1'-yl)thiazol-4(5H)-one and 1-(tert-butyldimethylsilyloxy)propan-2-one. MS m/e: 459.2 ([M+H]+)

Example 60

5-(1,1-dioxidotetrahydro-4H-thiopyran-4-ylidene)-2-(1'H,3H-spiro[2-benzofuran-1,4'-piperidin]-1'-yl)-1,3-thiazol-4(5H)-one The title compound was obtained as off-white solid in 31% yield according to the general procedure 6 from 2-(3H-spiro[isobenzofuran-1,4'-piperidine]-1'-yl)thiazol-4(5H)-one and 1,1-dioxotetrahydro-2H-thiopyran-4-one. MS m/e: 419.1 ([M+H]+)

Example 61

(5Z)-5-[1-(2-fluoropyridin-3-yl)ethylidene]-2-(1'H,3H-spiro[2-benzofuran-1,4'-piperidin]-1'-yl)-1,3-thiazol-4(5H)-one The title compound was obtained as orange solid in 18% yield according to the general procedure 6 from 2-(3H-spiro[isobenzofuran-1,4'-piperidine]-1'-yl)thiazol-4(5H)-one and 1-(2-fluoropyridin-3-yl)ethanone. MS m/e: 410.1 ([M+H]+)

Example 62

(5Z)-5-[1-(1-methyl-1H-pyrazol-4-yl)ethylidene]-2-(1'H,3H-spiro[2-benzofuran-1,4'-piperidin]-1'-yl)-1,3-thiazol-4(5H)-one The title compound was obtained as orange solid in 56% yield according to the general procedure 6 from 2-(3H-spiro

[isobenzofuran-1,4'-piperidine]-1'-yl)thiazol-4(5H)-one and 1-(1-methyl-1H-pyrazol-4-yl)ethanone. MS m/e: 395.1 ([M+H]+)

Example 63

(5Z)-2-(1'H,3H-spiro[2-benzofuran-1,4'-piperidin]-1'-yl)-5-[1-(1,3-thiazol-2-yl)ethylidene]-1,3-thiazol-4(5H)-one The title compound was obtained as orange solid in 19% yield according to the general procedure 6 from 2-(3H-spiro[isobenzofuran-1,4'-piperidine]-1'-yl)thiazol-4(5H)-one and 1-(thiazol-2-yl)ethanone. MS m/e: 498.1 ([M+H]+)

Example 64

(5E/Z)-5-[1-(5-methyl-1,2-oxazol-3-yl)propylidene]-2-(1'H,3H-spiro[2-benzofuran-1,4'-piperidin]-1'-yl)-1,3-thiazol-4(5H)-one The title compound was obtained as orange oil in 51% yield according to the general procedure 6 from 2-(3H-spiro[isobenzofuran-1,4'-piperidine]-1'-yl)thiazol-4(5H)-one and 1-(5-methylisoxazol-3-yl)propan-1-one. MS m/e: 410.1 ([M+H]+)

Example 65 tert-butyl {(2E)-2-[4-oxo-2-(1'H,3H-spiro[2-benzofuran-1,4'-piperidin]-1'-yl)-1,3-thiazol-5(4H)-ylidene]propyl}carbamate The title compound was obtained as orange oil in 30% yield according to the general procedure 6 from 2-(3H-spiro[isobenzofuran-1,4'-piperidine]-1'-yl)thiazol-4(5H)-one and tert-butyl 2-oxopropylcarbamate. MS m/e: 444.2 ([M+H]+)

Example 66

(5E)-5-(1-aminopropan-2-ylidene)-2-(1'H,3H-spiro[2-benzofuran-1,4'-piperidin]-1'-yl)-1,3-thiazol-4(5H)-one hydrochloride (1:1)

A mixture of tert-butyl {(2E)-2-[4-oxo-2-(1'H,3H-spiro[2-benzofuran-1,4'-piperidin]-1'-yl)-1,3-thiazol-5(4H)-ylidene]propyl}carbamate (9.6 mg, 21.6 μmol) and hydrogen chloride 4M in dioxane (271 μl, 1.08 mmol) was stirred at 22° C. for 1 h. Concentration to dryness gave the title compound (8.1 mg, 21.3 μmol, 99% yield) as orange solid. MS m/e: 344.0 ([M+H]+)

Example 67

(5E/Z)-8-chloro-5-[4-oxo-2-(1'H,3H-spiro[2-benzofuran-1,4'-piperidin]-1'-yl)-1,3-thiazol-5(4H)-ylidene]-2,3,4,5-tetrahydro-1H-2-benzazepin-1-one The title compound was obtained as orange solid in 31% yield according to the general procedure 6 from 2-(3H-spiro[isobenzofuran-1,4'-piperidine]-1'-yl)thiazol-4(5H)-one and 8-chloro-3,4-dihydro-1H-benzo[c]azepine-1,5(2H)-dione. MS m/e: 480.1 ([M+H]+)

Example 68

5-[1-(methylsulfonyl)piperidin-4-ylidene]-2-(1'H,3H-spiro[2-benzofuran-1,4'-piperidin]-1'-yl)-1,3-thiazol-4(5H)-one The title compound was obtained as orange solid in 53% yield according to the general procedure 6 from 2-(3H-spiro[isobenzofuran-1,4'-piperidine]-1'-yl)thiazol-4(5H)-one and 1-(methylsulfonyl)piperidin-4-one. MS m/e: 448.1 ([M+H]+)

Example 69

5-(1,3-difluoropropan-2-ylidene)-2-(1'H,3H-spiro[2-benzofuran-1,4'-piperidin]-1'-yl)-1,3-thiazol-4(5H)-one The title compound was obtained as orange solid in 46% yield according to the general procedure 6 from 2-(3H-spiro[isobenzofuran-1,4'-piperidine]-1'-yl)thiazol-4(5H)-one and 1,3-difluoropropan-2-one. MS m/e: 365.1 ([M+H]+)

Example 70

(5E/Z)-5-(but-3-en-2-ylidene)-2-(1'H,3H-spiro[2-benzofuran-1,4'-piperidin]-1'-yl)-1,3-thiazol-4(5H)-one The title compound was obtained as light yellow solid in 18% yield according to the general procedure 6 from 2-(3H-spiro[isobenzofuran-1,4'-piperidine]-1'-yl)thiazol-4(5H)-one and but-3-en-2-one. MS m/e: 341.1 ([M+H]+)

Example 71

(5Z)-2-(1'H,3H-spiro[2-benzofuran-1,4'-piperidin]-1'-yl)-5-(1,1,1-trifluoropropan-2-ylidene)-1,3-thiazol-4(5H)-one The title compound was obtained as light yellow solid in 45% yield according to the general procedure 6 from 2-(3H-spiro[isobenzofuran-1,4'-piperidine]-1'-yl)thiazol-4(5H)-one and 1,1,1-trifluoropropan-2-one. MS m/e: 383.1 ([M+H]+)

Example 72

2-[4-oxo-2-(1'H,3H-spiro[2-benzofuran-1,4'-piperidin]-1'-yl)-1,3-thiazol-5(4H)-ylidene]propane-1,3-diyl diacetate The title compound was obtained as orange solid in 35% yield according to the general procedure 6 from 2-(3H-spiro[isobenzofuran-1,4'-piperidine]-1'-yl)thiazol-4(5H)-one and 2-oxopropane-1,3-diyl diacetate. MS m/e: 445.1 ([M+H]+)

Example 73

(5E/Z)-5-(2-methoxycyclohexylidene)-2-(1'H,3H-spiro[2-benzofuran-1,4'-piperidin]-1'-yl)-1,3-thiazol-4(5H)-one The title compound was obtained as yellow oil in 91% yield according to the general procedure 6 from 2-(3H-spiro

[isobenzofuran-1,4'-piperidine]-1'-yl)thiazol-4(5H)-one and 2-methoxycyclohexanone. MS m/e: 399.2 ([M+H]+)

Example 74

(3E/Z)-3-[4-oxo-2-(1'H,3H-spiro[2-benzofuran-1,4'-piperidin]-1'-yl)-1,3-thiazol-5(4H)-ylidene]-1,3-dihydro-2H-indol-2-one The title compound was obtained as brown solid in 27% yield according to the general procedure 6 from 2-(3H-spiro[isobenzofuran-1,4'-piperidine]-1'-yl)thiazol-4(5H)-one and indoline-2,3-dione. MS m/e: 418.1 ([M+H]+)

Example 75

5-cyclobutylidene-2-(1'H,3H-spiro[2-benzofuran-1,4'-piperidin]-1'-yl)-1,3-thiazol-4(5H)-one The title compound was obtained as yellow solid in 66% yield according to the general procedure 6 from 2-(3H-spiro[isobenzofuran-1,4'-piperidine]-1'-yl)thiazol-4(5H)-one and cyclobutanone. MS m/e: 341.1 ([M+H]+)

Example 76

(5E/Z)-5-(dihydro-2H-pyran-3(4H)-ylidene)-2-(1'H,3H-spiro[2-benzofuran-1,4'-piperidin]-1'-yl)-1,3-thiazol-4(5H)-one The title compound was obtained as yellow oil in 33% yield according to the general procedure 6 from 2-(3H-spiro[isobenzofuran-1,4'-piperidine]-1'-yl)thiazol-4(5H)-one and dihydro-2H-pyran-3(4H)-one. MS m/e: 371.1 ([M+H]+)

Example 77

(5E/Z)-5-[1-(2-methylpyridin-4-yl)ethylidene]-2-(1'H,3H-spiro[2-benzofuran-1,4'-piperidin]-1'-yl)-1,3-thiazol-4(5H)-one The title compound was obtained as orange oil in 44% yield according to the general procedure 6 from 2-(3H-spiro[isobenzofuran-1,4'-piperidine]-1'-yl)thiazol-4(5H)-one and 1-(2-methylpyridin-4-yl)ethanone. MS m/e: 406.1 ([M+H]+)

Example 78

(5E/Z)-2-(1'H,3H-spiro[2-benzofuran-1,4'-piperidin]-1'-yl)-5-[1-(tetrahydro-2H-pyran-4-yl)ethylidene]-1,3-thiazol-4(5H)-one The title compound was obtained as orange foam in 59% yield according to the general procedure 6 from 2-(3H-spiro[isobenzofuran-1,4'-piperidine]-1'-yl)thiazol-4(5H)-one and 1-(tetrahydro-2H-pyran-4-yl)ethanone. MS m/e: 399.1 ([M+H]+)

Example 79

(5Z)-5-[1-(5-methyl-1,2-oxazol-3-yl)ethylidene]-2-(1'H,3H-spiro[2-benzofuran-1,4'-piperidin]-1'-yl)-1,3-thiazol-4(5H)-one)

The title compound was obtained as orange solid in 83% yield according to the general procedure 6 from 2-(3H-spiro[isobenzofuran-1,4'-piperidine]-1'-yl)thiazol-4(5H)-one and 1-(5-methylisoxazol-3-yl)ethanone. MS m/e: 396 ([M+H]+)

Example 80 tert-butyl (4E/Z)-4-[4-oxo-2-(1'H,3H-spiro[2-benzofuran-1,4'-piperidin]-1'-yl)-1,3-thiazol-5(4H)-ylidene]azepane-1-carboxylate The title compound was obtained as orange oil in 12% yield according to the general procedure 6 from 2-(3H-spiro[isobenzofuran-1,4'-piperidine]-1'-yl)thiazol-4(5H)-one and tert-butyl 4-oxoazepane-1-carboxylate. MS m/e: 484 ([M+H]+)

Example 81

(5E/Z)-5-(azepan-4-ylidene)-2-(1'H,3H-spiro[2-benzofuran-1,4'-piperidin]-1'-yl)-1,3-thiazol-4(5H)-one hydrochloride A solution of tert-butyl (4E/Z)-4-[4-oxo-2-(1'H,3H-spiro[2-benzofuran-1,4'-piperidin]-1'-yl)-1,3-thiazol-5(4H)-ylidene]azepane-1-carboxylate (12 mg, 24.8 µmol) and hydrogen chloride 4M in dioxane (310 µl, 1.24 mmol) was stirred at 22° C. for 1 hr. Concentration to dryness gave the title compound (4 mg, 9.52 µmol, 38% yield) as orange oil. MS m/e: 384 ([M+H]+)

Example 82

5-(diphenylmethylidene)-2-(1'H,3H-spiro[2-benzofuran-1,4'-piperidin]-1'-yl)-1,3-thiazol-4(5H)-one The title compound was obtained as light yellow solid in 92% yield according to the general procedure 6 from 2-(3H-spiro[isobenzofuran-1,4'-piperidine]-1'-yl)thiazol-4(5H)-one and benzophenone. MS m/e: 453.1 ([M+H]+)

Example 83

(5Z)-5-[1-(2-chloropyridin-3-yl)ethylidene]-2-(1'H,3H-spiro[2-benzofuran-1,4'-piperidin]-1'-yl)-1,3-thiazol-4(5H)-one The title compound was obtained as yellow solid in 18% yield according to the general procedure 6 from 2-(3H-spiro[isobenzofuran-1,4'-piperidine]-1'-yl)thiazol-4(5H)-one and 1-(2-chloropyridin-3-yl)ethanone. MS m/e: 426.1 ([M+H]+)

Example 84

(5E)-5-[1-(2-chloropyridin-3-yl)ethylidene]-2-(1'H,3H-spiro[2-benzofuran-1,4'-piperidin]-1'-yl)-1,3-thiazol-4(5H)-one The title compound was obtained as orange gum in 35% yield according to the general procedure 6 from 2-(3H-spiro[isobenzofuran-1,4'-piperidine]-1'-yl)thiazol-4(5H)-one and 1-(2-chloropyridin-3-yl)ethanone. MS m/e: 448.1 ([M+Na]+)

Example 85

(5E/Z)-5-[1-(6-methoxypyridin-3-yl)ethylidene]-2-(1'H,3H-spiro[2-benzofuran-1,4'-piperidin]-1'-yl)-1,3-thiazol-4(5H)-one The title compound was obtained as orange oil in 70% yield according to the general procedure 6 from 2-(3H-spiro

[isobenzofuran-1,4'-piperidine]-1'-yl)thiazol-4(5H)-one and 1-(6-methoxypyridin-3-yl)ethanone. MS m/e: 422.1 ([M+H]+)

Example 86

(5E/Z)-5-[1-(2,4-dimethyl-1,3-oxazol-5-yl)ethylidene]-2-(1'H,3H-spiro[2-benzofuran-1,4'-piperidin]-1'-yl)-1,3-thiazol-4(5H)-one The title compound was obtained as orange solid in 75% yield according to the general procedure 4 from 2-(3H-spiro[isobenzofuran-1,4'-piperidine]-1'-yl)thiazol-4(5H)-one and 1-(2,4-dimethyloxazol-5-yl)ethanone. MS m/e: 410.1 ([M+H]+)

Example 87

(5E/Z)-5-(1H-isochromen-4(3H)-ylidene)-2-(1'H,3H-spiro[2-benzofuran-1,4'-piperidin]-1'-yl)-1,3-thiazol-4(5H)-one The title compound was obtained as yellow solid in 65% yield according to the general procedure 6 from 2-(3H-spiro[isobenzofuran-1,4'-piperidine]-1'-yl)thiazol-4(5H)-one and isochroman-4-one. MS m/e: 419.1 ([M+H]+)

Example 88 tert-butyl (3E/Z)-3-[4-oxo-2-(1'H,3H-spiro[2-benzofuran-1,4'-piperidin]-1'-yl)-1,3-thiazol-5(4H)-ylidene]piperidine-1-carboxylate The title compound was obtained as orange gum in 14% yield according to the general procedure 6 from 2-(3H-spiro[isobenzofuran-1,4'-piperidine]-1'-yl)thiazol-4(5H)-one and tert-butyl 3-oxopiperidine-1-carboxylate. MS m/e: 470.2 ([M+H]+)

Example 89

(5E/Z)-5-(3-chloro-6,7,8,9-tetrahydro-5H-benzo[7]annulen-5-ylidene)-2-(1'H,3H-spiro[2-benzofuran-1,4'-piperidin]-1'-yl)-1,3-thiazol-4(5H)-one The title compound was obtained as off-white solid in 100% yield according to the general procedure 6 from 2-(3H-spiro[isobenzofuran-1,4'-piperidine]-1'-yl)thiazol-4(5H)-one and 3-chloro-6,7,8,9-tetrahydro-5H-benzo[7]annulen-5-one. MS m/e: 465.1 ([M]+)

Example 90

(5Z)-5-(pyridin-2-ylmethylidene)-2-(1'H,3H-spiro[2-benzofuran-1,4'-piperidin]-1'-yl)-1,3-thiazol-4(5H)-one The title compound was obtained as orange solid in 32% yield according to the general procedure 6 from 2-(3H-spiro[isobenzofuran-1,4'-piperidine]-1'-yl)thiazol-4(5H)-one and picolinaldehyde. MS m/e: 378.3 ([M+H]+)

Example 91

5-[(5-methyl-1,2-oxazol-3-yl)methylidene]-2-(1'H,3H-spiro[2-benzofuran-1,4'-piperidin]-1'-yl)-1,3-thiazol-4(5H)-one The title compound was obtained as yellow solid in 45% yield according to the general procedure 6 from 2-(3H-spiro[isobenzofuran-1,4'-piperidine]-1'-yl)thiazol-4(5H)-one and 5-methylisoxazole-3-carbaldehyde. MS m/e: 382.3 ([M+H]+)

Example 92

(5E)-5-(2-methoxy-1-phenylethylidene)-2-(1'H,3H-spiro[2-benzofuran-1,4'-piperidin]-1'-yl)-1,3-thiazol-4(5H)-one The title compound was obtained as orange solid in 50% yield according to the general procedure 6 from 2-(3H-spiro[isobenzofuran-1,4'-piperidine]-1'-yl)thiazol-4(5H)-one and 2-methoxy-1-phenylethanone. MS m/e: 421.1 ([M+H]+)

Example 93

5-[(5-methyl-1,2-oxazol-3-yl)methylidene]-2-(1'H,3H-spiro[2-benzofuran-1,4'-piperidin]-1'-yl)-1,3-thiazol-4(5H)-one The title compound was obtained as orange solid in 84% yield according to the general procedure 6 from 2-(3H-spiro[isobenzofuran-1,4'-piperidine]-1'-yl)thiazol-4(5H)-one and 5-methylisoxazole-3-carbaldehyde. MS m/e: 382.1 ([M+H]+)

Example 94

5-(pyridin-3-ylmethylidene)-2-(1'H,3H-spiro[2-benzofuran-1,4'-piperidin]-1'-yl)-1,3-thiazol-4(5H)-one The title compound was obtained as off-white solid in 61% yield according to the general procedure 6 from 2-(3H-spiro[isobenzofuran-1,4'-piperidine]-1'-yl)thiazol-4(5H)-one and nicotinaldehyde. MS m/e: 378.1 ([M+H]+)

Example 95

5-(pyridin-4-ylmethylidene)-2-(1'H,3H-spiro[2-benzofuran-1,4'-piperidin]-1'-yl)-1,3-thiazol-4(5H)-one The title compound was obtained as off-white solid in 71% yield according to the general procedure 6 from 2-(3H-spiro[isobenzofuran-1,4'-piperidine]-1'-yl)thiazol-4(5H)-one and isonicotinaldehyde. MS m/e: 378.1 ([M+H]+)

Example 96

(5Z)-5-[1-(6-chloropyridin-3-yl)ethylidene]-2-(1'H,3H-spiro[2-benzofuran-1,4'-piperidin]-1'-yl)-1,3-thiazol-4(5H)-one The title compound was obtained as yellow solid in 21% yield according to the general procedure 6 from 2-(3H-spiro[isobenzofuran-1,4'-piperidine]-1'-yl)thiazol-4(5H)-one and 1-(6-chloropyridin-3-yl)ethanone. MS m/e: 426.1 ([M+H]+)

Example 97

(5E)-5-[1-(6-chloropyridin-3-yl)ethylidene]-2-(1'H,3H-spiro[2-benzofuran-1,4'-piperidin]-1'-yl)-1,3-thiazol-4(5H)-one The title compound was obtained as yellow solid in 12% yield according to the general procedure 6 from 2-(3H-spiro

[isobenzofuran-1,4'-piperidine]-1'-yl)thiazol-4(5H)-one and 1-(6-chloropyridin-3-yl)ethanone. MS m/e: 429.5 ([M+H]+)

Example 98

5-(10,11-dihydro-5H-dibenzo[a,d][7]annulen-5-ylidene)-2-(1'H,3H-spiro[2-benzofuran-1,4'-piperidin]-1'-yl)-1,3-thiazol-4(5H)-one The title compound was obtained as yellow solid in 11% yield according to the general procedure 6 from 2-(3H-spiro[isobenzofuran-1,4'-piperidine]-1'-yl)thiazol-4(5H)-one and dibenzosuberone. MS m/e: 479.4 ([M+H]+)

Example 99

5-(5H-dibenzo[a,d][7]annulen-5-ylidene)-2-(1'H,3H-spiro[2-benzofuran-1,4'-piperidin]-1'-yl)-1,3-thiazol-4(5H)-one The title compound was obtained as yellow solid in 29% yield according to the general procedure 6 from 2-(3H-spiro[isobenzofuran-1,4'-piperidine]-1'-yl)thiazol-4(5H)-one and dibenzosuberenone. MS m/e: 477.4 ([M+H]+)

Example 100

5-[bis(4-chlorophenyl)methylidene]-2-(1'H,3H-spiro[2-benzofuran-1,4'-piperidin]-1'-yl)-1,3-thiazol-4(5H)-one The title compound was obtained as yellow solid in 92% yield according to the general procedure 6 from 2-(3H-spiro[isobenzofuran-1,4'-piperidine]-1'-yl)thiazol-4(5H)-one and bis(4-chlorophenyl)methanone. MS m/e: 521.3 ([M+H]+)

Example 101

5-[bis(4-fluorophenyl)methylidene]-2-(1'H,3H-spiro[2-benzofuran-1,4'-piperidin]-1'-yl)-1,3-thiazol-4(5H)-one The title compound was obtained as yellow solid in 89% yield according to the general procedure 6 from 2-(3H-spiro[isobenzofuran-1,4'-piperidine]-1'-yl)thiazol-4(5H)-one and bis(4-fluorophenyl)methanone. MS m/e: 489.4 ([M+H]+)

Example 102

2-(1'H,3H-spiro[2-benzofuran-1,4'-piperidin]-1'-yl)-5-(9H-thioxanthen-9-ylidene)-1,3-thiazol-4(5H)-one The title compound was obtained as yellow solid in 74% yield according to the general procedure 6 from 2-(3H-spiro[isobenzofuran-1,4'-piperidine]-1'-yl)thiazol-4(5H)-one and 9H-thioxanthen-9-one. MS m/e: 483.3 ([M+H]+)

Example 103

2-(1'H,3H-spiro[2-benzofuran-1,4'-piperidin]-1'-yl)-5-(9H-xanthen-9-ylidene)-1,3-thiazol-4(5H)-one The title compound was obtained as yellow solid in 88% yield according to the general procedure 6 from 2-(3H-spiro[isobenzofuran-1,4'-piperidine]-1'-yl)thiazol-4(5H)-one and 9H-xanthen-9-one. MS m/e: 467.4 ([M+H]+)

Example 104

5-(9H-fluoren-9-ylidene)-2-(1'H,3H-spiro[2-benzofuran-1,4'-piperidin]-1'-yl)-1,3-thiazol-4(5H)-one The title compound was obtained as yellow solid in 54% yield according to the general procedure 6 from 2-(3H-spiro[isobenzofuran-1,4'-piperidine]-1'-yl)thiazol-4(5H)-one and 9H-fluoren-9-one. MS m/e: 451.4 ([M+H]+)

Example 105

(5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one The title compound was obtained as light yellow solid in 5% yield according to the general procedure 6 from 2-(3H-spiro[isobenzofuran-1,4'-piperidine]-1'-yl)thiazol-4(5H)-one and 1-(3,5-dimethylisoxazol-4-yl)ethanone. MS m/e: 410.5 ([M+H]+)

Example 106

(5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one The title compound was obtained as light yellow solid in 3% yield according to the general procedure 6 from 2-(3H-spiro[isobenzofuran-1,4'-piperidine]-1'-yl)thiazol-4(5H)-one and 1-(3,5-dimethylisoxazol-4-yl)ethanone. MS m/e: 410.2 ([M+H]+)

Example 107

(5Z)-5-[1-(1H-imidazol-2-yl)ethylidene]-2-(1'H,3H-spiro[2-benzofuran-1,4'-piperidin]-1'-yl)-1,3-thiazol-4(5H)-one The title compound was obtained as yellow solid in 3% yield according to the general procedure 6 from 2-(3H-spiro[isobenzofuran-1,4'-piperidine]-1'-yl)thiazol-4(5H)-one and 1-(1H-imidazol-2-yl)ethanone. MS m/e: 381.5 ([M+H]+)

Example 108

(5E/Z)-5-[1-(furo[3,2-b]pyridin-2-yl)ethylidene]-2-(1'H,3H-spiro[2-benzofuran-1,4'-piperidin]-1'-yl)-1,3-thiazol-4(5H)-one The title compound was obtained as light brown solid in 36% yield according to the general procedure 6 from 2-(3H-spiro[isobenzofuran-1,4'-piperidine]-1'-yl)thiazol-4(5H)-one and 1-(furo[3,2-b]pyridin-2-yl)ethanone. MS m/e: 432.5 ([M+H]+)

Example 109

(5E/Z)-5-[1-(5-methyl-1H-1-imidazol-4-yl)ethylidene]-2-(1'H,3H-spiro[2-benzofuran-1,4'-piperidin]-1'-yl)-1,3-thiazol-4(5H)-one The title compound was obtained as light brown solid in 3% yield according to the general procedure 6 from 2-(3H- spiro[isobenzofuran-1,4'-piperidine]-1'-yl)thiazol-4(5H)-one and 1-(5-methyl-1H-imidazol-4-yl)ethanone. MS m/e: 395.5 ([M+H]+)

Example 110

5-[di(pyridin-2-yl)methylidene]-2-(1'H,3H-spiro[2-benzofuran-1,4'-piperidin]-1'-yl)-1,3-thiazol-4(5H)-one The title compound was obtained as yellow solid in 73% yield according to the general procedure 6 from 2-(3H-spiro[isobenzofuran-1,4'-piperidine]-1'-yl)thiazol-4(5H)-one and dipyridin-2-ylmethanone. MS m/e: 455.4 ([M+H]+)

Example 111

5-(1,1,1,3,3,3-hexafluoropropan-2-ylidene)-2-(1'H,3H-spiro[2-benzofuran-1,4'-piperidin]-1'-yl)-1,3-thiazol-4(5H)-one The title compound was obtained as light brown solid in 98% yield according to the general procedure 6 from 2-(3H-spiro[isobenzofuran-1,4'-piperidine]-1'-yl)thiazol-4(5H)-one and 1,1,1,3,3,3-hexafluoropropan-2-one. MS m/e: 437.4 ([M+H]+)

Example 112

(5E/Z)-5-[1-(2,4-dimethyl-1,3-thiazol-5-yl)ethylidene]-2-(1'H,3H-spiro[2-benzofuran-1,4'-piperidin]-1'-yl)-1,3-thiazol-4(5H)-one The title compound was obtained as light brown solid in 8% yield according to the general procedure 6 from 2-(3H-spiro[isobenzofuran-1,4'-piperidine]-1'-yl)thiazol-4(5H)-one and 1-(2,4-dimethylthiazol-5-yl)ethanone. MS m/e: 426.5 ([M+H]+)

Example 113

5-(1,3-dichloropropan-2-ylidene)-2-(1'H,3H-spiro[2-benzofuran-1,4'-piperidin]-1'-yl)-1,3-thiazol-4(5H)-one The title compound was obtained as light brown solid in 3% yield according to the general procedure 6 from 2-(3H-spiro[isobenzofuran-1,4'-piperidine]-1'-yl)thiazol-4(5H)-one and 1,3-dichloropropan-2-one. MS m/e: 397.4 ([M]+)

Example 114

5-(heptan-4-ylidene)-2-(1'H,3H-spiro[2-benzofuran-1,4'-piperidin]-1'-yl)-1,3-thiazol-4(5H)-one The title compound was obtained as light brown solid in 3% yield according to the general procedure 6 from 2-(3H-spiro[isobenzofuran-1,4'-piperidine]-1'-yl)thiazol-4(5H)-one and heptan-4-one. MS m/e: 385.6 ([M+H]+)

Example 115

5-(dicyclopropylmethylidene)-2-(1'H,3H-spiro[2-benzofuran-1,4'-piperidin]-1'-yl)-1,3-thiazol-4(5H)-one The title compound was obtained as off-white solid in 91% yield according to the general procedure 6 from 2-(3H-spiro[isobenzofuran-1,4'-piperidine]-1'-yl)thiazol-4(5H)-one and dicyclopropylmethanone. MS m/e: 381.5 ([M+H]+)

Example 116

5-(2,6-dimethylheptan-4-ylidene)-2-(1'H,3H-spiro[2-benzofuran-1,4'-piperidin]-1'-yl)-1,3-thiazol-4(5H)-one The title compound was obtained as light yellow oil in 28% yield according to the general procedure 6 from 2-(3H-spiro[isobenzofuran-1,4'-piperidine]-1'-yl)thiazol-4(5H)-one and 2,6-dimethylheptan-4-one. MS m/e: 413.5 ([M+H]+)

Example 117

(5E/Z)-5-[1-(1H-imidazol-5-yl)ethylidene]-2-(1'H,3H-spiro[2-benzofuran-1,4'-piperidin]-1'-yl)-1,3-thiazol-4(5H)-one The title compound was obtained as light yellow solid in 77% yield according to the general procedure 6 from 2-(3H-spiro[isobenzofuran-1,4'-piperidine]-1'-yl)thiazol-4(5H)-one and 1-(1H-imidazol-5-yl)ethanone. MS m/e: 381.5 ([M+H]+)

Example 118

5-(dicyclopentylmethylidene)-2-(1'H,3H-spiro[2-benzofuran-1,4'-piperidin]-1'-yl)-1,3-thiazol-4(5H)-one The title compound was obtained as light brown oil in 9% yield according to the general procedure 6 from 2-(3H-spiro[isobenzofuran-1,4'-piperidine]-1'-yl)thiazol-4(5H)-one and dicyclopentylmethanone. MS m/e: 437.6 ([M+H]+)

Example 119

5-[di(pyridin-3-yl)methylidene]-2-(1'H,3H-spiro[2-benzofuran-1,4'-piperidin]-1'-yl)-1,3-thiazol-4(5H)-one The title compound was obtained as brown solid in 34% yield according to the general procedure 6 from 2-(3H-spiro[isobenzofuran-1,4'-piperidine]-1'-yl)thiazol-4(5H)-one and dipyridin-3-ylmethanone. MS m/e: 455.5 ([M+H]+)

Example 120

5-(2,4-dimethylpentan-3-ylidene)-2-(1'H,3H-spiro[2-benzofuran-1,4'-piperidin]-1'-yl)-1,3-thiazol-4(5H)-one The title compound was obtained as light brown solid in 2% yield according to the general procedure 6 from 2-(3H-spiro[isobenzofuran-1,4'-piperidine]-1'-yl)thiazol-4(5H)-one and 2,4-dimethylpentan-3-one. MS m/e: 385.5 ([M+H]+)

Example 121

(5E/Z)-5-[1-(methylsulfonyl)propan-2-ylidene]-2-(1'H,3H-spiro[2-benzofuran-1,4'-piperidin]-1'-yl)-1,3-thiazol-4(5H)-one The title compound was obtained as light yellow solid in 62% yield according to the general procedure 6 from 2-(3H- spiro[isobenzofuran-1,4'-piperidine]-1'-yl)thiazol-4(5H)-one and 1-(methylsulfonyl)propan-2-one. MS m/e: 407.5 ([M+H]+)

Example 122

5-(di-1H-pyrrol-2-ylmethylidene)-2-(1'H,3H-spiro[2-benzofuran-1,4'-piperidin]-1'-yl)-1,3-thiazol-4(5H)-one The title compound was obtained as yellow solid in 30% yield according to the general procedure 6 from 2-(3H-spiro[isobenzofuran-1,4'-piperidine]-1'-yl)thiazol-4(5H)-one and di(1H-pyrrol-2-yl)methanone. MS m/e: 431.6 ([M+H]+)

Example 123

(5E)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one The title compound was obtained as off-white solid in 71% yield according to the general procedure 6 from 2-(3H-spiro[isobenzofuran-1,4'-piperidine]-1'-yl)thiazol-4(5H)-one and 2-(tert-butyldimethylsilyloxy)-1-phenylethanone. MS m/e: 521.5 ([M+H]+)

Example 124

(5E)-5-(2-hydroxy-1-phenylethylidene)-2-(1'H,3H-spiro[2-benzofuran-1,4'-piperidin]-1'-yl)-1,3-thiazol-4(5H)-one A suspension of (5E)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one (100.0 mg, 192 μmol) and PPTS (Pyridinium para-toluene sulfonate) (24.1 mg, 96 μmol) in methanol (1 ml) and dichloromethane (1 ml) was stirred for 2 h, then concentrated to dryness. The residue was diluted with dichloromethane and filtered through glass fiber paper. Concentration of the filtrate to dryness gave the title compound (75.3 mg, 185 mol, 97% yield) as off-white solid.
MS m/e: 407.5 ([M+H]+)

Example 125

5-(dicyclohexylmethylidene)-2-(1'H,3H-spiro[2-benzofuran-1,4'-piperidin]-1'-yl)-1,3-thiazol-4(5H)-one The title compound was obtained as light yellow solid in 4% yield according to the general procedure 6 from 2-(3H-spiro[isobenzofuran-1,4'-piperidine]-1'-yl)thiazol-4(5H)-one and dicyclohexylmethanone. MS m/e: 465.2 ([M+H]+)

Example 126

(5Z)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one The title compound was obtained as light brown solid in 13% yield according to the general procedure 6 from 2-(3H-spiro[isobenzofuran-1,4'-piperidine]-1'-yl)thiazol-4(5H)-one and 2-(tert-butyldimethylsilyloxy)-1-phenylethanone. MS m/e: 521.8 ([M+H]+)

Example 127

(5Z)-5-(2-hydroxy-1-phenylethylidene)-2-(1'H,3H-spiro[2-benzofuran-1,4'-piperidin]-1'-yl)-1,3-thiazol-4(5H)-one A suspension of (5Z)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one (30.0 mg, 57.6 μmol) and PPTS (14.5 mg, 57.6 μmol) in methanol (300 μl) and dichloromethane (300 μl) was stirred for 24 h, then concentrated to dryness. The residue was diluted with dichloromethane and filtered through glass fiber paper. Purification by flash chromatography (silica gel, 4 g, 0% to 70% ethyl acetate in heptane) gave the title compound (6.7 mg, 16.5 μmol, 29% yield) as light yellow solid.
MS m/e: 407.5 ([M+H]+)

Example 128

(5Z)-5-(cyclopent-2-en-1-ylidene)-2-(1'H,3H-spiro[2-benzofuran-1,4'-piperidin]-1'-yl)-1,3-thiazol-4(5H)-one The title compound was obtained as light yellow solid in 5% yield according to the general procedure 6 from 2-(3H-spiro[isobenzofuran-1,4'-piperidine]-1'-yl)thiazol-4(5H)-one and cyclopent-3-enone. MS m/e: 353.1 ([M+H]+)

Example 129

(5E)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one The title compound was obtained as white solid in 36% yield according to the general procedure 6 from 2-(3H-spiro[isobenzofuran-1,4'-piperidine]-1'-yl)thiazol-4(5H)-one and 2-(tert-butyldimethylsilyloxy)-1-(6-chloropyridin-3-yl)ethanone. MS m/e: 556.2 ([M]+)

Example 130

(5E)-5-[1-(6-chloropyridin-3-yl)-2-hydroxyethylidene]-2-(1'H,3H-spiro[2-benzofuran-1,4'-piperidin]-1'-yl)-1,3-thiazol-4(5H)-one A suspension of (5E)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one (52.0 mg, 93.5 μmol) and PPTS (35.2 mg, 140 μmol) in methanol (450 μl) and dichloromethane (450 μl) was stirred for 4 h at 50° C., then concentrated to dryness. The residue was diluted with dichloromethane and filtered through glass fiber paper. The filtrate was concentrated to dryness to give the title compound (40.0 mg, 90.5 μmol, 97% yield) as white foam. MS m/e: 442.3 ([M+H]+)

Example 131

(5Z)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one The title compound was obtained as pink gum in 37% yield according to the general procedure 6 from 2-(3H-spiro[isobenzofuran-1,4'-piperidine]-1'-yl)thiazol-4(5H)-one and 2-(tert-butyldimethylsilyloxy)-1-(6-chloropyridin-3-yl) ethanone. MS m/e: 556.2 ([M]+)

Example 132

(5E)-5-[1-(6-chloropyridin-3-yl)-2-methylpropylidene]-2-(1'H,3H-spiro[2-benzofuran-1,4'-piperidin]-1'-yl)-1,3-thiazol-4(5H)-one The title compound was obtained as off-white solid in 59% yield according to the general procedure 6 from 2-(3H-spiro[isobenzofuran-1,4'-piperidine]-1'-yl)thiazol-4(5H)-one and 1-(6-chloropyridin-3-yl)-2-methylpropan-1-one. MS m/e: 454.1 ([M+H]+)

Example 133

(5Z)-5-[1-(6-chloropyridin-3-yl)propylidene]-2-(1'H,3H-spiro[2-benzofuran-1,4'-piperidin]-1'-yl)-1,3-thiazol-4(5H)-one The title compound was obtained as yellow solid in 7% yield according to the general procedure 6 from 2-(3H-spiro[isobenzofuran-1,4'-piperidine]-1'-yl)thiazol-4(5H)-one and 1-(6-chloropyridin-3-yl)propan-1-one. MS m/e: 440.1 ([M+H]+)

Example 134

(5E)-5-[1-(6-chloropyridin-3-yl)propylidene]-2-(1'H,3H-spiro[2-benzofuran-1,4'-piperidin]-1'-yl)-1,3-thiazol-4(5H)-one The title compound was obtained as yellow solid in 7% yield according to the general procedure 6 from 2-(3H-spiro[isobenzofuran-1,4'-piperidine]-1'-yl)thiazol-4(5H)-one and 1-(6-chloropyridin-3-yl)propan-1-one. MS m/e: 440.1 ([M+H]+)

Example 135

1'-{(5Z)-5-[1-(6-methylpyridin-3-yl)ethylidene]-4-oxo-4,5-dihydro-1,3-thiazol-2-yl}-3H-spiro[2-benzofuran-1,4'-piperidin]-3-one The title compound was obtained as light yellow solid in 46% yield according to the general procedure 6 from 1'-(4-oxo-4,5-dihydrothiazol-2-yl)-3H-spiro[isobenzofuran-1,4'-piperidin]-3-one and 1-(6-methylpyridin-3-yl)ethanone. MS m/e: 420.5 ([M+H]+)

Example 136

1'-{(5E)-5-[1-(6-methylpyridin-3-yl)ethylidene]-4-oxo-4,5-dihydro-1,3-thiazol-2-yl}-3H-spiro[2-benzofuran-1,4'-piperidin]-3-one The title compound was obtained as orange solid in 33% yield according to the general procedure 6 from 1'-(4-oxo-4,5-dihydrothiazol-2-yl)-3H-spiro[isobenzofuran-1,4'-piperidin]-3-one and 1-(6-methylpyridin-3-yl)ethanone. MS m/e: 420.6 ([M+H]+)

Example 137

1'-{(5Z)-5-[1-(6-chloropyridin-3-yl)ethylidene]-4-oxo-4,5-dihydro-1,3-thiazol-2-yl}-3H-spiro[2-benzofuran-1,4'-piperidin]-3-one The title compound was obtained as off-white solid in 6% yield according to the general procedure 6 from 1'-(4-oxo-4,5-dihydrothiazol-2-yl)-3H-spiro[isobenzofuran-1,4'-piperidin]-3-one and 1-(6-chloropyridin-3-yl)ethanone. MS m/e: 440.5 ([M+H]+)

Example 138

1'-{(5E)-5-[1-(6-chloropyridin-3-yl)ethylidene]-4-oxo-4,5-dihydro-1,3-thiazol-2-yl}-3H-spiro[2-benzofuran-1,4'-piperidin]-3-one The title compound was obtained as light yellow solid in 34% yield according to the general procedure 6 from 1'-(4-oxo-4,5-dihydrothiazol-2-yl)-3H-spiro[isobenzofuran-1,4'-piperidin]-3-one and 1-(6-chloropyridin-3-yl)ethanone. MS m/e: 440.5 ([M+H]+)

Example 139

1'-[5-(dicyclopropylmethylidene)-4-oxo-4,5-dihydro-1,3-thiazol-2-yl]-3H-spiro[2-benzofuran-1,4'-piperidin]-3-one The title compound was obtained as light yellow solid in 79% yield according to the general procedure 6 from 1'-(4-oxo-4,5-dihydrothiazol-2-yl)-3H-spiro[isobenzofuran-1,4'-piperidin]-3-one and dicyclopropylmethanone. MS m/e: 395.5 ([M+H]+)

Example 140

1'-[(5E)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one The title compound was obtained as off-white solid in 33% yield according to the general procedure 6 from 1'-(4-oxo-4,5-dihydrothiazol-2-yl)-3H-spiro[isobenzofuran-1,4'-piperidin]-3-one and 2-(tert-butyldimethylsilyloxy)-1-phenylethanone. MS m/e: 535.6 ([M+H]+)

Example 141

1'-[(5Z)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one The title compound was obtained as yellow solid in 12% yield according to the general procedure 6 from 1'-(4-oxo-4,5-dihydrothiazol-2-yl)-3H-spiro[isobenzofuran-1,4'-piperidin]-3-one and 2-(tert-butyldimethylsilyloxy)-1-phenylethanone. MS m/e: 535.6 ([M+H]+)

Example 142

1'-[(5Z)-5-(2-hydroxy-1-phenylethylidene)-4-oxo-4,5-dihydro-1,3-thiazol-2-yl]-3H-spiro[2-benzofuran-1,4'-piperidin]-3-one A suspension of 1'-[(5Z)-5-(2-{[tert-butyl(dimethyl)silyl]oxy}-1-phenylethylidene)-4-oxo-4,5-dihydro-1,3-thiazol-2- yl]-3H-spiro[2-benzofuran-1,4'-piperidin]-3-one (15.0 mg, 28.1 μmol) and PPTS (7.1 mg, 28.1 μmol) in methanol (150 μl) and dichloromethane (150 μl) was stirred for 24 h at 20° C., then concentrated to dryness. Purification by flash chromatography (silica gel, 4 g, 0% to 70% ethyl acetate in heptane) gave the title compound (2.6 mg, 6.2 μmol, 22% yield) as off-white solid. MS m/e: 421.1 ([M+H]+)

Example 143

1'-[(5E)-5-(2-hydroxy-1-phenylethylidene)-4-oxo-4,5-dihydro-1,3-thiazol-2-yl]-3H-spiro[2-benzofuran-1,4'-piperidin]-3-one A suspension of 1'-[(5Z)-5-(2-hydroxy-1-phenylethylidene)-4-oxo-4,5-dihydro-1,3-thiazol-2-yl]-3H-spiro[2-benzofuran-1,4'-piperidin]-3-one (85.0 mg, 159 μmol) and PPTS (20 mg, 79.5 μmol) in methanol (850 μl) and dichloromethane (850 μl) was stirred for 8 h at 40° C., then concentrated to dryness. Purification by flash chromatography (silica gel, 4 g, 0% to 70% ethyl acetate in heptane) gave the title compound (66 mg, 98% yield) as off-white solid.
MS m/e: 421.5 ([M+H]+)

Example 144

1'-{(5E)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one The title compound was obtained as light yellow solid in 38% yield according to the general procedure 6 from 1'-(4-oxo-4,5-dihydrothiazol-2-yl)-3H-spiro[isobenzofuran-1,4'-piperidin]-3-one and 2-(tert-butyldimethylsilyloxy)-1-(6-chloropyridin-3-yl)ethanone.
MS m/e: 570.5 ([M]+)

Example 145

1'-{(5E)-5-[1-(6-chloropyridin-3-yl)-2-hydroxyethylidene]-4-oxo-4,5-dihydro-1,3-thiazol-2-yl}-3H-spiro[2-benzofuran-1,4'-piperidin]-3-one A suspension of 1'-{(5E)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one (60.0 mg, 105.0 μmol) and PPTS (13.2 mg, 52.6 μmol) in methanol (600 μl) and dichloromethane (600 μl) was stirred for 24 h at 20° C. and for 8 h at 40° C., then concentrated to dryness. The residue was diluted with dichloromethane and filtered through glass fiber paper. Concentration of the filtrate to dryness gave the title compound (16.9 mg, 37.0 μmol, 35% yield) as off-white solid. MS m/e: 456.6 ([M+H]+)

Example 146

1'-{(5Z)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one The title compound was obtained as light brown solid in 29% yield according to the general procedure 6 from 1'-(4-oxo-4,5-dihydrothiazol-2-yl)-3H-spiro[isobenzofuran-1,4'-piperidin]-3-one and 2-(tert-butyldimethylsilyloxy)-1-(6-chloropyridin-3-yl)ethanone.
MS m/e: 570.5 ([M]+)

Example 147

1'-{(5Z)-5-[1-(6-chloropyridin-3-yl)-2-hydroxyethylidene]-4-oxo-4,5-dihydro-1,3-thiazol-2-yl}-3H-spiro[2-benzofuran-1,4'-piperidin]-3-one A suspension of 1'-{(5Z)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one (45.0 mg, 78.9 μmol) and PPTS (29.8 mg, 118.0 μmol) in methanol (450 μl) and dichloromethane (450 μl) was stirred for 24 h at 50° C., then concentrated to dryness. The residue was diluted with dichloromethane and filtered through glass fiber paper. The filtrate was concentrated to dryness. Purification by flash chromatography (silica gel, 4 g, 0% to 70% ethyl acetate in heptane) gave the title compound (12.1 mg, 26.5 μmol, 34% yield) as off-white solid.
MS m/e: 456.6 ([M+H]+)

Example 148

1'-{(5E)-5-[1-(6-chloropyridin-3-yl)-2-methylpropylidene]-4-oxo-4,5-dihydro-1,3-thiazol-2-yl}-3H-spiro[2-benzofuran-1,4'-piperidin]-3-one The title compound was obtained as brown oil in 38% yield according to the general procedure 6 from 1'-(4-oxo-4,5-dihydrothiazol-2-yl)-3H-spiro[isobenzofuran-1,4'-piperidin]-3-one and 1-(6-chloropyridin-3-yl)-2-methylpropan-1-one. MS m/e: 468.6 ([M+H]+)

Example 149

1'-{(5E)-5-[1-(6-chloropyridin-3-yl)propylidene]-4-oxo-4,5-dihydro-1,3-thiazol-2-yl}-3H-spiro[2-benzofuran-1,4'-piperidin]-3-one The title compound was obtained as orange solid in 59% yield according to the general procedure 6 from 1'-(4-oxo-4,5-dihydrothiazol-2-yl)-3H-spiro[isobenzofuran-1,4'-piperidin]-3-one and 1-(6-chloropyridin-3-yl)propan-1-one. MS m/e: 454.6 ([M+H]+)

Example 150

1'-{(5Z)-5-[1-(6-chloropyridin-3-yl)propylidene]-4-oxo-4,5-dihydro-1,3-thiazol-2-yl}-3H-spiro[2-benzofuran-1,4'-piperidin]-3-one The title compound was obtained as colorless oil in 3% yield according to the general procedure 6 from 1'-(4-oxo-4,5-dihydrothiazol-2-yl)-3H-spiro[isobenzofuran-1,4'-piperidin]-3-one and 1-(6-chloropyridin-3-yl)propan-1-one. MS m/e: 454.6 ([M+H]+)

Example 151

(5Z)-5-(1-phenylethylidene)-2-(1'H,3H-spiro[2-benzofuran-1,4'-piperidin]-1'-yl)-1,3-thiazol-4(5H)-one The title compound was obtained as off-white solid in 18% yield according to the general procedure 6 from 2-(3H- spiro[isobenzofuran-1,4'-piperidine]-1'-yl)thiazol-4(5H)-one and acetophenone. MS m/e: 391.5 ([M+H]+)

Example 152

(5E)-5-(1-phenylethylidene)-2-(1'H,3H-spiro[2-benzofuran-1,4'-piperidin]-1'-yl)-1,3-thiazol-4(5H)-one The title compound was obtained as light yellow oil in 1% yield according to the general procedure 6 from 2-(3H-spiro[isobenzofuran-1,4'-piperidine]-1'-yl)thiazol-4(5H)-one and acetophenone. MS m/e: 391.5 ([M+H]+)

Example 153

(5E)-5-[1-(6-methylpyridin-3-yl)ethylidene]-2-(1'H,3H-spiro[2-benzofuran-1,4'-piperidin]-1'-yl)-1,3-thiazol-4(5H)-one The title compound was obtained as light orange oil in 27% yield according to the general procedure 6 from 2-(3H-spiro[isobenzofuran-1,4'-piperidine]-1'-yl)thiazol-4(5H)-one and 1-(6-methylpyridin-3-yl)ethanone. MS m/e: 406.6 ([M+H]+)

Example 154

(5E)-5-[1-(4-chlorophenyl)-2-methylpropylidene]-2-(1'H,3H-spiro[2-benzofuran-1,4'-piperidin]-1'-yl)-1,3-thiazol-4(5H)-one The title compound was obtained as white solid in 46% yield according to the general procedure 6 from 2-(3H-spiro[isobenzofuran-1,4'-piperidine]-1'-yl)thiazol-4(5H)-one and 1-(4-chlorophenyl)-2-methylpropan-1-one. MS m/e: 453.4 ([M+H]+)

Example 155

(5E)-5-[1-(3-methylpyridin-2-yl)ethylidene]-2-(1'H,3H-spiro[2-benzofuran-1,4'-piperidin]-1'-yl)-1,3-thiazol-4(5H)-one The title compound was obtained as light yellow oil in 4% yield according to the general procedure 6 from 2-(3H-spiro[isobenzofuran-1,4'-piperidine]-1'-yl)thiazol-4(5H)-one and 1-(3-methylpyridin-2-yl)ethanone. MS m/e: 406.4 ([M+H]+)

Example 156

1'-[(5Z)-4-oxo-5-(1-phenylethylidene)-4,5-dihydro-1,3-thiazol-2-yl]-3H-spiro[2-benzofuran-1,4'-piperidin]-3-one The title compound was obtained as green solid in 67% yield according to the general procedure 6 from 1'-(4-oxo-4,5-dihydrothiazol-2-yl)-3H-spiro[isobenzofuran-1,4'-piperidin]-3-one and acetophenone. MS m/e: 405.5 ([M+H]+)

Example 157

1'-[(5E)-4-oxo-5-(1-phenylethylidene)-4,5-dihydro-1,3-thiazol-2-yl]-3H-spiro[2-benzofuran-1,4'-piperidin]-3-one The title compound was obtained as yellow solid in 2% yield according to the general procedure 6 from 1'-(4-oxo-4,5-dihydrothiazol-2-yl)-3H-spiro[isobenzofuran-1,4'-piperidin]-3-one and acetophenone. MS m/e: 405.5 ([M+H]+)

Example 158

(5Z)-5-[1-(3-fluoropyridin-4-yl)ethylidene]-2-(1'H,3H-spiro[2-benzofuran-1,4'-piperidin]-1'-yl)-1,3-thiazol-4(5H)-one The title compound was obtained as off-white solid in 7% yield according to the general procedure 6 from 2-(3H-spiro[isobenzofuran-1,4'-piperidine]-1'-yl)thiazol-4(5H)-one and 1-(3-fluoropyridin-2-yl)ethanone. MS m/e: 410.1 ([M+H]+)

Example 159 tert-butyl {(2E/Z)-2-[4-oxo-2-(1'H,3H-spiro[2-benzofuran-1,4'-piperidin]-1'-yl)-1,3-thiazol-5(4H)-ylidene]-2-phenylethyl}carbamate The title compound was obtained as orange solid in 4% yield according to the general procedure 6 from 2-(3H-spiro[isobenzofuran-1,4'-piperidine]-1'-yl)thiazol-4(5H)-one and tert-butyl 2-oxo-2-phenylethyl carbamate. MS m/e: 506.2 ([M+H]+)

Example 160

(5E/Z)-5-(2-amino-1-phenylethylidene)-2-(1'H,3H-spiro[2-benzofuran-1,4'-piperidin]-1'-yl)-1,3-thiazol-4(5H)-one trifluoroacetate To a solution of tert-butyl {(2E/Z)-2-[4-oxo-2-(1'H,3H-spiro[2-benzofuran-1,4'-piperidin]-1'-yl)-1,3-thiazol-5(4H)-ylidene]-2-phenylethyl}carbamate (6 mg, 11.9 µmol) in dichloromethane (240 µl) at 0-5° C. was added trifluoroacetic acid (240 µl, 3.12 mmol). The mixture was stirred at 22° C. for 1 hr. Concentration to dryness gave the title compound (6 mg, 11.5 µmol, 97% yield) as yellow oil. MS m/e: 406.5 ([M+H]+)

Example 161

5-(1,3-dihydro-2H-inden-2-ylidene)-2-(1'H,3H-spiro[2-benzofuran-1,4'-piperidin]-1'-yl)-1,3-thiazol-4(5H)-one The title compound was obtained as brown oil in 1% yield according to the general procedure 6 from 2-(3H-spiro[isobenzofuran-1,4'-piperidine]-1'-yl)thiazol-4(5H)-one and 1H-inden-2(3H)-one. MS m/e: 403.5 ([M+H]+)

Example 162

(5E/Z)-5-[1-(6-chloropyridin-3-yl)ethylidene]-2-(1'H,7H-spiro[furo[3,4-b]pyridine-5,4'-piperidin]-1'-yl)-1,3-thiazol-4(5H)-one The title compound was obtained as yellow solid in 71% yield according to the general procedure 6 from 2-(7H-spiro

[furo[3,4-b]pyridine-5,4'-piperidine]-1'-yl)thiazol-4(5H)-one and 1-(6-chloropyridin-3-yl)ethanone. MS m/e: 427.1 ([M+H]+)

Example 163

5-(1,3-dimethoxypropan-2-ylidene)-2-(1'H,7H-spiro[furo[3,4-b]pyridine-5,4'-piperidin]-1'-yl)-1,3-thiazol-4(5H)-one The title compound was obtained as orange gum in 26% yield according to the general procedure 6 from 2-(7H-spiro[furo[3,4-b]pyridine-5,4'-piperidine]-1'-yl)thiazol-4(5H)-one and 1,3-dimethoxypropan-2-one. MS m/e: 390.1 ([M+H]+)

Example 164

(5E/Z)-5-(2-methoxycyclohexylidene)-2-(1'H,7H-spiro[furo[3,4-b]pyridine-5,4'-piperidin]-1'-yl)-1,3-thiazol-4(5H)-one The title compound was obtained as yellow oil in 96% yield according to the general procedure 6 from 2-(7H-spiro[furo[3,4-b]pyridine-5,4'-piperidine]-1'-yl)thiazol-4(5H)-one and 2-methoxycyclohexanone. MS m/e: 400.1 ([M+1-1]+)

Example 165

(5E/Z)-5-[1-(pyridin-3-yl)ethylidene]-2-(1'H,7H-spiro[furo[3,4-b]pyridine-5,4'-piperidin]-1'-yl)-1,3-thiazol-4(5H)-one The title compound was obtained as light yellow solid in 37% yield according to the general procedure 6 from 2-(7H-spiro[furo[3,4-b]pyridine-5,4'-piperidine]-1'-yl)thiazol-4(5H)-one and 1-(pyridin-3-yl)ethanone. MS m/e: 393.1 ([M+H]+)

Example 166

(5E/Z)-5-[1-(6-methylpyridin-3-yl)ethylidene]-2-(1'H,7H-spiro[furo[3,4-b]pyridine-5,4'-piperidin]-1'-yl)-1,3-thiazol-4(5H)-one The title compound was obtained as orange oil in 100% yield according to the general procedure 6 from 2-(7H-spiro[furo[3,4-b]pyridine-5,4'-piperidine]-1'-yl)thiazol-4(5H)-one and 1-(6-methylpyridin-3-yl)ethanone. MS m/e: 407.1 ([M+H]+)

Example 167

(5E/Z)-5-[1-(2,4-dimethyl-1,3-oxazol-5-yl)ethylidene]-2-(1'H,7H-spiro[furo[3,4-b]pyridine-5,4'-piperidin]-1'-yl)-1,3-thiazol-4(5H)-one The title compound was obtained as orange solid in 72% yield according to the general procedure 6 from 2-(7H-spiro[furo[3,4-b]pyridine-5,4'-piperidine]-1'-yl)thiazol-4(5H)-one and 1-(2,4-dimethyloxazol-5-yl)ethanone. MS m/e: 411.1 ([M+H]+)

Example 168

(5E/Z)-5-(1H-isochromen-4(3H)-ylidene)-2-(1'H,7H-spiro[furo[3,4-b]pyridine-5,4'-piperidin]-1'-yl)-1,3-thiazol-4(5H)-one The title compound was obtained as yellow solid in 76% yield according to the general procedure 6 from 2-(7H-spiro[furo[3,4-b]pyridine-5,4'-piperidine]-1'-yl)thiazol-4(5H)-one and isochroman-4-one. MS m/e: 420.1 ([M+H]+)

Example 169

(5Z)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one The title compound was obtained as orange solid in 8% yield according to the general procedure 6 from 2-(3H-spiro[isobenzofuran-1,4'-piperidine]-1'-yl)thiazol-4(5H)-one and 2,2,2-trideuterio-1-(6-methylpyridin-3-yl)ethanone. MS m/e: 409.7 ([M+H]+)

Example 170

(5E)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one The title compound was obtained as orange solid in 17% yield according to the general procedure 6 from 2-(3H-spiro[isobenzofuran-1,4'-piperidine]-1'-yl)thiazol-4(5H)-one and 2,2,2-trideuterio-1-(6-methylpyridin-3-yl)ethanone. MS m/e: 408.7 ([M+H]+)

Example 171

(5Z)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one The title compound was obtained as orange oil in 13% yield according to the general procedure 6 from 2-(3H-spiro[isobenzofuran-1,4'-piperidine]-1'-yl)thiazol-4(5H)-one and 1-(4-chlorophenyl)-2,2,2-trideuterioethanone. MS m/e: 429.5 ([M+H]+)

Example 172

(5E)-5-[1-(6-chloropyridin-3-yl($^2$H$_3$)ethylidene]-2-(1'H,3H-spiro[2-benzofuran-1,4'-piperidin]-1'-yl)-1,3-thiazol-4(5H)-one The title compound was obtained as yellow oil in 17% yield according to the general procedure 6 from 2-(3H-spiro[isobenzofuran-1,4'-piperidine]-1'-yl)thiazol-4(5H)-one and 1-(4-chlorophenyl)-2,2,2-trideuterioethanone. MS m/e: 429.5 ([M+H]+)

Example 173

(5Z)-5-[1-phenyl($^2$H$_3$)ethylidene]-2-(1'H,3H-spiro[2-benzofuran-1,4'-piperidin]-1'-yl)-1,3-thiazol-4(5H)-one The title compound was obtained as yellow solid in 11% yield according to the general procedure 6 from 2-(3H-spiro[isobenzofuran-1,4'-piperidine]-1'-yl)thiazol-4(5H)-one and 2,2,2-trideuterio-1-phenylethanone. MS m/e: 394.7 ([M+H]+)

Example 174

(5E)-5-[1-phenyl($^2$H$_3$)ethylidene]-2-(1'H,3H-spiro[2-benzofuran-1,4'-piperidin]-1'-yl)-1,3-thiazol-4(5H)-one The title compound was obtained as yellow solid in 2% yield according to the general procedure 6 from 2-(3H-spiro[isobenzofuran-1,4'-piperidine]-1'-yl)thiazol-4(5H)-one and 2,2,2-trideuterio-1-phenylethanone. MS m/e: 394.6 ([M+H]+)

[1] Robben, et al. (2006). Am J Physiol Renal Physiol. 291, F257-70, "Cell biological aspects of the vasopressin type-2 receptor and aquaporin 2 water channel in nephrogenic diabetes insipidus"
[2] Neumann (2008). J Neuroendocrinol. 20, 858-65, "Brain oxytocin: a key regulator of emotional and social behaviours in both females and males"
[3] Ebner, et al. (2002). Eur J Neurosci. 15, 384-8., "Forced swimming triggers vasopressin release within the amygdala to modulate stress-coping strategies in rats"
[4] Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety"
[5] Regier, et al. (1998). Br J Psychiatry Suppl. 24-8, "Prevalence of anxiety disorders and their comorbidity with mood and addictive disorders"
[6] Bielsky, et al. (2004). Neuropsychopharmacology. 29, 483-93, "Profound impairment in social recognition and reduction in anxiety-like behavior in vasopressin V1a receptor knockout mice"
[7] Landgraf, et al. (1995). Regul Pept. 59, 229-39., "V1 vasopressin receptor antisense oligodeoxynucleotide into septum reduces vasopressin binding, social discrimination abilities, and anxiety-related behavior in rats"
[8] Yirmiya, et al. (2006). 11, 488-94, "Association between the arginine vasopressin 1a receptor (AVPR1a) gene and autism in a family-based study: mediation by socialization skills"
[9] Thompson, et al. (2004). Psychoneuroendocrinology. 29, 35-48, "The effects of vasopressin on human facial responses related to social communication"
[10] Raskind, et al. (1987). Biol Psychiatry. 22, 453-62, "Antipsychotic drugs and plasma vasopressin in normals and acute schizophrenic patients"
[11] Altemus, et al. (1992). Arch Gen Psychiatry. 49, 9-20, "Abnormalities in the regulation of vasopressin and corticotropin releasing factor secretion in obsessive-compulsive disorder"
[12] Genes, Brain and Behavior (2011) 10: 228-235
[13] Curr. Opin. Neurobiol. 19, 231-234 (2009)
[14] Kalsbeek, A., E. Fliers, M. A. Hofman, D. F. Swaab and R. M. Buijs. 2010. Vasopressin and the output of the hypothalamic biological clock.
[15] Schwartz, W. J., R. J. Coleman and S. M. Reppert. 1983. A daily vasopressin rhythm in rat cerebrospinal fluid. Brain Res 263: 105-12
[16] Groblewski, T. A., A. A. Nunez and R. M. Gold. 1981. Circadian rhythms in vasopressin deficient rats. Brain Res Bull 6: 125-30
[17] Albers, H. E., C. F. Ferris, S. E. Leeman and B. D. Goldman. 1984. Avian pancreatic polypeptide phase shifts hamster circadian rhythms when microinjected into the suprachiasmatic region. Science 223: 833-5
[18] Yoshiaki Yamaguchi, Tom Suzuki, Yasutaka Mizoro, Hiroshi Kori, Kazuki Okada, Yulin Chen, Jean-Michel Fustin, Fumiyoshi Yamazaki, Naoki Mizuguchi, Jing Zhang, Xin Dong, Gozoh Tsujimoto, Yasushi Okuno, Masao Doi, Hitoshi Okamura. Mice Genetically Deficient in Vasopressin V1a and V1b Receptors Are Resistant to Jet Lag. (2013) Science, 342: 85-90
[19] Compendium of Chemical Terminology, 2nd, A. D. McNaught & A. Wilkinson (Eds). Blackwell Scientific Publications, Oxford (1997)

The invention claimed is:
1. A compound of formula I,

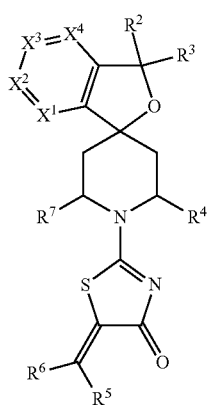

wherein
$X^1$ C—$R^1$ or N;
$X^2$ C—$R^1$ or N;
$X^3$ C—$R^1$ or N;
$X^4$ C—$R^1$ or N;
whereby
i) one of $X^1$, $X^2$, $X^3$ is C—$R^1$ and $X^4$ is N,
ii) each of $X^1$, $X^2$, $X^3$ and $X^4$ is C—$R^1$;
$R^1$ each separately is selected from the group consisting of hydrogen, halogen, hydroxy, $C_{1-6}$-alkyl and $C_{1-6}$-alkoxy;
$R^2$ is selected from the group consisting of hydrogen and $C_{1-6}$-alkyl;
$R^3$ is selected from the group consisting of hydrogen and $C_{1-6}$-alkyl;
or $R^2$ and $R^3$ together are =O;
$R^4$ is hydrogen;
$R^5$ is selected from the group consisting of
i) hydrogen,
ii) $C_{3-7}$-cycloalkyl,
iii) $C_{3-7}$-cycloalkyl substituted by one or more substituents individually selected from halogen and $C_{1-6}$-alkyl,
iv) $C_{1-6}$-alkyl,
v) $C_{1-6}$-alkyl substituted by one or more substituents individually selected from amino, halogen, hydroxy, $C_{1-6}$-alkoxy, —O—C(=O)—$C_{1-6}$-alkyl, NH(C=O)O—$C_{1-6}$-alkyl and —O—Si($C_{1-6}$-alkyl)$_3$,
vi) aryl,
vii) aryl substituted by one or more substituents individually selected from halogen and $C_{1-6}$-alkyl,
viii) heteroaryl, and
ix) heteroaryl substituted by one or more substituents individually selected from halogen and $C_{1-6}$-alkyl;
$R^6$ is selected from the group consisting of
i) $C_{1-6}$-alkyl,
ii) $C_{1-6}$-alkyl substituted by one or more substituents individually selected from amino, halogen, $C_{1-6}$-alkoxy, —O—C(=O)$C_{1-6}$-alkyl, N($C_{1-6}$-alkyl)$_2$, NH(C=O)O—$C_{1-6}$-alkyl, SO$_2$—$C_{1-6}$-alkyl and —O—Si($C_{1-6}$-alkyl)$_3$;
iii) $C_{2-6}$-alkenyl
iv) aryl,
v) aryl substituted by one or more substituents individually selected from halogen and $C_{1-6}$-alkyl;
vi) $C_{3-9}$-cycloalkyl,
vii) $C_{3-9}$-cycloalkyl substituted by one or more substituents individually selected from —(C=O)O—$C_{1-6}$-alkyl, oxo, $C_{1-6}$-alkoxy and $C_{1-6}$-alkyl;
viii) heterocyclyl,
ix) heteroaryl, and
x) heteroaryl substituted by one or more substituents individually selected from halogen, $C_{1-6}$-alkoxy and $C_{1-6}$-alkyl;
or $R^5$ and $R^6$ together are selected from the group consisting of
i) $C_{3-9}$-cycloalkyl, optionally fused with one or two phenyl,
ii) $C_{3-9}$-cycloalkyl, optionally fused with phenyl, wherein the phenyl moiety is substituted by one or more substituents individually selected from halogen, hydroxy, (C=O)O—$C_{1-6}$-alkyl, $C_{1-6}$-alkoxy and $C_{1-6}$-alkyl,
iii) $C_{3-6}$-cycloalkenyl,
iv) heterocyclyl, optionally fused with one or two phenyl, and
v) heterocyclyl, optionally fused with phenyl, wherein the heterocyclyl moiety is substituted by one or more substituents individually selected from oxo, (C=O)O—$C_{1-6}$-alkyl and SO$_2$—$C_{1-6}$-alkyl or wherein the phenyl moiety is substituted by one or more halogen;
$R^7$ is hydrogen;
or $R^4$ and $R^7$ together are —(CH$_2$)$_n$—; and
n is 2, 3 or 4;
or pharmaceutically acceptable salts thereof.

2. The compound of claim 1, wherein
$X^1$ C—$R^1$ or N;
$X^2$ C—$R^1$ or N;
$X^3$ C—$R^1$;
$X^4$ C—$R^1$ or N;
whereby
i) one of $X^1$ or $X^2$ is C—$R^1$ and $X^4$ is N, or
ii) each of $X^1$, $X^2$, $X^3$ and $X^4$ is C—$R^1$;
$R^1$ each separately is hydrogen;
$R^2$ is hydrogen;
$R^3$ is hydrogen;
or $R^2$ and $R^3$ together are =O;
$R^4$ is hydrogen;
$R^5$ is selected from the group consisting of
i) hydrogen,
ii) $C_{3-7}$-cycloalkyl,
iii) $C_{1-6}$-alkyl,
iv) $C_{1-6}$-alkyl substituted by one or more substituents individually selected from amino, halogen, hydroxy, $C_{1-6}$-alkoxy, —O—C(=O)—$C_{1-6}$-alkyl, NH(C=O)O—$C_{1-6}$-alkyl and —O—Si($C_{1-6}$-alkyl)$_3$,
v) aryl,
vi) aryl substituted by halogen, and
vii) heteroaryl;
$R^6$ is selected from the group consisting of
i) $C_{1-6}$-alkyl,
ii) $C_{1-6}$-alkyl substituted by one or more substituents individually selected from amino, halogen, $C_{1-6}$-alkoxy, —O—C(=O)$C_{1-6}$-alkyl, N($C_{1-6}$-alkyl)$_2$, NH(C=O)O—$C_{1-6}$-alkyl, SO$_2$—$C_{1-6}$-alkyl and —O—Si($C_{1-6}$-alkyl)$_3$;
iii) $C_{2-6}$-alkenyl
iv) aryl,
v) aryl substituted by halogen,
vi) $C_{3-9}$-cycloalkyl,
vii) heterocyclyl,
viii) heteroaryl, and
ix) heteroaryl substituted by one or more substituents individually selected from halogen, $C_{1-6}$-alkoxy and $C_{1-6}$-alkyl;
or $R^5$ and $R^6$ together are selected from the group consisting of
i) $C_{3-9}$-cycloalkyl, optionally fused with one or two phenyl,
ii) $C_{3-9}$-cycloalkyl, optionally fused with phenyl, wherein the phenyl moiety is substituted by one or more substituents individually selected from halogen, hydroxy, and $C_{1-6}$-alkoxy,
iii) $C_{3-6}$-cycloalkenyl,
iv) heterocyclyl, optionally fused with one or two phenyl, and
v) heterocyclyl, optionally fused with phenyl, wherein the heterocyclyl moiety is substituted by one or more substituents individually selected from halogen, oxo, (C=O)O—$C_{1-6}$-alkyl and SO$_2$—$C_{1-6}$-alkyl or wherein the phenyl moiety is substituted by one or more halogen;
$R^7$ is hydrogen;
or $R^4$ and $R^7$ together are —(CH$_2$)$_n$—; and
n is 2.

3. The compound of claim 1, wherein
$X^1$ C—$R^1$ or N;
$X^2$ C—$R^1$ or N;
$X^3$ C—$R^1$;
$X^4$ C—$R^1$ or N;
whereby
i) one of $X^1$, $X^2$, $X^3$ is C—$R^1$ and $X^4$ is N, or
ii) each of $X^1$, $X^2$, $X^3$ and $X^4$ is C—$R^1$;
$R^1$ each separately is hydrogen;
$R^2$ is hydrogen;
$R^3$ is hydrogen;
or $R^2$ and $R^3$ together are =O;
$R^4$ is hydrogen;
$R^5$ is selected from the group consisting of
i) hydrogen,
ii) $C_{1-6}$-alkyl, and
iii) $C_{1-6}$-alkyl substituted by one substituents individually selected from hydroxyl and $C_{1-6}$-alkoxy;
$R^6$ is selected from the group consisting of
i) $C_{1-6}$-alkyl substituted by one $C_{1-6}$-alkoxy;
ii) aryl,
iii) aryl substituted by halogen, and
iv) heteroaryl substituted by one or two substituents individually selected from halogen and $C_{1-6}$-alkyl; and
$R^7$ is hydrogen.

4. The compound of claim 1, wherein
i) $X^1$ is N, $X^2$ is CH, $X^3$ is CH and $X^4$ is CH,
ii) $X^1$ is CH, $X^2$ is CH, $X^3$ is CH and $X^4$ is CH, or
iii) $X^1$ is CH, $X^2$ is CH, $X^3$ is CH and $X^4$ is N.

5. The compound of claim 1, wherein
$X^1$ is CH, $X^2$ is CH, $X^3$ is CH and $X^4$ is CH.

6. The compound of claim 1, wherein $R^2$ is hydrogen and $R^3$ is hydrogen.

7. A compound of formula I according to claim 1, wherein $R^5$ is hydrogen, methyl, —CH$_2$—OCH$_3$, —CH$_2$—OH or —CD$_3$.

8. The compound of claim 1, wherein $R^6$ is phenyl, halogen-phenyl, halogen-pyridinyl, methyl-pyridinyl, dimethyl-oxazolyl or —CH$_2$—OCH$_3$.

9. The compound of claim 1, selected from:
(5E/Z)-5-[1-(4-chlorophenyl)ethylidene]-2-(1'H,3H-spiro[2-benzofuran-1,4'-piperidin]-1'-yl)-1,3-thiazol-4(5H)-one,
(5E/Z)-5-[1-(4-chlorophenyl)ethylidene]-2-(1'H,5H-spiro[furo[3,4-b]pyridine-7,4'-piperidin]-1'-yl)-1,3-thiazol-4(5H)-one,
1'-{(5E/Z)-5-[1-(4-chlorophenyl)ethylidene]-4-oxo-4,5-dihydro-1,3-thiazol-2-yl}-3H-spiro[2-benzofuran-1,4'-piperidin]-3-one,
(5E/Z)-5-[1-(4-chlorophenyl)ethylidene]-2-(1H,1'H-spiro[furo[3,4-c]pyridine-3,4'-piperidin]-1'-yl)-1,3-thiazol-4(5H)-one and (5Z)-5-[1-(4-chlorophenyl)ethylidene]-2-(1H,1'H-spiro[furo[3,4-c]pyridine-3,4'-piperidin]-1'-yl)-1,3-thiazol-4(5H)-one,
8-{(5E/Z)-5-[1-(4-chlorophenyl)ethylidene]-4-oxo-4,5-dihydro-1,3-thiazol-2-yl}-3'H-spiro[8-azabicyclo[3.2.1]octane-3,1'-[2]benzofuran]-3'-one,
(5E/Z)-5-[1-(4-chlorophenyl)ethylidene]-2-(1'H,7H-spiro[furo[3,4-b]pyridine-5,4'-piperidin]-1'-yl)-1,3-thiazol-4(5H)-one,
(5E/Z)-5-[1-(6-methylpyridin-3-yl)ethylidene]-2-(1'H,3H-spiro[2-benzofuran-1,4'-piperidin]-1'-yl)-1,3-thiazol-4(5H)-one,
(5Z)-5-(4-chlorobenzylidene)-2-(1'H,3H-spiro[2-benzofuran-1,4'-piperidin]-1'-yl)-1,3-thiazol-4(5H)-one,
(5Z)-5-benzylidene-2-(1'H,3H-spiro[2-benzofuran-1,4'-piperidin]-1'-yl)-1,3-thiazol-4(5H)-one,
(5E/Z)-5-(5-chloro-2,3-dihydro-1H-inden-1-ylidene)-2-(1'H,3H-spiro[2-benzofuran-1,4'-piperidin]-1'-yl)-1,3-thiazol-4(5H)-one,
(5E/Z)-5-(6-chloro-3,4-dihydronaphthalen-1(2H)-ylidene)-2-(1'H,3H-spiro[2-benzofuran-1,4'-piperidin]-1'-yl)-1,3-thiazol-4(5H)-one,
(5E/Z)-5-[1-(3-chlorophenyl)ethylidene]-2-(1'H,3H-spiro[2-benzofuran-1,4'-piperidin]-1'-yl)-1,3-thiazol-4(5H)-one,
(5E/Z)-5-[1-(4-chlorophenyl)propylidene]-2-(1'H,3H-spiro[2-benzofuran-1,4'-piperidin]-1'-yl)-1,3-thiazol-4(5H)-one,
(5E/Z)-5-[1-(2-chlorophenyl)ethylidene]-2-(1'H,3H-spiro[2-benzofuran-1,4'-piperidin]-1'-yl)-1,3-thiazol-4(5H)-one,
5-(1,3-dimethoxypropan-2-ylidene)-2-(1'H,3H-spiro[2-benzofuran-1,4'-piperidin]-1'-yl)-1,3-thiazol-4(5H)-one,
(5E/Z)-5-(1-phenylethylidene)-2-(1'H,3H-spiro[2-benzofuran-1,4'-piperidin]-1'-yl)-1,3-thiazol-4(5H)-one,
(5Z)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one,
(5E)-5-[1-(4-chlorophenyl)-2,2,2-trifluoroethylidene]-2-(1'H,3H-spiro[2-benzofuran-1,4'-piperidin]-1'-yl)-1,3-thiazol-4(5H)-one,
(5E/Z)-5-(5-chloro-3,4-dihydronaphthalen-1(2H)-ylidene)-2-(1'H,3H-spiro[2-benzofuran-1,4'-piperidin]-1'-yl)-1,3-thiazol-4(5H)-one,
(5E/Z)-5-(7-chloro-3,4-dihydronaphthalen-1(2H)-ylidene)-2-(1'H,3H-spiro[2-benzofuran-1,4'-piperidin]-1'-yl)-1,3-thiazol-4(5H)-one,
(5E/Z)-5-[1-(4-chlorophenyl)-2,2-dimethylpropylidene]-2-(1'H,3H-spiro[2-benzofuran-1,4'-piperidin]-1'-yl)-1,3-thiazol-4(5H)-one,
(5E/Z)-5-[(4-chlorophenyl)(cyclopropyl)methylidene]-2-(1'H,3H-spiro[2-benzofuran-1,4'-piperidin]-1'-yl)-1,3-thiazol-4(5H)-one,
(5E/Z)-5-[1-(4-chlorophenyl)-2-fluoroethylidene]-2-(1'H,3H-spiro[2-benzofuran-1,4'-piperidin]-1'-yl)-1,3-thiazol-4(5H)-one,
(5Z)-5-[1-(4-chlorophenyl)propylidene]-2-(1'H,3H-spiro[2-benzofuran-1,4'-piperidin]-1'-yl)-1,3-thiazol-4(5H)-one,
(5E)-5-[1-(4-chlorophenyl)propylidene]-2-(1'H,3H-spiro[2-benzofuran-1,4'-piperidin]-1'-yl)-1,3-thiazol-4(5H)-one,
(5Z)-5-[1-(4-chlorophenyl)ethylidene]-2-(1'H,3H-spiro[2-benzofuran-1,4'-piperidin]-1'-yl)-1,3-thiazol-4(5H)-one,
(5E)-5-[1-(4-chlorophenyl)ethylidene]-2-(1'H,3H-spiro[2-benzofuran-1,4'-piperidin]-1'-yl)-1,3-thiazol-4(5H)-one,
(5E)-5-(1-cyclohexylethylidene)-2-(1'H,3H-spiro[2-benzofuran-1,4'-piperidin]-1'-yl)-1,3-thiazol-4(5H)-one,
(5Z)-5-(1-cyclohexylethylidene)-2-(1'H,3H-spiro[2-benzofuran-1,4'-piperidin]-1'-yl)-1,3-thiazol-4(5H)-one,
5-(propan-2-ylidene)-2-(1'H,3H-spiro[2-benzofuran-1,4'-piperidin]-1'-yl)-1,3-thiazol-4(5H)-one,
(5Z)-5-[1-(pyridin-4-yl)propylidene]-2-(1'H,3H-spiro[2-benzofuran-1,4'-piperidin]-1'-yl)-1,3-thiazol-4(5H)-one,
(5E)-5-[1-(pyridin-4-yl)propylidene]-2-(1'H,3H-spiro[2-benzofuran-1,4'-piperidin]-1'-yl)-1,3-thiazol-4(5H)-one,
(5Z)-5-[1-(pyridin-4-yl)ethylidene]-2-(1'H,3H-spiro[2-benzofuran-1,4'-piperidin]-1'-yl)-1,3-thiazol-4(5H)-one,
(5E/Z)-5-[1-(1H-pyrrol-2-yl)ethylidene]-2-(1'H,3H-spiro[2-benzofuran-1,4'-piperidin]-1'-yl)-1,3-thiazol-4(5H)-one,
(5Z)-5-[1-(furan-2-yl)ethylidene]-2-(1'H,3H-spiro[2-benzofuran-1,4'-piperidin]-1'-yl)-1,3-thiazol-4(5H)-one,
(5E)-5-[1-(pyridin-4-yl)ethylidene]-2-(1'H,3H-spiro[2-benzofuran-1,4'-piperidin]-1'-yl)-1,3-thiazol-4(5H)-one,
(5Z)-5-[1-(1-methyl-1H-pyrrol-2-yl)ethylidene]-2-(1'H,3H-spiro[2-benzofuran-1,4'-piperidin]-1'-yl)-1,3-thiazol-4(5H)-one,
(5Z)-5-[1-(pyridin-2-yl)ethylidene]-2-(1'H,3H-spiro[2-benzofuran-1,4'-piperidin]-1'-yl)-1,3-thiazol-4(5H)-one,
(5Z)-5-[1-(pyridin-3-yl)ethylidene]-2-(1'H,3H-spiro[2-benzofuran-1,4'-piperidin]-1'-yl)-1,3-thiazol-4(5H)-one,
(5E/Z)-5-[1-(2-fluorophenyl)ethylidene]-2-(1'H,3H-spiro[2-benzofuran-1,4'-piperidin]-1'-yl)-1,3-thiazol-4(5H)-one, tert-butyl 4-[4-oxo-2-(1'H,3H-spiro[2-benzofuran-1,4'-piperidin]-1'-yl)-1,3-thiazol-5(4H)-ylidene]piperidine-1-carboxylate,
(5E/Z)-5-(1-cyclopropylethylidene)-2-(1'H,3H-spiro[2-benzofuran-1,4'-piperidin]-1'-yl)-1,3-thiazol-4(5H)-one,
(5E/Z)-5-(1-cyclopentylethylidene)-2-(1'H,3H-spiro[2-benzofuran-1,4'-piperidin]-1'-yl)-1,3-thiazol-4(5H)-one,
2-(1'H,3H-spiro[2-benzofuran-1,4'-piperidin]-1'-yl)-5-(tetrahydro-4H-pyran-4-ylidene)-1,3-thiazol-4(5H)-one,
(5Z)-5-(3,4-dihydronaphthalen-1(2H)-ylidene)-2-(1'H,3H-spiro[2-benzofuran-1,4'-piperidin]-1'-yl)-1,3-thiazol-4(5H)-one,
(5Z)-5-(2,3-dihydro-1H-inden-1-ylidene)-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-(6,7,8,9-tetrahydro-5H-benzo[7]annulen-5-ylidene)-1,3-thiazol-4(5H)-one,
(5E/Z)-5-[1-(2-chloropyridin-4-yl)ethylidene]-2-(1'H,3H-spiro[2-benzofuran-1,4'-piperidin]-1'-yl)-1,3-thiazol-4(5H)-one,
(5E/Z)-5-[1-(6-chloropyridin-3-yl)ethylidene]-2-(1'H,3H-spiro[2-benzofuran-1,4'-piperidin]-1'-yl)-1,3-thiazol-4(5H)-one,
(5E/Z)-5-(1-methoxypropan-2-ylidene)-2-(1'H,3H-spiro[2-benzofuran-1,4'-piperidin]-1'-yl)-1,3-thiazol-4(5H)-one,
(5E/Z)-5-(1-fluoropropan-2-ylidene)-2-(1'H,3H-spiro[2-benzofuran-1,4'-piperidin]-1'-yl)-1,3-thiazol-4(5H)-one,
5-cyclohexylidene-2-(1'H,3H-spiro[2-benzofuran-1,4'-piperidin]-1'-yl)-1,3-thiazol-4(5H)-one,
5-cyclopentylidene-2-(1'H,3H-spiro[2-benzofuran-1,4'-piperidin]-1'-yl)-1,3-thiazol-4(5H)-one,
(5E/Z)-5-(5-hydroxy-2,3-dihydro-1H-inden-1-ylidene)-2-(1'H,3H-spiro[2-benzofuran-1,4'-piperidin]-1'-yl)-1,3-thiazol-4(5H)-one,
(5E/Z)-5-[hexahydro-1,2,4-(methanetriyl)pentalen-5(1H)-ylidene]-2-(1'H,3H-spiro[2-benzofuran-1,4'-piperidin]-1'-yl)-1,3-thiazol-4(5H)-one,
(5E)-5-[1-(2-fluorophenyl)ethylidene]-2-(1'H,3H-spiro[2-benzofuran-1,4'-piperidin]-1'-yl)-1,3-thiazol-4(5H)-one,
(5Z)-5-[1-(2-fluorophenyl)ethylidene]-2-(1'H,3H-spiro[2-benzofuran-1,4'-piperidin]-1'-yl)-1,3-thiazol-4(5H)-one,
(5E)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one,
(5Z)-5-(1-{[tert-butyl(dimethyl)silyl]oxy}propan-2-ylidene)-2-(1'H,3H-spiro[2-benzofuran-1,4'-piperidin]-1'-yl)-1,3-thiazol-4(5H)-one,
5-(1,1-dioxidotetrahydro-4H-thiopyran-4-ylidene)-2-(1'H,3H-spiro[2-benzofuran-1,4'-piperidin]-1'-yl)-1,3-thiazol-4(5H)-one,
(5Z)-5-[1-(2-fluoropyridin-3-yl)ethylidene]-2-(1'H,3H-spiro[2-benzofuran-1,4'-piperidin]-1'-yl)-1,3-thiazol-4(5H)-one,
(5Z)-5-[1-(1-methyl-1H-pyrazol-4-yl)ethylidene]-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-[1-(1,3-thiazol-2-yl)ethylidene]-1,3-thiazol-4(5H)-one,
(5E/Z)-5-[1-(5-methyl-1,2-oxazol-3-yl)propylidene]-2-(1'H,3H-spiro[2-benzofuran-1,4'-piperidin]-1'-yl)-1,3-thiazol-4(5H)-one,
tert-butyl {(2E)-2-[4-oxo-2-(1'H,3H-spiro[2-benzofuran-1,4'-piperidin]-1'-yl)-1,3-thiazol-5(4H)-ylidene]propyl}carbamate,
(5E)-5-(1-aminopropan-2-ylidene)-2-(1'H,3H-spiro[2-benzofuran-1,4'-piperidin]-1'-yl)-1,3-thiazol-4(5H)-one hydrochloride (1:1),
(5E/Z)-8-chloro-5-[4-oxo-2-(1'H,3H-spiro[2-benzofuran-1,4'-piperidin]-1'-yl)-1,3-thiazol-5(4H)-ylidene]-2,3,4,5-tetrahydro-1H-2-benzazepin-1-one,
5-[1-(methylsulfonyl)piperidin-4-ylidene]-2-(1'H,3H-spiro[2-benzofuran-1,4'-piperidin]-1'-yl)-1,3-thiazol-4(5H)-one,
5-(1,3-difluoropropan-2-ylidene)-2-(1'H,3H-spiro[2-benzofuran-1,4'-piperidin]-1'-yl)-1,3-thiazol-4(5H)-one,
(5E/Z)-5-(but-3-en-2-ylidene)-2-(1'H,3H-spiro[2-benzofuran-1,4'-piperidin]-1'-yl)-1,3-thiazol-4(5H)-one,
(5Z)-2-(1'H,3H-spiro[2-benzofuran-1,4'-piperidin]-1'-yl)-5-(1,1,1-trifluoropropan-2-ylidene)-1,3-thiazol-4(5H)-one,
2-[4-oxo-2-(1'H,3H-spiro[2-benzofuran-1,4'-piperidin]-1'-yl)-1,3-thiazol-5(4H)-ylidene]propane-1,3-diyl diacetate,
(5E/Z)-5-(2-methoxycyclohexylidene)-2-(1'H,3H-spiro[2-benzofuran-1,4'-piperidin]-1'-yl)-1,3-thiazol-4(5H)-one,
(3E/Z)-3-[4-oxo-2-(1'H,3H-spiro[2-benzofuran-1,4'-piperidin]-1'-yl)-1,3-thiazol-5(4H)-ylidene]-1,3-dihydro-2H-indol-2-one,
5-cyclobutylidene-2-(1'H,3H-spiro[2-benzofuran-1,4'-piperidin]-1'-yl)-1,3-thiazol-4(5H)-one,
(5E/Z)-5-(dihydro-2H-pyran-3(4H)-ylidene)-2-(1'H,3H-spiro[2-benzofuran-1,4'-piperidin]-1'-yl)-1,3-thiazol-4(5H)-one,
(5E/Z)-5-[1-(2-methylpyridin-4-yl)ethylidene]-2-(1'H,3H-spiro[2-benzofuran-1,4'-piperidin]-1'-yl)-1,3-thiazol-4(5H)-one,
(5E/Z)-2-(1'H,3H-spiro[2-benzofuran-1,4'-piperidin]-1'-yl)-5-[1-(tetrahydro-2H-pyran-4-yl)ethylidene]-1,3-thiazol-4(5H)-one,
(5Z)-5-[1-(5-methyl-1,2-oxazol-3-yl)ethylidene]-2-(1'H,3H-spiro[2-benzofuran-1,4'-piperidin]-1'-yl)-1,3-thiazol-4(5H)-one),
tert-butyl (4E/Z)-4-[4-oxo-2-(1'H,3H-spiro[2-benzofuran-1,4'-piperidin]-1'-yl)-1,3-thiazol-5(4H)-ylidene]azepane-1-carboxylate,
(5E/Z)-5-(azepan-4-ylidene)-2-(1'H,3H-spiro[2-benzofuran-1,4'-piperidin]-1'-yl)-1,3-thiazol-4(5H)-one hydrochloride,
5-(diphenylmethylidene)-2-(1'H,3H-spiro[2-benzofuran-1,4'-piperidin]-1'-yl)-1,3-thiazol-4(5H)-one,
(5Z)-5-[1-(2-chloropyridin-3-yl)ethylidene]-2-(1'H,3H-spiro[2-benzofuran-1,4'-piperidin]-1'-yl)-1,3-thiazol-4(5H)-one,
(5E)-5-[1-(2-chloropyridin-3-yl)ethylidene]-2-(1'H,3H-spiro[2-benzofuran-1,4'-piperidin]-1'-yl)-1,3-thiazol-4(5H)-one,
(5E/Z)-5-[1-(6-methoxypyridin-3-yl)ethylidene]-2-(1'H,3H-spiro[2-benzofuran-1,4'-piperidin]-1'-yl)-1,3-thiazol-4(5H)-one,
(5E/Z)-5-[1-(2,4-dimethyl-1,3-oxazol-5-yl)ethylidene]-2-(1'H,3H-spiro[2-benzofuran-1,4'-piperidin]-1'-yl)-1,3-thiazol-4(5H)-one, (5E/Z)-5-(1H-isochromen-4(3H)-ylidene)-2-(1'H,3H-spiro[2-benzofuran-1,4'-piperidin]-1'-yl)-1,3-thiazol-4(5H)-one,
tert-butyl (3E/Z)-3-[4-oxo-2-(1'H,3H-spiro[2-benzofuran-1,4'-piperidin]-1'-yl)-1,3-thiazol-5(4H)-ylidene]piperidine-1-carboxylate,
(5E/Z)-5-(3-chloro-6,7,8,9-tetrahydro-5H-benzo[7]annulen-5-ylidene)-2-(1'H,3H-spiro[2-benzofuran-1,4'-piperidin]-1'-yl)-1,3-thiazol-4(5H)-one,
(5Z)-5-(pyridin-2-ylmethylidene)-2-(1'H,3H-spiro[2-benzofuran-1,4'-piperidin]-1'-yl)-1,3-thiazol-4(5H)-one,
5-[(5-methyl-1,2-oxazol-3-yl)methylidene]-2-(1'H,3H-spiro[2-benzofuran-1,4'-piperidin]-1'-yl)-1,3-thiazol-4(5H)-one,
(5E)-5-(2-methoxy-1-phenylethylidene)-2-(1'H,3H-spiro[2-benzofuran-1,4'-piperidin]-1'-yl)-1,3-thiazol-4(5H)-one,
5-[(5-methyl-1,2-oxazol-3-yl)methylidene]-2-(1'H,3H-spiro[2-benzofuran-1,4'-piperidin]-1'-yl)-1,3-thiazol-4(5H)-one,
5-(pyridin-3-ylmethylidene)-2-(1'H,3H-spiro[2-benzofuran-1,4'-piperidin]-1'-yl)-1,3-thiazol-4(5H)-one,
5-(pyridin-4-ylmethylidene)-2-(1'H,3H-spiro[2-benzofuran-1,4'-piperidin]-1'-yl)-1,3-thiazol-4(5H)-one,
(5Z)-5-[1-(6-chloropyridin-3-yl)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)ethylidene]-2-(1'H,3H-spiro[2-benzofuran-1,4'-piperidin]-1'-yl)-1,3-thiazol-4(5H)-one,
5-(10,11-dihydro-5H-dibenzo[a,d][7]annulen-5-ylidene)-2-(1'H,3H-spiro[2-benzofuran-1,4'-piperidin]-1'-yl)-1,3-thiazol-4(5H)-one,
5-(5H-dibenzo[a,d][7]annulen-5-ylidene)-2-(1'H,3H-spiro[2-benzofuran-1,4'-piperidin]-1'-yl)-1,3-thiazol-4(5H)-one,
5-[bis(4-chlorophenyl)methylidene]-2-(1'H,3H-spiro[2-benzofuran-1,4'-piperidin]-1'-yl)-1,3-thiazol-4(5H)-one,
5-[bis(4-fluorophenyl)methylidene]-2-(1'H,3H-spiro[2-benzofuran-1,4'-piperidin]-1'-yl)-1,3-thiazol-4(5H)-one,
2-(1'H,3H-spiro[2-benzofuran-1,4'-piperidin]-1'-yl)-5-(9H-thioxanthen-9-ylidene)-1,3-thiazol-4(5H)-one,
2-(1'H,3H-spiro[2-benzofuran-1,4'-piperidin]-1'-yl)-5-(9H-xanthen-9-ylidene)-1,3-thiazol-4(5H)-one,
5-(9H-fluoren-9-ylidene)-2-(1'H,3H-spiro[2-benzofuran-1,4'-piperidin]-1'-yl)-1,3-thiazol-4(5H)-one,
(5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one,
(5E)-5-[1-(3,5-dimethyl-1,2-oxazol-4-yl)ethylidene]-2-(1'H,3H-spiro[2-benzofuran-1,4'-piperidin]-1'-yl)-1,3-thiazol-4(5H)-one,
(5Z)-5-[1-(1H-imidazol-2-yl)ethylidene]-2-(1'H,3H-spiro[2-benzofuran-1,4'-piperidin]-1'-yl)-1,3-thiazol-4(5H)-one,
(5E/Z)-5-[1-(furo[3,2-b]pyridin-2-yl)ethylidene]-2-(1'H,3H-spiro[2-benzofuran-1,4'-piperidin]-1'-yl)-1,3-thiazol-4(5H)-one,
(5E/Z)-5-[1-(5-methyl-1H-imidazol-4-yl)ethylidene]-2-(1'H,3H-spiro[2-benzofuran-1,4'-piperidin]-1'-yl)-1,3-thiazol-4(5H)-one,
5-[di(pyridin-2-yl)methylidene]-2-(1'H,3H-spiro[2-benzofuran-1,4'-piperidin]-1'-yl)-1,3-thiazol-4(5H)-one,
5-(1,1,1,3,3,3-hexafluoropropan-2-ylidene)-2-(1'H,3H-spiro[2-benzofuran-1,4'-piperidin]-1'-yl)-1,3-thiazol-4(5H)-one,
(5E/Z)-5-[1-(2,4-dimethyl-1,3-thiazol-5-yl)ethylidene]-2-(1'H,3H-spiro[2-benzofuran-1,4'-piperidin]-1'-yl)-1,3-thiazol-4(5H)-one,
5-(1,3-dichloropropan-2-ylidene)-2-(1'H,3H-spiro[2-benzofuran-1,4'-piperidin]-1'-yl)-1,3-thiazol-4(5H)-one,
5-(heptan-4-ylidene)-2-(1'H,3H-spiro[2-benzofuran-1,4'-piperidin]-1'-yl)-1,3-thiazol-4(5H)-one,
5-(dicyclopropylmethylidene)-2-(1'H,3H-spiro[2-benzofuran-1,4'-piperidin]-1'-yl)-1,3-thiazol-4(5H)-one,
5-(2,6-dimethylheptan-4-ylidene)-2-(1'H,3H-spiro[2-benzofuran-1,4'-piperidin]-1'-yl)-1,3-thiazol-4(5H)-one,
(5E/Z)-5-[1-(1H-imidazol-5-yl)ethylidene]-2-(1'H,3H-spiro[2-benzofuran-1,4'-piperidin]-1'-yl)-1,3-thiazol-4(5H)-one,
5-(dicyclopentylmethylidene)-2-(1'H,3H-spiro[2-benzofuran-1,4'-piperidin]-1'-yl)-1,3-thiazol-4(5H)-one,
5-[di(pyridin-3-yl)methylidene]-2-(1'H,3H-spiro[2-benzofuran-1,4'-piperidin]-1'-yl)-1,3-thiazol-4(5H)-one,
5-(2,4-dimethylpentan-3-ylidene)-2-(1'H,3H-spiro[2-benzofuran-1,4'-piperidin]-1'-yl)-1,3-thiazol-4(5H)-one,
(5E/Z)-5-[1-(methylsulfonyl)propan-2-ylidene]-2-(1'H,3H-spiro[2-benzofuran-1,4'-piperidin]-1'-yl)-1,3-thiazol-4(5H)-one,
5-(di-1H-pyrrol-2-ylmethylidene)-2-(1'H,3H-spiro[2-benzofuran-1,4'-piperidin]-1'-yl)-1,3-thiazol-4(5H)-one,
(5E)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one,
(5E)-5-(2-hydroxy-1-phenylethylidene)-2-(1'H,3H-spiro[2-benzofuran-1,4'-piperidin]-1'-yl)-1,3-thiazol-4(5H)-one,
5-(dicyclohexylmethylidene)-2-(1'H,3H-spiro[2-benzofuran-1,4'-piperidin]-1'-yl)-1,3-thiazol-4(5H)-one,
(5Z)-5-(2-{[tert-butyl(dimethyl)silyl]oxy}-1-phenylethylidene)-2-(1'H,3H-spiro[2-benzofuran-1,4'-piperidin]-1'-yl)-1,3-thiazol-4(5H)-one,
(5Z)-5-(2-hydroxy-1-phenylethylidene)-2-(1'H,3H-spiro[2-benzofuran-1,4'-piperidin]-1'-yl)-1,3-thiazol-4(5H)-one,
(5Z)-5-(cyclopent-2-en-1-ylidene)-2-(1'H,3H-spiro[2-benzofuran-1,4'-piperidin]-1'-yl)-1,3-thiazol-4(5H)-one,
(5E)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)-2-hydroxyethylidene]-2-(1'H,3H-spiro[2-benzofuran-1,4'-piperidin]-1'-yl)-1,3-thiazol-4(5H)-one,
(5Z)-5-[2-{[tert-butyl(dimethyl)silyl]oxy}-1-(6-chloropyridin-3-yl)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)-2-methylpropylidene]-2-(1'H,3H-spiro[2-benzofuran-1,4'-piperidin]-1'-yl)-1,3-thiazol-4(5H)-one,
(5Z)-5-[1-(6-chloropyridin-3-yl)propylidene]-2-(1'H,3H-spiro[2-benzofuran-1,4'-piperidin]-1'-yl)-1,3-thiazol-4(5H)-one,
(5E)-5-[1-(6-chloropyridin-3-yl)propylidene]-2-(1'H,3H-spiro[2-benzofuran-1,4'-piperidin]-1'-yl)-1,3-thiazol-4(5H)-one, 1'-{(5Z)-5-[1-(6-methylpyridin-3-yl)ethylidene]-4-oxo-4,5-dihydro-1,3-thiazol-2-yl}-3H-spiro[2-benzofuran-1,4'-piperidin]-3-one,
1'-{(5E)-5-[1-(6-methylpyridin-3-yl)ethylidene]-4-oxo-4,5-dihydro-1,3-thiazol-2-yl}-3H-spiro[2-benzofuran-1,4'-piperidin]-3-one,
1'-{(5Z)-5-[1-(6-chloropyridin-3-yl)ethylidene]-4-oxo-4,5-dihydro-1,3-thiazol-2-yl}-3H-spiro[2-benzofuran-1,4'-piperidin]-3-one,
1'-{(5E)-5-[1-(6-chloropyridin-3-yl)ethylidene]-4-oxo-4,5-dihydro-1,3-thiazol-2-yl}-3H-spiro[2-benzofuran-1,4'-piperidin]-3-one,
1'-[5-(dicyclopropylmethylidene)-4-oxo-4,5-dihydro-1,3-thiazol-2-yl]-3H-spiro[2-benzofuran-1,4'-piperidin]-3-one,
1'-[(5E)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one,
1'-[(5Z)-5-(2-{[tert-butyl(dimethyl)silyl]oxy}-1-phenylethylidene)-4-oxo-4,5-dihydro-1,3-thiazol-2-yl]-3H-spiro[2-benzofuran-1,4'-piperidin]-3-one,
1'-[(5Z)-5-(2-hydroxy-1-phenylethylidene)-4-oxo-4,5-dihydro-1,3-thiazol-2-yl]-3H-spiro[2-benzofuran-1,4'-piperidin]-3-one,
1'-[(5E)-5-(2-hydroxy-1-phenylethylidene)-4-oxo-4,5-dihydro-1,3-thiazol-2-yl]-3H-spiro[2-benzofuran-1,4'-piperidin]-3-one,
1'-{(5E)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one,
1'-{(5E)-5-[1-(6-chloropyridin-3-yl)-2-hydroxyethylidene]-4-oxo-4,5-dihydro-1,3-thiazol-2-yl}-3H-spiro[2-benzofuran-1,4'-piperidin]-3-one,
1'-{(5Z)-5-[2-{[tert-butyl(dimethyl)silyl]oxy}-1-(6-chloropyridin-3-yl)ethylidene]-4-oxo-4,5-dihydro-1,3-thiazol-2-yl}-3H-spiro[2-benzofuran-1,4'-piperidin]-3-one,
1'-{(5Z)-5-[1-(6-chloropyridin-3-yl)-2-hydroxyethylidene]-4-oxo-4,5-dihydro-1,3-thiazol-2-yl}-3H-spiro[2-benzofuran-1,4'-piperidin]-3-one,
1'-{(5E)-5-[1-(6-chloropyridin-3-yl)-2-methylpropylidene]-4-oxo-4,5-dihydro-1,3-thiazol-2-yl}-3H-spiro[2-benzofuran-1,4'-piperidin]-3-one,
1'-{(5E)-5-[1-(6-chloropyridin-3-yl)propylidene]-4-oxo-4,5-dihydro-1,3-thiazol-2-yl}-3H-spiro[2-benzofuran-1,4'-piperidin]-3-one,
1'-{(5Z)-5-[1-(6-chloropyridin-3-yl)propylidene]-4-oxo-4,5-dihydro-1,3-thiazol-2-yl}-3H-spiro[2-benzofuran-1,4'-piperidin]-3-one,
(5Z)-5-(1-phenylethylidene)-2-(1'H,3H-spiro[2-benzofuran-1,4'-piperidin]-1'-yl)-1,3-thiazol-4(5H)-one,
(5E)-5-(1-phenylethylidene)-2-(1'H,3H-spiro[2-benzofuran-1,4'-piperidin]-1'-yl)-1,3-thiazol-4(5H)-one,
(5E)-5-[1-(6-methylpyridin-3-yl)ethylidene]-2-(1'H,3H-spiro[2-benzofuran-1,4'-piperidin]-1'-yl)-1,3-thiazol-4(5H)-one,
(5E)-5-[1-(4-chlorophenyl)-2-methylpropylidene]-2-(1'H,3H-spiro[2-benzofuran-1,4'-piperidin]-1'-yl)-1,3-thiazol-4(5H)-one,
(5E)-5-[1-(3-methylpyridin-2-yl)ethylidene]-2-(1'H,3H-spiro[2-benzofuran-1,4'-piperidin]-1'-yl)-1,3-thiazol-4(5H)-one,
1'-[(5Z)-4-oxo-5-(1-phenylethylidene)-4,5-dihydro-1,3-thiazol-2-yl]-3H-spiro[2-benzofuran-1,4'-piperidin]-3-one,
1'-[(5E)-4-oxo-5-(1-phenylethylidene)-4,5-dihydro-1,3-thiazol-2-yl]-3H-spiro[2-benzofuran-1,4'-piperidin]-3-one,
(5Z)-5-[1-(3-fluoropyridin-4-yl)ethylidene]-2-(1'H,3H-spiro[2-benzofuran-1,4'-piperidin]-1'-yl)-1,3-thiazol-4(5H)-one,
tert-butyl {(2E/Z)-2-[4-oxo-2-(1'H,3H-spiro[2-benzofuran-1,4'-piperidin]-1'-yl)-1,3-thiazol-5(4H)-ylidene]-2-phenylethyl}carbamate,
(5E/Z)-5-(2-amino-1-phenylethylidene)-2-(1'H,3H-spiro[2-benzofuran-1,4'-piperidin]-1'-yl)-1,3-thiazol-4(5H)-one trifluoroacetate,
5-(1,3-dihydro-2H-inden-2-ylidene)-2-(1'H,3H-spiro[2-benzofuran-1,4'-piperidin]-1'-yl)-1,3-thiazol-4(5H)-one,
(5E/Z)-5-[1-(6-chloropyridin-3-yl)ethylidene]-2-(1'H,7H-spiro[furo[3,4-b]pyridine-5,4'-piperidin]-1'-yl)-1,3-thiazol-4(5H)-one,
5-(1,3-dimethoxypropan-2-ylidene)-2-(1'H,7H-spiro[furo[3,4-b]pyridine-5,4'-piperidin]-1'-yl)-1,3-thiazol-4(5H)-one,
(5E/Z)-5-(2-methoxycyclohexylidene)-2-(1'H,7H-spiro[furo[3,4-b]pyridine-5,4'-piperidin]-1'-yl)-1,3-thiazol-4(5H)-one,
(5E/Z)-5-[1-(pyridin-3-yl)ethylidene]-2-(1'H,7H-spiro[furo[3,4-b]pyridine-5,4'-piperidin]-1'-yl)-1,3-thiazol-4(5H)-one,
(5E/Z)-5-[1-(6-methylpyridin-3-yl)ethylidene]-2-(1'H,7H-spiro[furo[3,4-b]pyridine-5,4'-piperidin]-1'-yl)-1,3-thiazol-4(5H)-one,
(5E/Z)-5-[1-(2,4-dimethyl-1,3-oxazol-5-yl)ethylidene]-2-(1'H,7H-spiro[furo[3,4-b]pyridine-5,4'-piperidin]-1'-yl)-1,3-thiazol-4(5H)-one,
(5E/Z)-5-(1H-isochromen-4(3H)-ylidene)-2-(1'H,7H-spiro[furo[3,4-b]pyridine-5,4'-piperidin]-1'-yl)-1,3-thiazol-4(5H)-one,
(5Z)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one,
(5E)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one,
(5Z)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one,
(5E)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one,
(5Z)-5-[1-phenyl($^2$H$_3$)ethylidene]-2-(1'H,3H-spiro[2-benzofuran-1,4'-piperidin]-1'-yl)-1,3-thiazol-4(5H)-one, and
(5E)-5-[1-phenyl($^2$H$_3$)ethylidene]-2-(1'H,3H-spiro[2-benzofuran-1,4'-piperidin]-1'-yl)-1,3-thiazol-4(5H)-one.

10. The compound of claim 1, selected from the group consisting of
(5E/Z)-5-[1-(4-chlorophenyl)ethylidene]-2-(1'H,5H-spiro[furo[3,4-b]pyridine-7,4'-piperidin]-1'-yl)-1,3-thiazol-4(5H)-one,
1'-{(5E/Z)-5-[1-(4-chlorophenyl)ethylidene]-4-oxo-4,5-dihydro-1,3-thiazol-2-yl}-3H-spiro[2-benzofuran-1,4'-piperidin]-3-one,
(5E/Z)-5-[1-(4-chlorophenyl)ethylidene]-2-(1'H,7H-spiro[furo[3,4-b]pyridine-5,4'-piperidin]-1'-yl)-1,3-thiazol-4(5H)-one, (5Z)-5-[1-(6-methylpyridin-3-yl)ethylidene]-2-(1'H,3H-spiro[2-benzofuran-1,4'-piperidin]-1'-yl)-1,3-thiazol-4(5H)-one, 5-(1,3-dimethoxypropan-2-ylidene)-2-(1'H,3H-spiro[2-benzofuran-1,4'-piperidin]-1'-yl)-1,3-thiazol-4(5H)-one, (5Z)-5-[1-(4-chlorophenyl)ethylidene]-2-(1'H,3H-spiro[2-benzofuran-1,4'-piperidin]-1'-yl)-1,3-thiazol-4(5H)-one, (5E/Z)-5-[1-(6-chloropyridin-3-yl)ethylidene]-2-(1'H,3H-spiro[2-benzofuran-1,4'-piperidin]-1'-yl)-1,3-thiazol-4(5H)-one, (5Z)-5-[1-(2-fluoropyridin-3-yl)ethylidene]-2-(1'H,3H-spiro[2-benzofuran-1,4'-piperidin]-1'-yl)-1,3-thiazol-4(5H)-one, (5E/Z)-5-[1-(2,4-dimethyl-1,3-oxazol-5-yl)ethylidene]-2-(1'H,3H-spiro[2-benzofuran-1,4'-piperidin]-1'-yl)-1,3-thiazol-4(5H)-one, (5E)-5-(2-methoxy-1-phenylethylidene)-2-(1'H,3H-spiro[2-benzofuran-1,4'-piperidin]-1'-yl)-1,3-thiazol-4(5H)-one, (5Z)-5-[1-(6-chloropyridin-3-yl)ethylidene]-2-(1'H,3H-spiro[2-benzofuran-1,4'-piperidin]-1'-yl)-1,3-thiazol-4(5H)-one, (5E)-5-[1-(6-chloropyridin-3-yl)ethylidene]-2-(1'H,3H-spiro[2-benzofuran-1,4'-piperidin]-1'-yl)-1,3-thiazol-4(5H)-one, (5E)-5-(2-hydroxy-1-phenylethylidene)-2-(1'H,3H-spiro[2-benzofuran-1,4'-piperidin]-1'-yl)-1,3-thiazol-4(5H)-one, (5E)-5-[1-(6-chloropyridin-3-yl)-2-hydroxyethylidene]-2-(1'H,3H-spiro[2-benzofuran-1,4'-piperidin]-1'-yl)-1,3-thiazol-4(5H)-one, (5Z)-5-(1-phenylethylidene)-2-(1'H,3H-spiro[2-benzofuran-1,4'-piperidin]-1'-yl)-1,3-thiazol-4(5H)-one, (5E)-5-(1-phenylethylidene)-2-(1'H,3H-spiro[2-benzofuran-1,4'-piperidin]-1'-yl)-1,3-thiazol-4(5H)-one, 1'-[(5Z)-4-oxo-5-(1-phenylethylidene)-4,5-dihydro-1,3-thiazol-2-yl]-3H-spiro[2-benzofuran-1,4'-piperidin]-3-one, (5Z)-5-[1-(6-methylpyridin-3-yl)($^2$H$_3$)ethylidene]-2-(1'H,3H-spiro[2-benzofuran-1,4'-piperidin]-1'-yl)-1,3-thiazol-4(5H)-one, (5Z)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one, (5E)-5-[1-(6-chloropyridin-3-yl)($^2$H$_3$)ethylidene]-2-(1'H,3H-spiro[2-benzofuran-1,4'-piperidin]-1'-yl)-1,3-thiazol-4(5H)-one, (5Z)-5-[1-phenyl($^2$H$_3$)ethylidene]-2-(1'H,3H-spiro[2-benzofuran-1,4'-piperidin]-1'-yl)-1,3-thiazol-4(5H)-one, and (5E)-5-[1-phenyl($^2$H$_3$)ethylidene]-2-(1'H,3H-spiro[2-benzofuran-1,4'-piperidin]-1'-yl)-1,3-thiazol-4(5H)-one.

11. A pharmaceutical composition comprising a compound of claim 1 and a pharmaceutically acceptable carrier and/or a pharmaceutically acceptable auxiliary substance.

12. A method for treating autistic spectrum disorders, the method comprising administering an effective amount of a compound of formula I to a human being or animal in need thereof.

* * * * *